US009243281B2

(12) United States Patent
McKnight et al.

(10) Patent No.: US 9,243,281 B2
(45) Date of Patent: Jan. 26, 2016

(54) NEUROPROTECTIVE CHEMICALS AND METHODS FOR IDENTIFYING AND USING SAME

(71) Applicant: Board of Regents of The University of Texas System, Austin, TX (US)

(72) Inventors: Steven L. McKnight, Dallas, TX (US); Joseph M. Ready, Carrollton, TX (US); Andrew A. Pieper, Iowa City, IA (US); Gelin Wang, Plano, TX (US); Ting Han, Dallas, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 14/540,006

(22) Filed: Nov. 12, 2014

(65) Prior Publication Data
US 2015/0132783 A1 May 14, 2015

Related U.S. Application Data

(63) Continuation-in-part of application No. PCT/US2014/065058, filed on Nov. 11, 2014.

(60) Provisional application No. 61/902,680, filed on Nov. 11, 2013, provisional application No. 61/912,625, filed on Dec. 6, 2013, provisional application No. 61/993,328, filed on May 15, 2014.

(51) Int. Cl.
*C12Q 1/48* (2006.01)
*A61K 38/00* (2006.01)
*G01N 33/50* (2006.01)

(52) U.S. Cl.
CPC . *C12Q 1/48* (2013.01); *A61K 38/00* (2013.01); *G01N 33/5014* (2013.01); *G01N 33/5038* (2013.01)

(58) Field of Classification Search
CPC ........................................................ C12N 5/00
See application file for complete search history.

(56) References Cited

U.S. PATENT DOCUMENTS

| | | | |
|---|---|---|---|
| 3,409,628 A | 11/1968 | Berger et al. | |
| 3,518,250 A | 6/1970 | Schumaker | |
| 4,495,281 A | 1/1985 | Buckler et al. | |
| 5,234,923 A | 8/1993 | Poss et al. | |
| 5,306,609 A | 4/1994 | Mihayashi et al. | |
| 6,187,785 B1 | 2/2001 | Zefirov et al. | |
| 6,468,996 B1 | 10/2002 | Jeppesen et al. | |
| 6,514,968 B1 | 2/2003 | TenBrink | |
| 6,569,849 B1 | 5/2003 | Jorgensen et al. | |
| 6,770,656 B2 | 8/2004 | Halazy et al. | |
| 6,835,513 B2 | 12/2004 | Jubran et al. | |
| 6,849,640 B2 | 2/2005 | Ennis et al. | |
| 6,864,025 B2 | 3/2005 | Law et al. | |
| 7,018,988 B2 | 3/2006 | Halazy et al. | |
| 7,071,206 B2 | 7/2006 | Zefirov et al. | |
| 7,148,259 B1 | 12/2006 | Li et al. | |
| 7,438,916 B2 | 10/2008 | Rathore et al. | |
| 7,445,877 B2 | 11/2008 | Jubran et al. | |
| 7,449,478 B2 | 11/2008 | Hsieh et al. | |
| 7,807,704 B2 | 10/2010 | Thomas et al. | |
| 7,834,063 B2 | 11/2010 | Turnbull et al. | |
| 7,989,127 B2 | 8/2011 | Wu et al. | |
| 8,268,575 B2 | 9/2012 | Imai et al. | |
| 8,362,277 B2 | 1/2013 | McKnight et al. | |
| 8,604,074 B2 | 12/2013 | McKnight et al. | |
| 8,735,440 B2 | 5/2014 | McKnight et al. | |
| 8,748,473 B2 | 6/2014 | McKnight et al. | |
| 8,791,149 B2 | 7/2014 | McKnight et al. | |
| 8,877,797 B2 | 11/2014 | McKnight et al. | |
| 2003/0171309 A1 | 9/2003 | Halazy et al. | |
| 2003/0203296 A1 | 10/2003 | Law et al. | |
| 2003/0207188 A1 | 11/2003 | Jubran et al. | |
| 2003/0216427 A1 | 11/2003 | Halazy et al. | |
| 2005/0124675 A1 | 6/2005 | Hsieh et al. | |
| 2005/0277038 A1 | 12/2005 | Jubran et al. | |
| 2006/0038170 A1 | 2/2006 | Brunschwiler et al. | |
| 2007/0185152 A1 | 8/2007 | Yamashita et al. | |
| 2007/0196395 A1 | 8/2007 | Mackerell et al. | |
| 2007/0197524 A1 | 8/2007 | Brauer et al. | |
| 2007/0203236 A1 | 8/2007 | Smith et al. | |
| 2007/0275965 A1 | 11/2007 | Thomas et al. | |
| 2007/0293558 A1 | 12/2007 | Gao et al. | |
| 2008/0039629 A1 | 2/2008 | Ramesh et al. | |
| 2008/0058383 A1 | 3/2008 | Jernstedt et al. | |
| 2008/0255124 A1 | 10/2008 | Turnbull et al. | |
| 2009/0137420 A1 | 5/2009 | VonHoff et al. | |
| 2009/0143376 A1 | 6/2009 | Milburn et al. | |
| 2009/0163545 A1 | 6/2009 | Goldfarb | |
| 2009/0236229 A1 | 9/2009 | Advincula | |
| 2009/0246803 A1 | 10/2009 | Imai et al. | |
| 2010/0305121 A1 | 12/2010 | Smith et al. | |
| 2011/0003836 A1 | 1/2011 | McKnight et al. | |
| 2011/0015217 A1 | 1/2011 | McKnight et al. | |

(Continued)

FOREIGN PATENT DOCUMENTS

CN 101139347 A 3/2008
CN 101429198 A 5/2009

(Continued)

OTHER PUBLICATIONS

Pereira et al. Photochemistry and Photobiology, 1976, 24:237-242.*

(Continued)

*Primary Examiner* — Bin Shen

(74) *Attorney, Agent, or Firm* — Greenberg Traurig, LLP; David J. Dykeman; Fang Xie

(57) ABSTRACT

Provided herein are methods for identifying a compound having cell-protective (e.g., neuroprotective) activity. Compounds identified therefrom are also provided. These compounds can be used to treat various diseases, disorders, or conditions associated with, for example, unwanted cell death.

18 Claims, 35 Drawing Sheets
(27 of 35 Drawing Sheet(s) Filed in Color)

(56) References Cited

U.S. PATENT DOCUMENTS

| | | | |
|---|---|---|---|
| 2012/0022013 | A1 | 1/2012 | Sinclair et al. |
| 2012/0022096 | A1 | 1/2012 | McKnight et al. |
| 2012/0122924 | A1 | 5/2012 | Curtin et al. |
| 2012/0172584 | A1 | 7/2012 | Sauve et al. |
| 2013/0040977 | A1 | 2/2013 | McKnight et al. |
| 2013/0096181 | A1 | 4/2013 | Ashkenazi et al. |
| 2013/0184271 | A1 | 7/2013 | McKnight et al. |
| 2013/0184300 | A1 | 7/2013 | McKnight et al. |
| 2013/0184301 | A1 | 7/2013 | McKnight et al. |
| 2013/0190273 | A1 | 7/2013 | McKnight et al. |
| 2013/0190339 | A1 | 7/2013 | McKnight et al. |
| 2014/0057900 | A1 | 2/2014 | McKnight et al. |
| 2014/0094480 | A1 | 4/2014 | McKnight et al. |
| 2014/0343018 | A1 | 11/2014 | McKnight et al. |
| 2015/0057301 | A1 | 2/2015 | McKnight et al. |

FOREIGN PATENT DOCUMENTS

| | | |
|---|---|---|
| EP | 1 094 063 | 4/2001 |
| EP | 1 591 511 | 11/2005 |
| FR | 1167510 | 11/1958 |
| GB | 2 355 659 | 5/2001 |
| JP | 2007/223916 | 9/2007 |
| WO | WO 92/21660 | 12/1992 |
| WO | WO 96/34863 | 11/1996 |
| WO | WO 00/23425 | 4/2000 |
| WO | WO 00/78795 | 12/2000 |
| WO | WO 01/29028 | 4/2001 |
| WO | WO 01/71430 | 9/2001 |
| WO | WO 02/38142 | 5/2002 |
| WO | WO 02/060867 | 8/2002 |
| WO | WO 03/007069 | 1/2003 |
| WO | WO 03/007070 | 1/2003 |
| WO | WO 03/007071 | 1/2003 |
| WO | WO 03/032072 | 1/2003 |
| WO | WO 03/091247 | 11/2003 |
| WO | WO 2004/052885 | 6/2004 |
| WO | WO 2004/106335 | 9/2004 |
| WO | WO 2005/055951 | 6/2005 |
| WO | WO 2005/056522 | 6/2005 |
| WO | WO 2005/074971 | 8/2005 |
| WO | WO 2007/008541 | 1/2007 |
| WO | WO 2007/041697 | 4/2007 |
| WO | WO 2007/062399 | 5/2007 |
| WO | WO 2007/079239 | 7/2007 |
| WO | WO 2007/081091 | 7/2007 |
| WO | WO 2007/087425 | 8/2007 |
| WO | WO 2007/137227 | 11/2007 |
| WO | WO 2008/021745 | 2/2008 |
| WO | WO 2008/060190 | 5/2008 |
| WO | WO 2008/115098 | 9/2008 |
| WO | WO 2008/123796 | 10/2008 |
| WO | WO 2008/123800 | 10/2008 |
| WO | WO 2008/156105 | 12/2008 |
| WO | WO 2009/040517 | 4/2009 |
| WO | WO 2009/055828 | 4/2009 |
| WO | WO 2009/094668 | 7/2009 |
| WO | WO 2009/120717 | 10/2009 |
| WO | WO 2010/048446 | 4/2010 |
| WO | WO 2010/051503 | 5/2010 |
| WO | WO 2010/081115 | 7/2010 |
| WO | WO 2011/019417 | 2/2011 |
| WO | WO 2011/038162 | 3/2011 |
| WO | WO 2011/117668 | 9/2011 |
| WO | WO 2012/006419 | 1/2012 |
| WO | WO 2014/031125 | 2/2014 |
| WO | WO 2014/031986 | 2/2014 |
| WO | WO 2015/035051 | 3/2015 |

OTHER PUBLICATIONS

Newman et al. Cancer Research, 1981, 41:3483-3488.*
Awasthi et al. Int. J. Cancer, 1996, 68:333-339.*
Jantas et al. Neurotox Res., 2009, 15:24-37.*

Abad, J. et al., "Internal Oxidosqualenes: Determination of Absolute Configuration and Activity as Inhibitors of Purified Pig Liver Squalene Epoxidase," *J. Org. Chem.*, 60(12), pp. 3648-3656 (Jun. 1995).
Abrous, D. et al., "Adult Neurogenesis: From Precursors to Network and Physiology," *Physiol Rev*, vol. 85, pp. 523-569 (2005).
Alexander, M. et al., "A Central Strategy for Converting Natural Products into Fluorescent Probes," *ChemBioChem*, 7(3), pp. 409-416 (Mar. 2006).
Altman, J., "Are New Neurons Formed in the Brains of Adult Mammals?" *Science*, 135, pp. 1127-1128 (Mar. 1962).
Altman, J., "Autoradiographic Investigation of Cell Proliferation in the Brains of Rats and Cats," *Anat. Rec.*, 145, pp. 573-591 (Apr. 1963).
Altman, J., "Autoradiographic and Histological Evidence of Postnatal Hippocampal Neurogenesis in Rats," *J. Comp. Neur.*, 124(3), pp. 319-335 (Jun. 1965).
Altman, J., "Autoradiographic and Histological Studies of Postnatal Neurogenesis: I. A Longitudinal Investigation of the Kinetics, Migration and Transformation of Cells Incorporating Tritiated Thymidine in Neonate Rats, with Special Reference to Postnatal Neurogenesis in Some Brain Regions," *J. Comp. Neur.*, 126(3), pp. 337-389 (Mar. 1966).
Altman, J., "Autoradiographic and Histological Studies of Postnatal Neurogenesis: II. A Longitudinal Investigation of the Kinetics, Migration and Transformation of Cells Incorporating Tritiated Thymidine in Infant Rats, with Special Reference to Postnatal Neurogenesis in Some Brain Regions," *J. Comp. Neur.*, 128(4), pp. 431-473 (Dec. 1966).
Altman, J., "Autoradiographic and Histological Studies of Postnatal Neurogenesis: IV. Cell Proliferation and Migration in the Anterior Forebrain, with Special Reference to Persisting Neurogenesis in the Olfactory Bulb," *J. Comp. Neur.*, 137(4), pp. 433-457 (Dec. 1969).
Araki et al., "Increased Nuclear NAD Biosynthesis and SIRT1 Activation Prevent Axonal Degeneration" *Science* 305:1010-1013, Aug. 13, 2004.
AsInEx Chemical Library, Compound "9H-Carbazole-9-Ethanol, 3, 6-dibromo-a-[[(3-chlorophenyl)amino]methyl]" (2001).
Asso, V. et al., "α-Naphthylaminopropan-2-ol Derivatives as BACE1 Inhibitors," *ChemMedChem*, 3(10), pp. 1530-1534 (Oct. 2008).
Bachurin, S. et al., "Antihistamine Agent Dimebon as a Novel Neuroprotector and a Cognition Enhancer," *Ann. N.Y. Acad. Sci.*, 939, pp. 425-435 (Jun. 2001).
Bachurin, S. et al., "Mitochondria as a Target for Neurotoxins and Neuroprotective Agents," *Ann. N.Y. Acad. Sci.*, 993, pp. 334-344 (May 2003).
Bachurin, S. et al., "Questions and Answers: Session VII: Oxidative Stress, Mitochondria, and Approaches to Neuroprotection," *Ann. N.Y. Acad. Sci.*, 993, pp. 345-349 (May 2003).
Berg et al., "New Neuronal Growth Factors" *Ann. Rev. Neurosci.*, 7: 149-170 (Jul. 1984).
Beyer, M. et al., "Synthesis of Novel Aromatic Nitroxides as Potential DNA Intercalators. An EPR Spectroscopical and DFT Computational Study," *J Org. Chem.*, 68(6), pp. 2209-2215 (Mar. 2003).
Boekelheide, V. et al., "Curariform Activity and Chemical Structure. VII. Some 1-Skatylisoquinoline Derivatives and a Novel Method for their Synthesis," *J. Am. Chem. Soc.*, 72(5), pp. 2134-2137 (May 1950).
Boldrini, M. et al., "Antidepressants Increase Neural Progenitor Cells in the Human Hippocampus," *Neuropsychopharmacology*, 34(11), pp. 2376-2389 (Oct. 2009).
Bombrun, A. et al., "3,6-Dibromocarbazole Piperazine Derivatives of 2-Propanol as First Inhibitors of Cytochrome c Release via Bax Channel Modulation," *J. Med. Chem.*, 46(21), pp. 4365-4368 (Oct. 2003).
Borrell-Pages, M. et al., "Huntington's Disease: From Huntington Function and Dysfunction to Therapeutic Strategies," *Cell. Mol. Life Sci.*, 63(22), pp. 2462-2660 (Nov. 2006).
Bradshaw et al., The Development of the Antitumour Benzothiazole Prodrug, Phortress, as a Clinical Candidate, Current Medicinal Chemistry 11, pp. 1-13 (pp. 1241-1253) 2004; (retrieved from the Internet) http://www.pharminox.com/pdf/Phortess_rev.pdf.

(56) References Cited

OTHER PUBLICATIONS

Brown, J. et al., "Transient Expression of Doublecortin during Adult Neurogenesis," *The Journal of Comparative Neurology*, 467(1), pp. 1-10 (Dec. 2003).
Browne, S. et al., "The Energetics of Huntington's Disease," *Neurochemical Research*, 29(3), pp. 531-546 (Mar. 2004).
Burd, G. et al., "Ultrastructural Characterization of Synaptic Terminals Formed on Newly Generated Neurons in a Song Control Nucleus of the Adult Canary Forebrain," *The Journal of Comparative Neurology*, 240(2), pp. 143-152 (Oct. 1985).
Burns, A. et al., "Dimebon in Alzheimer's Disease: Old Drug for New Indication," *The Lancet*, 372, pp. 179-180 (Jul. 2008).
Cao, R. et al., "Synthesis, Acute Toxicities, and Antitumor Effects of Novel 9-Substituted β-Carboline Derivatives," *Bioorganic & Medicinal Chemistry*, 12(17), pp. 4613-4623 (Sep. 2004).
Cao, R. et al., "Design, Synthesis and In Vitro and In Vivo Antitumor Activities of Novel β-Carboline Derivatives," *European Journal of Medicinal Chemistry*, 40(10), pp. 991-1001 (Oct. 2005).
Cao, R. et al., "DNA Binding Properties of 9-Substituted Harmine Derivatives," *Biochemical and Biophysical Research Communications*, 338(3), pp. 1557-1563 Dec. (2005).
Cao, R. et al., "Synthesis and Cytotoxic Activities of 1-Benzylidine Substituted β-Carboline Derivatives," *Bioorganic & Medicinal Chemistry Letters*, 18(24), pp. 6558-6561 (Dec. 2008).
Cattaneo, E. et al., "Normal Huntington Function: An Alternative Approach to Huntington's Disease," *Nature Reviews: Neuroscience*, 6, pp. 919-930 (Dec. 2005).
Carter, R. et al., "Characterization of Progressive Motor Deficits in Mice Transgenic for the Human Huntington's Disease Mutation," *The Journal of Neuroscience*, 19(8), pp. 3248-3257 (Apr. 1999).
Certain STN chemicals, entry date ranging from Nov. 6, 2000 to May 19, 2009.
Cha, J. et al., "Altered Brain Neurotransmitter Receptors in Transgenic Mice Expressing a Portion of an Abnormal Human Huntington Disease Gene," *Proc. Natl. Acad. Sci. USA*, 95, pp. 6480-6485 (May 1998).
Cha, J., "Transcriptional Dysregulation in Huntington's Disease," *TINS*, 23(9), pp. 387-392 (Sep. 2000).
Chakraborti, A. et al., "Lithium Bromide, an Inexpensive and Efficient Catalyst for Opening of Epoxide Rings by Amines at Room Temperature under Solvent-Free Condition," *Eur. J. Org. Chem.*, 2004(17), pp. 3597-3600 (Sep. 2004).
Cimini et al., "Expression of Peroxisome Proliferator-Activated Receptors (PPARs) and Retinoic Acid Receptors (RXRs) in Rat Cortical Neurons.", Neuroscience, vol. 130, pp. 325-337, 2005.
Davies, S. et al., "Formation of Neuronal Intranuclear Inclusions Underlies the Neurological Dysfunction in Mice Transgenic for the HD Mutation," *Cell*, 90, pp. 537-548 (Aug. 1997).
DeJesus-Cortes, H. et al., "Neuroprotective Efficacy of Aminopropyl Carbazoles in a Mouse Model of Parkinson Disease" *PNAS*, vol. 109, No. 42, pp. 17010-17015 (Oct. 16, 2012).
Distelmaier, F. et al., "Life Cell Quantification of Mitochondrial Membrane Potential at the Single Organelle Level," *Cytometry A*, 73(2), pp. 129-138 (Feb. 2008).
Di Santo, R. et al., "Design, Synthesis and QSAR Studies on N-Aryl Heteroarylisopropanolamines, a New Class of Non-Peptidic HIV-1 Protease Inhibitors," *Bioorganic & Medicinal Chemistry*, 10(8), pp. 2511-2526 (Aug. 2002).
Doody, R. et al., "Effect of Dimebon on Cognition, Activities of Daily Living, Behaviour, and Global Function in Patients with Mild-to-Moderate Alzheimer's Disease: A Randomised, Double-Blind, Placebo-Controlled Study," *The Lancet*, 372, pp. 207-215 (Jul. 2008).
Doody, R. et al., "Intermittent Preventive Antimalarial Treatment in Infancy," *The Lancet*, 372, pp. 1383-1384 (Oct. 2008).
Dow, R. et al., "Identification of Tricyclic Analogs Related to Ellagic Acid as Potent/Selective Tyrosine Protein Kinase Inhibitors," *J. Med. Chem.*, 37(14), pp. 2224-2231 (Jul. 1994).
Driscoll, I. et al., "The Aging Hippocampus: A Multi-Level Analysis in the Rat," *Neuroscience*, 139(4), pp. 1173-1185 (Mar. 2006).

Enyedy et al., "Discovery of Small-Molecule Inhibitors of Bcl-2 through Structure-Based Computer Screening," *J. Med. Chem.*, 44(25), pp. 4313-4324 (Dec. 6, 2001).
Eriksson, P. et al., "Neurogenesis in the Adult Human Hippocampus," *Nature Medicine*, 4(11), pp. 1313-1317 (Nov. 1998).
Fedele, V. et al., "Neurogenesis in the R6/2 Mouse Model of Huntington's Disease is Impaired at the Level of Neurod1," *Neuroscience*, 173, pp. 76-81 (Jan. 2011).
Fernandes, H. et al., "Mitochondrial Sensitivity and Altered Calcium Handling Underlie Enhanced NMDA-Induced Apoptosis in YAC128 Model of Huntington's Diase," *The Journal of Neuroscience*, 27(50), pp. 13614-13623 (Dec. 2007).
Ferris, R.M. et al., "Rimcazole (BW 234U), a Novel Antipsychotic Agent Whose Mechanism of Action Cannot be Explained by a Direct Blockade of Postsynaptic Dopaminergic Receptors in Brain," *Drug Development Research*, 9(3), pp. 171-188 (Nov. 1986).
Freireich, E. et al., "Quantitative Comparison of Toxicity of Anticancer Agents in Mouse, Rat, Hamster, Dog, Monkey, and Man," *Cancer Chemotherapy Reports*, 50(4), pp. 219-244 (May 1966).
Gennaro, A. et al., "Remington's Pharmaceutical Sciences," *Mack Publishing Company*, $17^{th}$ Edition, pp. 1418-1419 (1985).
Getautis, V. et al., "Study of the Products from Reaction of 1(2)-Aminoanthraquinones with 1-Chloro-2,3-Epoxypropane," *Chemistry of Heterocyclic Compounds*, 41(4), pp. 426-436 (Apr. 2005).
Giancaspro et al., "Synthesis of Disubstituted Tetrahydrocarbazoles with Potential Antidepressive Activity," IL Farmaco, 44(5), 483-493, 1989.
Giancaspro et al., "Trypanocidal Activity of 1,2,3,4-Tetrahydrocarbazoles," Rev. Microbiol., Sao Paulo, 25(3):201-205, 1994.
Gil, J. et al., "Asialoerythropoetin is not Effective in the R6/2 Line of Huntington's Disease Mice," *BMC Neuroscience*, 5(17), pp. 1-10 (May 2004).
Gil, J. et al., "Reduced Hippocampal Neurogenesis in R6/2 Transgenic Huntington's Disease Mice," *Neurobiology of Disease*, 20, pp. 744-751 (Jun. 2005).
Gil, J. et al., "The R6 Lines of Transgenic Mice: A Model for Screening New Therapies for Huntington's Disease," *Brain Research Reviews*, 59(2), pp. 410-431 (Mar. 2009).
Godin, J. et al., "Huntingtin is Required for Mitotic Spindle Orientation and Mammalian Neurogenesis," *Neuron*, 67, pp. 392-406 (Aug. 2010).
Goehler, H. et al., "A Protein Interaction Network links GIT1, an Enhancer of Huntingtin Aggregation, to Huntington's Disease," *Molecular Cell*, 15, pp. 853-865 (Sep. 2004).
Goldberg, Y.P. et al., "Cleavage of Huntingtin by Apopain, a Proapoptotic Cysteine Protease, is Modulated by the Poyglutamine Tract," *Nature Genetics*, 13, pp. 442-449 (Aug. 1996).
Goldman, S. et al., "Neuronal Production, Migration, and Differentiation in a Vocal Control Nucleus of the Adult Female Canary Brain," *Proc. Natl. Acad. Sci. USA*, 80, pp. 2390-2394 (Apr. 1983).
Gross, C. "Neurogenesis in the Adult Brain: Death of a Dogma," *Nature Reviews*, 1, pp. 67-73 (Oct. 2000).
Haggquist, G. et al., "Intramolecular Triplet Energy Transfer. 3. A Carbazole-Naphthalene System Having Short Chain Length Methylene Spacer Units," *J. Phys. Chem.*, 97, pp. 9270-9273 (Sep. 1993).
Harbert, C. et al., "Neuroleptic Activity in 5-Aryltetrahydro-γ-carbolises," *J. Med. Chem.*, 23(6), pp. 635-643 (Jun. 1980).
Hisada, K. et al., "Intramolecular Triplet Energy Transfer. 4. A Carbazole-Naphthalene System Having a Flexible Alkyl Spacer Doped in Poly(methyl methacrylate) Matrixes," *J. Phys. Chem. B*, 102, pp. 2640-2645 (Mar. 1998).
Jackson-Lewis, V. et al., "Protocol for the MPTP Mouse Model of Parkinson's Disease," *Nature Protocols*, 2, pp. 141-151 (Feb. 2007).
Jin, K. et al., "Heparin-Binding Epidermal Growth Factor-Like Growth Factor: Hypoxia-Inducible Expresstion In Vitro and Stimulation of Neurogenesis In Vitro and In Vivo," *The Journal of Neuroscience*, vol. 22, Chapter 13, pp. 5365-5373 (Jul. 1, 2002).
Jorapur, Y. et al., "Potassium Carbonate as a Base for the N-alkylation of Indole and Pyrrole in Ionic Liquids," *Tetrahedron Letters*, 47(14), pp. 2435-2438 (Apr. 2006).

(56) References Cited

OTHER PUBLICATIONS

Jun, W. et al., "Inorganic-Organic Hybrid Photorefractive Materials Bearing the Bifunctional Chromophore," *Journal of Nonlinear Optical Physics & Materials*, 14(4), pp. 497-504 (Dec. 2005).
Kaewtong, C. et al., "Self-Assembly and Electrochemical Oxidation of Pollyamidoamine—Carbazole Dendron Surfmer Complexes: Nanoring Formation," *ACS Nano*, 2(8), pp. 1533-1542 (Aug. 2008).
Kamal et al., "Carbazole-pyrrolo [2,1-c] [1, 4] benzodiazepine conjugates: design, synthesis, and biological evaluation", MedChemComm, vol. 2, No. 8, pp. 780-788 (2001).
Kamnasaran, D. et al., "Disruption of the Neuronal PAS3 Gene in a Family Affected with Schizophrenia," *J. Med. Genet.*, 40(5), pp. 325-332 (May 2003).
Kamogawa, H. et al., "Syntheses of *N*-Substituted Carbazoles Involving Polymerizable Terminal Vinyl Groups," *Journal of Polymer Science*, 17(1), pp. 9-18 (Jan. 1979).
Kemp et al., "Pharmacologic Rescue of Motor and Sensory Function by the Neuroprotective Compound P7C3 Following Neonatal Nerve Injury," Neuroscience (2015), 284, 202-216.
Kempermann, G. et al., "More Hippocampal Neurons in Adult Mice Living in an Enriched Environment," *Nature*, 386, pp. 493-495 (Apr. 1997).
Kim, J et al., "Mitochondrial Loss, Dysfunction and Altered Dynamics in Huntington's Disease," *Human Molecular Genetics*, 19(20), pp. 3919-3935 (Jul. 2010).
Kim, S. et al., "Treadmill Exercise Prevents Aging-Induced Failure of Memory through an Increase in Neurogenesis and Suppression of Apoptosis in Rat Hippocampus," *Experimental Gerontology*, 45(5), pp. 357-365 (May 2010).
Kim, T. et al., "Molecular Tripods Showing Fluorescence Enhancement upon Binding to Streptavidin," *Organic Letters*, 7(1), pp. 111-114 (Jan. 2005).
Kim, T. et al., "Self-Quenching Mechanism: the Influence of Quencher and Spacer on Quencher-fluorescein Probes," *Bull. Korean. Chem. Soc.*, 28(7), pp. 1221-1223 (2007).
Kohl, Z. et al., "Impaired Adult Olfactory Bulb Neurogenesis in the R6/2 Mouse Model of Huntington's Disease," *BMC Neuroscience*, 11, pp. 1-11 (Sep. 2010).
Kondratov et al., "Small molecules that dramatically alter multidrug resistance phenotype by modulating the substrate specificity of P-glycoprotein," Proceedings of the National Academy of Sciences of the United States of America (2001), 98(24), 14078-14083.
Krishnan, V. et al., "The Molecular Neurobiology of Depression," *Nature*, 455, pp. 894-902 (Oct. 2008).
Kuhn, G. et al., "Neurogenesis in the Dentate Gyms of the Adult Rat: Age-Related Decrease of Neuronal Progenitor Proliferation," *The Journal of Neuroscience*, 16(6), pp. 2027-2033 (Mar. 1996).
Landree et al., "C75, a Fatty Acid Synthase Inhibitor, Modulates AMP-activated Protein Kinase to Alter Neuronal Energy Metabolism" *J. Biol. Chem.*, 2004, v. 279, p. 3817-3827 (Jan. 30, 2004).
Lavedan, C. et al., "Effect of a Ciliary Neurotrophic Factor Polymorphism on Schizophrenia Symptom Improvement in an Iloperidone Clinical Trial," *Pharmacogenomics*, 9(3), pp. 289-301 (Mar. 2008).
Lavedan, C. et al., "Association of the *NPAS3* Gene and Five Other Loci with Response to the Antipsychotic Iloperidone Identified in a Whole Genome Association Study," *Molecular Psychiatry*, 14(8), pp. 804-819 (Aug. 2009).
Lee, H. et al., "Structure-Activity Relationship Studies of the Chromosome Segregation Inhibitor, Incentrom A," *Bioorganic & Medicinal Chemistry Letters*, 18(6), pp. 4670-4674 (Aug. 2008).
Li, Z. et al., "Two Types of Nonlinear Optical Polyurethanes Containing the Same Isolation Groups: Syntheses, Optical Properties, and Influence of Binding Mode," *J. Phys. Chem. B*, 113, pp. 14943-14949 (Oct. 2009).
Lione, L. et al., "Selective Discrimination Learning Impairments in Mice Expressing the Human Huntington's Disease Mutation," *The Journal of Neuroscience*, 19(23), pp. 10428-10437 (Dec. 1999).
Liu, X. et al., "Induction of Apoptotic Program in Cell-Free Extracts: Requirement for dATP and Cytochrome c," *Cell*, 86, pp. 147-157 (Jul. 1996).
Liu et al., "Synthesis and Spectroscopic and Electrochemical Properties of TTF-Derivatized Polycarbazole", Macromolecules, vol. 41, No. 6, pp. 2045-2048 (2011).
Loo, D. et al., "Apoptosis is Inducted by β-Amyloid in Cultured Central Nervous System Neurons," *Proc. Natl. Acad. Sci. USA*, 90, pp. 7951-7955 (Sep. 1993).
Lygaitis, R. et al., "Synthesis and Photophysical Properties of Bipolar Low-Molar-Mass Amorphous Materials," *Journal of Photochemistry and Photobiology A: Chemistry*, 167(2-3), pp. 163-168 (Oct. 2004).
MacMillan, et al., "Development of Proneurogenic, Neuroprotective Small Molecules", Journal of the American Chemical Society, vol. 133, No. 5, pp. 1428-1437 (2011).
Maegawa, Y. et al., "A Useful Procedure for Diiodination of Carbazoles and Subsequent Efficient Transformation to Novel 3,6-bis(triethoxysilyl) Carbazoles Giving Mesoporous Materials," *Tetrahedron Letters*, 47(39), pp. 6957-6960 (Sep. 2006).
Mahapatra, et al., "A Small Molecule Which Protects Newborn Neurons", ACS Chemical Neuroscience, vol. 1, No. 9, pp. 589 (2010).
Mangialasche, F. et al., "Alzheimer's Disease: Clinical Trials and Drug Development," *The Lancet*, 9, pp. 702-716 (Jul. 2010).
Mangiarini, L. et al., "Exon 1 of the *HD* Gene with an Expanded CAG Repeat is Sufficient to Cause a Progressive Neurological Phenotype in Transgenic Mice," *Cell*, 87, pp. 493-506 (Nov. 1996).
Martin, D. et al., "Apoptotic Changes in the Aged Brain are Triggered by Interleukin-1β-Induced Activation of p38 and Reversed by Treatment with Eicosapentaeonic Acid," *The Journal of Biological Chemistry*, 277(37), pp. 34239-34246 (Sep. 2002).
Mattos et al., "Multiple Binding Modes," in *3D QSAR in Drug Design: Theory, Methods and Applications*, ed. H. Kubinyi, Springer, pp. 243-244 (Dec. 31, 1993).
McGrath, J. et al., "Novel Carbazole Phenoxy-Based Methacrylates to Produce High-Refractive Index Polymers," *Polymer*, 47, pp. 4042-4057 (Mar. 2006).
Menalled, L. et al., "Mouse Models of Huntington's Disease," *TRENDS in Pharmacological Sciences*, 23(1), pp. 32-39 (Jan. 2002).
Morcuende, A. et al., "Microwave-Promoted Transformations: Fast and Chemoselective N-Acylation of Amino Alcohols Using Catalytic Amounts of Dibutyltin Oxide. Influence of the Power Output and the Nature of the Acylating Agent on the Selectivity," *J. Org. Chem.*, 61(16), pp. 5264-5270 (Aug. 1996).
Murphy, K. et al., "Abnormal Synaptic Plasticity and Impaired Spatial Cognition in Mice Transgenic for Exon 1 of the Human Huntington's Disease Mutation," *The Journal of Neuroscience*, 20(13), pp. 5115-5123 (Jul. 2000).
Muruganantham et al., "Synthesis, anticonvulsant and antihypertensive activities of 8-substituted quinoline derivatives," Vel's College of Pharmacy, Biological & Pharmaceutical Bulletin. 27(10):1683-7 (2004).
Naidoo, J. et al., "Development of a Scalable Synthesis of P7C3-A20, a Potent Neuroprotective Agent" *Tetrahedron Letters*, vol. 54, pp. 4429-4431 (2013).
Naumova et al., CAPLUS Abstract of: Vestsi Akademii Navuk BSSR, Seryya Khimichnykh Navuk (1988), (4), 110-111)).
Negrin, C.M. et al., "In Vivo-In Vitro Study of Biodegradable Methadone Delivery Systems," *Biomaterials*, 22(6), pp. 563-570 (Mar. 2001).
Neitzert, H.C. et al., "Monitoring of the Initial Degradation of Oxadiazole Based Blue OLED's," *Journal of Non-Crystalline Solids*, 352, pp. 1695-1699 (Mar. 2006).
Nucifora, Jr., F. et al., "Interference by Huntingtin and Atrophin-1 with CBP-Mediated Transcription Leading to Cellular Toxicity," *Science*, 291, pp. 2423-2428 (Mar. 2001).
O'Brien, J. "A Promising New Treatment for Alzheimer's Disease?" *The Lancet*, 7, pp. 768-769 (Sep. 2008).
Okumura, H. et al., "Phenothiazine and Carbazole-Related Compounds Inhibit Mitotic Kinesin Eg5 and Trigger Apoptosis in Transformed Culture Cells," *Toxicology Letters*, 166(1), pp. 44-52 (Sep. 2006).

(56) References Cited

OTHER PUBLICATIONS

Olla, S. et al., "Indolyl-Pyrrolone as a New Scaffold for Pim1 Inhibitors," *Bioorganic & Medical Chemistry Letters*, 19(5), pp. 1512-1516 (Mar. 2009).
Pan, J. et al., "Synthesis of Carrier-Transporting Dendrimers with Perylenebis(dicarboximide)s as a Luminescent Core," *Eur. J. Org. Chem.*, 2006(4) pp. 986-1001 (Feb. 2006).
Panov, A. et al., "Early Mitochondrial Calcium Defects in Huntington's Disease are a Direct Effect of Polyglutamines," *Nature Neuroscience*, 5(8), pp. 731-736 (Aug. 2002).
Park, K. et al., "Promoting Axon Regeneration in the Adult CNS by Modulation of the PTEN/mTOR Pathway," *Science*, 322, pp. 963-966 (Nov. 2008).
Paton, J. et al., "Neurons Generated in the Adult Brain Are Recruited into Functional Circuits," *Science*, 225(4666), pp. 1046-1048 (Sep. 1984).
Pattison, L. et al., "Apoptotic Cascades as Possible Targets for Inhibiting Cell Death in Huntington's Disease," *J Neurol*, 253(9), pp. 1137-1142 (Sep. 2006).
Perutz, M., "Glutamine Repeats and Neurodegenerative Diseases: Molecular Aspects," *TIBS*, 24, pp. 58-63 (Feb. 1999).
Petit, S. et al., "Structure-Activity Relationship Analysis of the Peptide Deformylase Inhibitor 5-Bromo-1*H*-indole-3-acetohydroxamic Acid," *ChemMedChem*, 4(2), pp. 261-275 (Feb. 2009).
Petruska, J. et al., "Analysis of Strand Slippage in DNA Polymerase Expansions of CAG/CTG Triplet Repeats Associated with Neurodegenerative Disease," *The Journal of Biological Chemistry*, 273(9), pp. 5204-5210 (Feb. 1998).
Phillips, W. et al., "Abnormalities of Neurogenesis in the R6/2 Mouse Model of Huntington's Disease are Attributable to the In Vivo Microenvironment," *The Journal of Neuroscience*, 25(50), pp. 11564-11576 (Dec. 2005).
Pickard, B. et al., "Disruption of a Brain Transcription Factor, NPAS3, is Associated with Schizophrenia and Learning Disability," *American Journal of Medical Genetics Part B*, 136B(1), pp. 26-32 (Jul. 2005).
Pickard, B. et al., "The *NPAS3* Gene—Emerging Evidence for a Role in Psychiatric Illness," *Annals of Medicine*, 38(6), pp. 439-448 (2006).
Pickard, B. et al., "Interacting Haplotypes at the *NPAS3* Locus Alter Risk of Schizophrenia and Bipolar Disorder," *Molecular Psychiatry*, 14(9), pp. 874-884 (Sep. 2009).
Pieper, A. et al., "The Neuronal PAS Domain Protein 3 Transcription Factor Controls FGF-Mediated Adult Hippocampal Neurogenesis in Mice," *PNAS*, 102(39), pp. 14052-14057 (Sep. 2005).
Pieper, A. et al., "Discovery of a Proneurogenic, Neuroprotective Chemical," *Cell*, 142, pp. 39-51 (Jul. 2010).
Pieper et al., "P7C3 and an unbiased Approach to Drug Discovery for Neurodegenerative Diseases," *Chem. Soc. Rev.*(2014), 19: 51-59.
Poesen, K. et al., "Novel Role for Vascular Endothelial Growth Factor (VEGF) Receptor-1 and its Ligand VEGF-B in Motor Neuron Degeneration," *The Journal of Neuroscience*, 28(42), pp. 10451-10459 (Oct. 2008).
Ponce, M. et al., "Synthesis and Isolation of Bromo-β-Carbolines Obtained by Bromination of β-Carboline Alkaloids," *J. Heterocyclic Chem.*, 38, pp. 1087-1095 (Sep.-Oct. 2001).
Pubchem SID 3976298 (deposit date Aug. 9, 2005).
Pubchem SID 7706058 (deposit date Sep. 26, 2005).
PubChem compound N-{4-[3-(3,6-dibromo-9H-carbazol-9-yl)-2-hydroxypropoxy]phenyl} acetamide, create date Sep. 15, 2005.
Racke et al., PPARs in Neuroinflammation, Hindawi Publishing (Special Issue), 107 pgs., 2008.
Ramamoorthy, "Synthesis of small molecular inhibitors targeting signal transduction pathways," *University of South Florida Thesis*, pp. 1-70 (Jun. 10, 2009).
Raoul, C et al., "Motoneuron Death Triggered by a Specific Pathway Downstream of Fas: Potentiation by ALS-Linked SOD1 Mutations" *Neuron*, vol. 35, pp. 1067-1083 (Sep. 12, 2002).

Ravlee et al., "Pharmacological evaluation of some new 6-amino/methyl pyridine derivatives," *Chem. Pharm. Bull.* 51(2): 162-170 (2003).
Rische, T. et al., "One-Pot Synthesis of Pharmacologically Active Diamines via Rhodium-Catalysed Carbonylative Hydroaminomethylation of Heterocyclic Allylic Amines," *Tetrahedron*, 55(32), pp. 9801-9816 (Aug. 1999).
Rubinsztein, D., "Lessons from Animal Models of Huntington's Disease," *TRENDS in Genetics*, 18(4), pp. 202-209 (Apr. 2002).
Rubinsztein, D. et al., "Huntington's Disease: Molecular Basis of Neurodegeneration," *Expert Reviews in Molecular Medicine*, 5(22), pp. 1-21 (Aug. 2003).
Sadri-Vakili, G. et al., "Mechanisms of Disease: Histone Modifications in Huntington's Disease," *Nature Clinical Practice: Neurology*, 2(6), pp. 330-338 (Jun. 2006).
Schmidt, H. et al., "The Role of Neurotrophic Factors in Adult Hippocampal Neurogenesis, Antidepressant Treatments and Animal Models of Depressive-Like Behavior," *Behavioural Pharmacology*, 18(5-6), pp. 391-418 (Sep. 2007).
Stanfield, B. et al., "The Development of the Hippocampal Region," *Cerebral Cortex* (ed. Alan Peters and Edward G. Gones), vol. 7, pp. 91-131 (1988).
STN Registry Entry 312599-43-2 entered Jan. 3, 2001.
Sun, W. et al., "Programmed Cell Death of Adult-Generated Hippocampal Neurons is Mediated by the Proapoptotic Gene Bax," *The Journal of Neuroscience*, 24(49), pp. 11205-11213 (Dec. 2004).
Sundararajan, C. et al., "Photolytic Release of Carboxylic Acids Using Linked Donor-Acceptor Molecules: Direct versus Mediated Photoinduced Electron Transfer to *N*-Alkyl-4-picolinium Esters," *Organic Letters*, 7(13), pp. 2631-2634 (Jun. 2005).
Suzdalev, K.F. et al., "Synthesis of Indole 2,3-Epoxypropyl Derivatives and their Reactions with Amines," *Russian Journal of Organic Chemistry*, 41(2), pp. 233-237 (Feb. 2005).
Tang, T-S et al., "Disturbed $Ca^{2+}$ Signaling and Apoptosis of Medium Spiny Neurons in Huntington's Disease," *PNAS*, 102(7), pp. 2602-2607 (Feb. 2005).
Tatton, N.A. et al., "In Situ Detection of Apoptotic Nuclei in the Substantia Nigra Compacta of 1-methyl-4-phenyl-1,2,3,6-tetrahydropyridine-treated Mice Using Terminal Deoxynucleotidyl Transferase Labelling and Acridine Orange Staining," *Neuroscience*, 77(4), pp. 1037-1048 (Apr. 1997).
Teles, A.V.F.F. et al., "Increase in *Bax* Expression and Apoptosis are Associated in Huntington's Disease Progression," *Neuroscience Letters*, 438(1), pp. 59-63 (Jun. 2008).
Terfloth et al., "Electronic Screening. Lead Finding from Database Mining," in *The Practice of Medicinal Chemistry*, ed. C. Wermuth, Academic Press, pp. 131-157 (Mar. 7, 1996).
Tesla, R. et al., "Neuroprotective Efficacy of Aminopropyl Carbazoles in a Mouse Model of Amyotrophic Lateral Sclerosis" *PNAS*, vol. 109, No. 42, pp. 17016-17021 (Oct. 16, 2012).
Thiel, M. et al., "Contributions to the Development of Psychotropic Substances, 3 Mitt: Diphenylamine Derivatives with Pyridyl-substituted Side Chains and Guanidyl," *Chemical Monthly*, 93(5), pp. 1080-1089 (1962).
van Praag, H. et al., "Running Increases Cell Proliferation and Neurogenesis in the Adult Mouse Dentate Gyms," *Nature Neuroscience*, 2(3), pp. 266-270 (Mar. 1999).
Wang et al., "P7C3 Neuroprotective Chemicals Function by Activating the Rate-Limiting Enzyme in NAD Salvage," Cell 158, 11324-1334 (2014).
Wanker, E. et al., "HIP-I: A Huntingtin Interacting Protein Isolated by the Yeast Two-Hybrid System," *Human Molecular Genetics*, 6(3), pp. 487-495 (Mar. 1997).
Watanabe, T. et al., "Palladium-Catalyzed Direct Synthesis of Carbazoles via One-Pot *N*-Arylation and Oxidative Biaryl Coupling: Synthesis and Mechanistic Study," *J. Org. Chem.*, 74, pp. 4720-4726 (Jul. 2009).
Weissman, S. et al., "Ligand-Free Palladium-Catalyzed Cyanation of Aryl Halids," *J. Org. Chem.*, 70(4), pp. 1508-1510 (Jan. 2005).
Wermuth, C., "Molecular Variations Based on Isosteric Replacements," *The Practice of Medicinal Chemistry* (ed. Camille G. Wermuth), pp. 203-237 (1996).

(56) References Cited

OTHER PUBLICATIONS

Wilde, R. et al., "Acyl CoA:Cholesterol Acyltransferase (ACAT) Inhibitors: Heterocyclic Bioisosteres for the Urea Group in DuP 128," *Bioorganic & Medicinal Chemistry Letters*, 5(2), pp. 177-180 (Jan. 1995).
Wilen, S., *Tables of Resolving Agents and Optical Resolutions* (Ed. Ernest L. Eliel) pp. 268-298 (1972).
Wilen, S. et al, "Strategies in Optical Resolutions," *Tetrahedron*, 33, pp. 2725-2736 (1977).
Xuan, A.G. et al., "BDNF Improves the Effects of Neural Stem Cells on the Rat Model of Alzheimer's Disease with Unilateral Lesion of Fimbria-Fornix," *Neuroscience Letters*, 400(3), pp. 331-335 (Aug. 2008).
Xue, Y. et al., "Novel Hypoglycemic Compounds-synthesis of Glycine Derivatives and Research on the Role of PPARS," *Jiefangjun Yaoxue Xueao*, 25(1), pp. 5-10 (2009).
Yang, J. et al., "Prevention of Apoptosis by Bcl-2: Release of Cytochrome c from Mitochondria Blocked," *Science*, 275, pp. 1129-1132 (Feb. 1997).
Yin et al., "P7C3 Neuroprotective Chemicals Block Axonal Degeneration and Preserve Function after Traumatic Brain Injury" Cell Reports, 8, 1-10 (2014).
Yonemura, H. et al., "Spectroscopic Studies on Exchange Properties in Through-Ring Cyclodextrin Complexes of Carbazole-Viologen Linked Compounds: Effects of Spacer Chain Length," *J. Phys. Chem.*, 96, pp. 5765-5770 (Jul. 1992).
Yonemura, H. et al., "Effect of π-System on Long-Rang Photoinduced Electron Transfer in Through-Ring α-Cyclodextrin Complexes of Carbazole-Viologen Linked Compounds," *Tetrahedron Letters*, 39(38), pp. 6915-6918 (Sep. 1998).
Zeron, M. et al., "Mutant Huntingtin Enhances Excitotoxic Cell Death," *Molecular and Cellular Neuroscience*, 17(1), pp. 41-53 (Jan. 2001).
Zhang, H. et al., "Implantation of Neural Stem Cells Embedded in Hyaluronic Acid and Collagen Composite Conduit Promotes Regeneration in a Rabbit Facial Nerve Injury Model," *Journal of Translational Medicine*, 6(67), pp. 1-11 (Nov. 2008).
Zherebtsov et al., CAPLUS Abstract of: SU 474533, From: Otkrytiya, Izobret., Prom. Obraztsy, Tovarnye Znaki 1975, 52(23), 51-2.
Zoidis, G. et al., "Design and Synthesis of 1,2-annulated Adamantane Piperidines with Anti-Influenza Virus Activity," *Bioorganic & Medicinal Chemistry*, 17(4), pp. 1534-1541 (Feb. 2009).
Zuccato, C. et al., "Huntingtin Interacts with REST/NRSF to Modulate the Transcription of NRSE-controlled Neuronal Genes," *Nature Genetics*, 35(1), pp. 76-83 (Sep. 2003).
PCT International Search Report based on PCT/US2010/020681 dated Jun. 17, 2010.
USPTO Office Action in U.S. Appl. No. 12/832,056 mailed Feb. 9, 2012.
PCT International Search Report based on PCT/2011/043185 dated Apr. 10, 2012.
USPTO Office Action in U.S. Appl. No. 12/832,056 mailed Jul. 11, 2012.
USPTO Office Action in U.S. Appl. No. 12/685,652 mailed Jul. 19, 2012.
PCT International Search Report based on PCT/2012/052283 dated Oct. 24, 2012.
USPTO Notice of Allowance in U.S. Appl. No. 12/832,056 mailed Nov. 20, 2012.
USPTO Office Action in U.S. Appl. No. 12/685,652 mailed Mar. 20, 2013.
USPTO Office Action in U.S. Appl. No. 13/177,981 mailed Apr. 16, 2013.
USPTO Office Action in U.S. Appl. No. 12/685,652 mailed Apr. 26, 2013.
PCT International Preliminary Report on Patentability based on PCT/2011/043185 dated Jun. 25, 2013.
USPTO Office Action in U.S. Appl. No. 13/740,876 mailed Jul. 12, 2013.
USPTO Office Action in U.S. Appl. No. 13/709,531 mailed Jul. 17, 2013.
USPTO Office Action in U.S. Appl. No. 13/770,676 mailed Sep. 6, 2013.
USPTO Office Action in U.S. Appl. No. 13/177,981 mailed Nov. 18, 2013.
USPTO Office Action in U.S. Appl. No. 13/740,807 mailed Dec. 5, 2013.
USPTO Office Action in U.S. Appl. No. 13/594,223 mailed Jan. 13, 2014.
PCT International Search Report based on PCT/US13/56440 dated Jan. 22, 2014.
USPTO Office Action in U.S. Appl. No. 13/770,706 mailed Jan. 27, 2014.
USPTO Office Action in U.S. Appl. No. 13/177,981 mailed Mar. 21, 2014.
USPTO Office Action in U.S. Appl. No. 13/709,531 mailed Apr. 4, 2014.
Extended European Search Report issued in European Application No. EP 11804335 mailed on Apr. 17, 2014.
USPTO Office Action in U.S. Appl. No. 13/177,981 mailed Jun. 26, 2014.
USPTO Office Action in U.S. Appl. No. 13/594,223 mailed Jun. 26, 2014.
USPTO Office Action in U.S. Appl. No. 13/709,531 mailed Jul. 10, 2014.
PCT International Search Report based on PCT/US14/54099 dated Jan. 29, 2015.
USPTO Office Action in U.S. Appl. No. 14/100,515 mailed Feb. 12, 2015.
USPTO Office Action in U.S. Appl. No. 13/594,223 mailed Feb. 13, 2015.
PCT International Search Report based on PCT/US14/65058 dated Jan. 26, 2015.

* cited by examiner

Figure 11

NEUROPROTECTIVE CHEMICALS AND METHODS FOR IDENTIFYING AND USING SAME

CROSS-REFERENCE TO RELATED APPLICATIONS

This application claims the benefit of and priority to U.S. Provisional Patent Application Nos. 61/902,680 filed Nov. 11, 2013; 61/912,625 filed Dec. 6, 2013; and 61/993,328 filed May 15, 2014, and is a continuation-in-part of PCT/US14/65058 filed Nov. 11, 2014, the entire disclosures of all of which applications are hereby incorporated by reference.

STATEMENT REGARDING FEDERALLY SPONSORED RESEARCH

This invention was made with government support under Grant No. 5-R01-MH087986 awarded by the National Institute of Mental Health; the Government has certain rights in the invention.

FIELD

This disclosure relates to methods for identifying and using cell-protective (e.g., neuroprotective) compounds.

BACKGROUND

It is now accepted that the adult vertebrate brain fosters the birth and functional incorporation of newly formed neurons (Goldman and Nottebohm, Proc Natl Acad Sci USA 1983, 80: 2390-2394; Paton and Nottebohm, Science 1984, 225, 1046-1048; Burd and Nottebohm, J Comp Neurol 1985, 240: 143-152). However, it was long thought that no new neurons could be added to the adult mammalian brain. This dogma was challenged in the 1960's when autoradiographic evidence of new neuron formation in the hippocampal dentate gyrus, olfactory bulb, and cerebral cortex of the adult rat was presented (Altman, J. Science 1962, 135, 1127-1128; Altman, J. J Comp Neurol 1966, 128:431-474; Altman, Anat Rec 1963, 145:573-591; Altman and Das, J. Comp. Neurol. 1965, 124, 319-335; Altman and Das, J Comp Neurol 1966, 126: 337-390). It is now accepted that within all mammalian species, including humans (Eriksson et al., Nat. Med. 1998, 4(11), 1313-1317), there are two major reservoirs of neuronal stem cells, one located in the subgranular zone (SGZ) of the hippocampal dentate gyrus and another in the subventricular zone (SVZ) (Gross, Natl. Rev. 2000, 1, 67-72). Neural stem cells in the SVZ facilitate formation of new neurons that migrate rostrally to populate the olfactory bulb, while neural stem cells in the SGZ produce neurons that integrate locally in the granular layer of the dentate gyrus, a region of the hippocampus that exhibits lifelong structural and functional plasticity.

The process of new neuron formation in the adult mouse brain can be influenced by environmental, chemical and genetic variables. As demonstrated by Gage and colleagues, neurogenesis in the adult mouse brain is enhanced when animals are exposed to an enriched environment (Kempermann et al., Nature 1997, 386, 493-495) or able to exercise voluntarily (van Praag et al., Nat. Neuro-sci. 1999, 2, 266-270). More recently, anti-depressant drugs have been shown to enhance levels of adult neurogenesis in animals, including humans (Schmidt et al., Behav Pharmacol. 2007 September; 18(5-6):391-418; Boldrini et al., Neuropsychopharmacology 2009, 34, 2376-2389). Among many genes reported to impact adult neurogenesis is the gene encoding neuronal PAS domain protein 3 (NPAS3), a central nervous system (CNS)-specific transcription factor that has been associated with schizophrenia and bipolar disorder (Kamnasaran et al., J. Med. Genet. 2003, 40, 325-332; Pickard et al., Am. J. Med. Genet. B. Neuropsychiatr. Genet. 2005, 136B, 26-32; Pickard et al., Ann. Med. 2006, 38, 439-448; Pickard et al., Mol. Psychiatry 2009, 14, 874-884; Lavedan et al., *Pharmacogenomics* 2008, 9: 289-301). Animals missing both copies of the NPAS3 gene suffer a profound loss of adult hippocampal neurogenesis coupled with significant behavioral deficits (Pieper et al., Proc. Natl. Acad. Sci. USA 2005, 102, 14052-14057). Knowing that impaired post-natal neurogenesis elicits unfavorable phenotypic deficits, it is predicted that pro-neurogenic chemical compounds should exhibit favorable therapeutic benefits for a variety of neuropsychiatric and neurodegenerative diseases.

Neurodegenerative diseases currently affect millions of people worldwide, and the incidence of disease is rapidly increasing as the aging population expands. The magnitude and trend of this problem places a growing human and financial strain on healthcare systems, which is exacerbated by the absence of effective treatments for many of the most common afflictions. Neurodegenerative diseases, such as amyotrophic lateral sclerosis (ALS) and Parkinson's disease (PD), traumatic brain injury (PDI) and normal age-related cognitive decline, feature, by definition, neuronal cell death. Thus, there remains a great need for small molecules that could prevent the death of neurons in a variety of in vivo contexts. Such neuroprotective agents could possess general utility for treating disorders associated with neuron cell death.

SUMMARY

This disclosure relates generally to methods for identifying compounds that promote survival of cells and/or reduce cell death. In some embodiments, this disclosure relates to methods for identifying compounds that promote survival of existing neurons, reduce neuronal cell death, protect neurons from axonal degeneration, and/or promote neurogenesis (e.g., hippocampal neurogenesis) in the mammalian brain. For the purpose of simplicity these compounds are referred to as being neuroprotective. In certain embodiments, the compounds promote survival and integrity of neurons in the post-natal mammalian brain. In certain embodiments, the compounds are neuroprotective, that is, they promote the survival, health, integrity, growth, development and/or function of neurons, and/or protect neurons from cell death, apoptosis and/or degeneration, particularly CNS, brain, cerebral, and hippocampal neurons. In certain embodiments, the compounds stimulate post-natal hippocampal neurogenesis, reduce neuronal cell death, and/or protect neurons from axonal degeneration, which while not wishing to be bound by theory, is believed to represent a therapeutic target useful for treating a variety of diseases. Also included are compounds identified by such methods, and use of the compounds for the treatment of various diseases.

Provided herein, in one aspect, is a method for identifying a compound having cell-protective (e.g., neuroprotective) activity. The method includes: incubating a test compound with a nicotinamide phosphoribosyltransferase (NAMPT); and measuring an activity of the NAMPT; wherein an increase in the activity of the NAMPT compared to a control that is not incubated with the test compound is indicative of cell-protective (e.g., neuroprotective) activity of the test compound.

In some embodiments, in the incubating step, the NAMPT is recombinantly produced and optionally further purified. The NAMPT can be present at about 0.1 to about 10 μM, about 0.5 to about 5 μM, or about 1 μM. In certain embodiments, the test compound can be additionally incubated with nicotinamide, phosphoribosylpyrophosphate, alcohol dehydrogenase, nicotinamide mononucleotide adenylyl-transferase, and an alcohol (e.g., ethanol). In embodiments, the measuring step includes determining an amount of nicotinamide adenine dinucleotide reduced form (NADH) or nicotinamide mononucleotide (NMN), which can optionally be measured by ultra violet light, mass spectrometry or fluorescence, either directly or after suitable derivatization. In one example, the amount of NADH is measured by optical density 340 nm. In some embodiments, an increase in the amount of NADH is indicative of increased NAMPT activity. In embodiments, the test compound having said cell-protective (e.g., neuroprotective) activity can be further determined to bind and/or activate the NAMPT. In some examples, the method further includes determining that the test compound having said cell-protective (e.g., neuroprotective) activity binds and/or activates the NAMPT, e.g., by mass spec and/or gel electrophoresis.

A further aspect relates to another method for identifying a compound having cell-protective (e.g., neuroprotective) activity. The method includes: exposing a population of cells to a test compound and a DNA-damaging agent; and determining survival rate of the population of cells; wherein an increase in the survival rate compared to a control that is not treated with the test compound is indicative of cell-protective (e.g., neuroprotective) activity of the test compound.

In some embodiments, the exposing step comprises incubating the population of cells with the test compound and the DNA-damaging agent. In some alternative embodiments, the exposing step comprises incubating the population of cells with the test compound first, followed by the DNA-damaging agent. In yet other embodiments, the exposing step comprises incubating the population of cells with the DNA-damaging agent first, followed by the test compound. The DNA-damaging agent may activate poly-ADP-ribose polymerase (PARP), and/or lead to decline in nicotinamide adenine dinucleotide (NAD) level. In certain embodiments, the DNA-damaging agent is an anthracycline. The anthracycline can be one or more of daunorubicin, doxorubicin, epirubicin, idarubicin, valrubicin and/or mitoxantrone. In one example, the anthracycline is doxorubicin. The DNA-damaging agent (e.g., doxorubicin) can be provided at about 0.01-20 uM, or about 0.05-10 uM, or about 0.1-1.5 uM, or about 0.5 uM. The test compound can be provided at about 1-20 uM, or about 2-10 uM or about 5 uM. The test compound is a small molecule. In some embodiments, the cells are mammalian cells. In some embodiments, the test compound having said cell-protective (e.g., neuroprotective) activity can be determined to protect the cells from toxicity mediated by the DNA-damaging agent, and/or reduce apoptosis induced by the DNA-damaging agent. In certain embodiments, the test compound having said cell-protective (e.g., neuroprotective) activity can be determined to not protect the cells from toxicity induced by a toxin selected from the group consisting of bortezomib, staurosporine, taxol, brefeldin, cytochalasin D, TNFa and TRAIL.

The DNA-damaging agent based method, in some embodiments, further comprises incubating the test compound with nicotinamide phosphoribosyltransferase (NAMPT) and measuring an activity of the NAMPT, wherein an increase in the activity of the NAMPT additionally confirms the cell-protective (e.g., neuroprotective) activity of the test compound. In certain embodiments, the test compound having said cell-protective (e.g., neuroprotective) activity is determined to increase nicotinamide adenine dinucleotide (NAD) level, and/or enhance intracellular production of the NAD by increasing the activity of the NAMPT.

In some embodiments, the test compound having said cell-protective (e.g., neuroprotective) activity is determined to bind and/or activate the NAMPT. In some examples, the method further includes determining that the test compound having said cell-protective (e.g., neuroprotective) activity binds and/or activates the NAMPT, e.g., by mass spec and/or gel electrophoresis.

In another aspect, a compound having cell-protective (e.g., neuroprotective) activity, identified by the methods described herein is provided. In some embodiments, the compound can have a $\Delta$(Sinf−S0)/AC50 value greater than about 0, or greater than about 1, or greater than about 2, or greater than about 3, or greater than about 4, or greater than about 5, or greater than about 10, or greater than about 20, or greater than about 30, or greater than about 40, or greater than about 50, or greater than about 60, or greater than about 70, or greater than about 80, or greater than about 90, or greater than about 100. $\Delta$(Sinf−S0)/AC50 represents change in protection activity compared to vehicle control. Protection activity is expressed by (Sinf−S0)/AC50 in the twelve-point dose response curve (DRC) corresponding to each compound, wherein both efficacy and potency of compounds were considered. Sinf represents the expected maximal protection. S0 is the baseline level of toxicity associated with, for example, doxorubicin, in the absence of a protective compound. AC50 is the concentration of a compound where 50% of its maximal protection effect was observed.

In certain embodiments, the compounds can bind and/or activate nicotinamide phosphoribosyltransferase (NAMPT). The compounds may enhance an activity of NAMPT. The compounds may also enhance NAD levels compared to the control. In some embodiments, the compounds enhance intracellular production of NAD by agonizing or increasing an activity of NAMPT.

Also provided herein is a pharmaceutical composition comprising one or more of the compounds identified by the methods described herein, or a pharmaceutically acceptable salt thereof, and a pharmaceutically acceptable carrier.

In a further aspect, a method for the treatment of a disease, disorder, or condition associated with unwanted neuronal cell death is provided. The method includes administering an effective amount of one or more of the compounds identified by the methods described herein, or a pharmaceutically acceptable salt thereof, to a patient in need thereof. In some embodiments, the compound or salt enhances NAD levels.

In yet another aspect, a method for the treatment of a disease, disorder, or condition associated with unwanted neuronal cell death is provided, which includes administering an effective amount of one or more of the compounds described herein, or a pharmaceutically acceptable salt thereof, to a patient in need thereof, wherein the compound or salt binds NAMPT. In some embodiments, the compound or salt enhances NAD levels.

In yet another aspect, a method for the treatment of a disease, disorder, or condition associated with unwanted neuronal cell death is provided, which includes administering an effective amount of one or more of the compounds described herein, or a pharmaceutically acceptable salt thereof, to a patient in need thereof, wherein the compound or salt activates NAMPT. In some embodiments, the compound or salt enhances NAD levels.

In some embodiments, the disease, disorder, or condition is selected from: DNA-damaging agent (e.g., anthracycline) mediated cardiotoxicity, schizophrenia, major depression, bipolar disorder, normal aging, epilepsy, traumatic brain injury and/or a visual symptom associated therewith, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuro-active drug, retinal degeneration, spinal cord injury, peripheral nerve injury, physiological weight loss associated with various conditions, cognitive decline and/or general frailty associated with normal aging and/or chemotherapy, chemotherapy induced neuropathy, concussive injury, crush injury, peripheral neuropathy, diabetic neuropathy, post-traumatic headache, multiple sclerosis, retinal degeneration and dystrophy (such as Leber congenital amaurosis, retinitis pigmentosa, cone-rod dystrophy, microphthalmia, anophthalmia, myopia, and hyperopia), spinal cord injury, traumatic spinal cord injury, peripheral nerve injury (such as peripheral nerve crush injury, neonatal brachial plexus palsy, and traumatic facial nerve palsy), retinal neuronal death related diseases (such as glaucoma and age related macular degeneration, diabetic retinopathy, retinal blood vessel occlusions, retinal medication toxicity (such as what amino glycosides or plaquenil can cause), retinal trauma (e.g., post-surgical), retinal infections, choroidal dystrophies, retinal pigmentary retinopathies, inflammatory and cancer mediated auto immune diseases that result in retinal neuronal cell death), Autism, Stargardt disease, Kearns-Sayre syndrome, Pure neurosensory deafness, Hereditary hearing loss with retinal diseases, Hereditary hearing loss with system atrophies of the nervous system, Progressive spinal muscular atrophy, Progressive bulbar palsy, Primary lateral sclerosis, Hereditary forms of progressive muscular atrophy and spastic paraplegia, Frontotemporal dementia, Dementia with Lewy bodies, Corticobasal degeneration, Progressive supranuclear palsy, Prion disorders causing neurodegeneration, Multiple system atrophy (olivopontocerebellar atrophy), Hereditary spastic paraparesis, Friedreich ataxia, Non-Friedreich ataxia, Spinocerebellar atrophies, Amyloidoses, Metabolic-related (e.g., Diabetes) neurodegenerative disorders, Toxin-related neurodegenerative disorders, Multiple sclerosis, Charcot Marie Tooth, Diabetic neuropathy, Metabolic neuropathies, Endocrine neuropathies, Orthostatic hypotension, Creutzfeldt-Jacob Disease, Primary progressive aphasia, Frontotemporal Lobar Degeneration, Cortical blindness, Shy-Drager Syndrome (Multiple, System Atrophy with Orthostatic Hypotension), Diffuse cerebral cortical atrophy of non-Alzheimer type, Lewy-body dementia, Pick disease (lobar atrophy), Thalamic degeneration, Mesolimbocortical dementia of non-Alzheimer type, Nonhuntingtonian types of chorea and dementia, Cortical-striatal-spinal degeneration, Dementia-Parkinson-amyotrophic lateral sclerosis complex, Cerebrocerebellar degeneration, Cortico-basal ganglionic degeneration, Familial dementia with spastic paraparesis or myoclonus, and Tourette syndrome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) U2OS cells were treated with 5 µM P7C3-A20 for 2 h prior to incubation with the indicated concentrations of doxorubicin for 72 h. (FIG. 1B) Comparison of the P7C3-S243 enantiomers in protection of cells from doxorubicin revealed that (−)-P7C3-S243 was more active than (+)-P7C3-S243, consistent with their respective neuroprotective activities in vivo (see text). In all cell survival graphs, data are expressed as mean±standard deviation (SD) of experimental duplicates.

(FIG. 2A) Chemical structure of P7C3-S326. (FIG. 2B) Full gel image of photo-crosslinking in H2122 cells with P7C3-S326 followed by click chemistry with Alexa 532 dye. The active analog P7C3-A20 competed away the UV-dependent binding of p70 to P7C3-S326. (FIG. 2C) Formulas used for calculating doxorubicin toxicity (dox:tox) protection activity. Protection activity is expressed by (Sinf−S0)/AC50 in the twelve-point dose response curve (DRC) corresponding to each compound, wherein both efficacy and potency of compounds were considered. Sinf represents the expected maximal protection. S0 is the baseline. AC50 is the concentration of a compound where 50% of its maximal protection effect was observed. (FIG. 2D) Scatter plot of 168 derivatives of P7C3 revealed a significant correlation between protective activity of P7C3 analogs from doxorubicin-mediated toxicity and their ability to compete for photo-crosslinking of P7C3-S326 to p70. In the photo-crosslinking assays, the p70 band intensity was quantified by Image J, and compared the sample of P7C3-S326 alone with that of P7C3-S326 plus competitor. Pearson correlation coefficient (r) and two tailed P value were determined by GraphPad Prism 6 and Spearman Rank Correlation (v1.0.1) software.

FIGS. 3A-2D. Identification of p70 and p55 targets of P7C3 by two-dimensional gel electrophoresis and mass spectrometry. Lysates from cells exposed to 0.3 µM P7C3-S326 were CLICKed with a green dye, Alexa 532, and those from cells co-exposed to 0.3 µM P7C3-S326 and 5 µM of the active competitor P7C3-A20 were CLICKed with a red dye Cy5. CLICK reacted lysates were combined, subjected to two-dimensional gel electrophoresis, and scanned in the green channel (FIG. 3A) and the red channel (FIG. 3B). Images from both channels were merged to reveal green-only spots (FIG. 3C). After spot picking, total proteins were visualized by Sypro Ruby staining (FIG. 3D). White circles in (FIG. 3D) indicate spots excised for shotgun mass spectrometry analysis.

(FIG. 4A) CLICK reacted lysates from H2122 cells treated with P7C3-S326 were separated on a standard 8% SDS-PAGE gel (left panel) or one supplemented with 7M urea (right panel), and visualized on a Typhoon scanner. Asterisk indicates the crosslinked protein that migrates as 70KDa in a standard SDS-PAGE gel and 55KDa in the SDS-PAGE gel supplemented with 7M urea. (FIG. 4B) The same lysates were resolved on a horizontal urea gradient gel co-loaded with crosslinked p70 and the same 75 kD and 50 kD size standard proteins displayed in FIG. 4A. The horizontal urea gradient proceeds from zero denaturant on the left to 7M denaturant on the right.

(FIG. 5A) U2OS cells were treated with the indicated concentration of P7C3-A20. Cells were harvested and NAD metabolites were measured by LC-MS/MS. Abundance of NAD was normalized relative to total metabolites (Experimental Procedures). The data are represented as the mean±SD of experimental duplicates. (FIG. 5B) Active derivatives P7C3-A20 and P7C3-S243, but not inactive derivatives P7C3-S6, or P7C3-S117, facilitate replenishment of NAD levels in doxorubicin-treated cells. Cells were grown in 96-well plates and treated with the indicated concentrations of P7C3-A20, P7C3-S243, P7C3-S6 or P7C3-S117 together with 0.5 µM doxorubicin for 45 h. Cellular NAD abundance was determined by NAD/NADH Glo assay kit. (FIG. 5C) Scatter plots revealed a strong correlation between dox:tox protective activities of 159 compounds and their relative abilities to replenish NAD levels. The activities in both assays are represented by (Sinf−S0)/AC50 in dose response curves of test compounds.

(FIG. 6A) Cells were pre-treated with 0.5 µM doxorubicin for 48 hours, followed by 6 hours treatment with $^{14}$C-nicotinamide in the presence of the indicated amount of P7C3-A20. Metabolites were extracted and analyzed by thin layer chromatography. (FIG. 6B) Quantification of the relative intensities of NAD and NMN from the thin layer chromatogram.

(FIG. 7A) P7C3-A20 was incubated at indicated concentrations in a reaction coupled with three enzymes; NAMPT, NMNAT, and ADH (Experimental Procedures). NAMPT activity was recorded for the indicated period of time at OD340 nm by measuring NADH appearance, leading to the indicated concentration-time plot. Each assay was repeated three independent times with similar results. (FIG. 7B) Analysis of the activities of thirty P7C3 analogs was performed to assess their effects on NAMPT enzymatic activity. The reaction rate was calculated as the slope of the concentration-time curve. Relative reaction rate was normalized by the control reaction run prior to compound addition. Data represents the mean of experimental duplicates. Scatter graphs were plotted to compare the ability of compounds to activate NAMPT relative to their ability to compete away P7C3-S326 crosslinking (top scatter plot), ability to protect cells from doxorubicin-mediated toxicity (middle scatter plot), or ability to facilitate NAD restoration in doxorubicin-treated cells (bottom scatter plot). Significant correlations were observed from all three sets of data. (FIG. 7C) Comparison of P7C3-S243 enantiomers showed that (−)-P7C3-S243 was superior to (+)-P7C3-S243 in activating the purified NAMPT enzyme. Data are expressed as mean±SD of duplicate independent assays.

(FIG. 9A) U2OS cells were treated with increasing concentrations of P7C3-A20 for 2 h prior to exposure to 0.5 µM doxorubicin for another 2 h. Cells were harvested and subjected to western blotting with the DNA damage marker, γ-H2AX. Actin was served as loading control. (FIG. 9B) U2OS cells were treated with P7C3-A20 and doxorubicin for the indicated time. Caspase-3 activation was determined by western blotting. Caspase-3 cleavage was observed when treated with doxorubicin alone at 60 h, but was prevented in the presence of P7C3-A20.

FIG. 11. Competition for photo-crosslinking of P7C3-S326 to p70 of all tested compounds. Lysates from crosslinked cells exposed to 0.3 µM P7C3-S326 and 5 µM of various P7C3 derivatives were CLICKed with Alexa 532 and visualized on SDS-PAGE.

DETAILED DESCRIPTION

Figure 1:
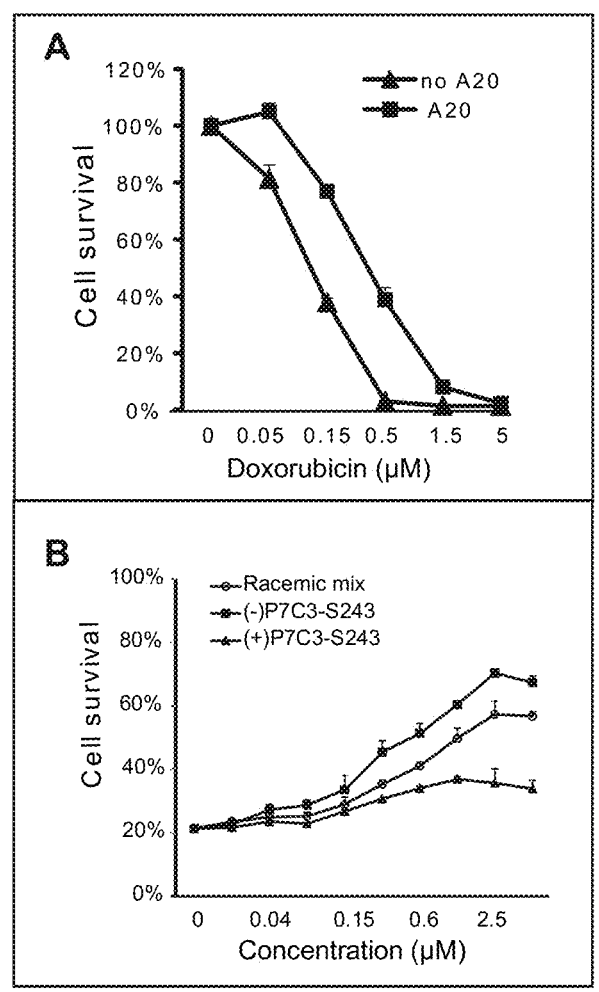
FIGS. 1A-1B. Protection of cultured U2OS cells from doxorubicin-mediated toxicity by active derivatives of P7C3.

A number of small molecules with in vivo neuroprotective properties have been previously identified and disclosed in U.S. Pat. No. 8,362,277; U.S. Publication No. 2011/0015217; U.S. Publication No. 2012/0022096 and U.S. Publication No. 2013/0040977; and U.S. application Ser. No. 14/339,772 filed Jul. 24, 2014, all of which are hereby incorporated herein by reference in their entirety, in particular the compounds disclosed in the Examples section. Additional compounds are disclosed in U.S. Provisional Patent Application No. 61/902,680 filed Nov. 11, 2013 and U.S. Provisional Patent Application No. 61/912,625 filed Dec. 6, 2013, all of which are hereby incorporated herein by reference in their entirety, in particular the compounds disclosed in the Examples section.

It has now been surprisingly discovered that the in vivo neuroprotective properties of these compounds coincide or correlate with their protective activity against DNA-damaging agent-mediated cell toxicity. Unexpectedly, such protection is observed with DNA-damaging agent such as anthracyclines but not with other potent toxins such as bortezomib, staurosporine, taxol, brefeldin, cytochalasin D, TNFα and TRAIL. As such, DNA-damaging agents can be used in a method to screen for or identify compounds having neuroprotective activity. More broadly, compounds having general cell-protective activity (as opposed neuron specific protection) to can also be identified using such methods. As demonstrated herein, non-neuron cells can be used in such methods, revealing a general protective activity of tested compounds of non-neuron cells from toxicity.

DNA-damaging agents are widely used in treatment of malignant conditions such as various cancer. However, they are also known to induce cardiac toxicity, especially dose-dependent cardiomyopathy. As such, compounds identified to have cell-protective activity against DNA-damaging agent (e.g., anthracycline) mediated toxicity can also be used to treat DNA-damaging agent (e.g., anthracycline) mediated cardiotoxicity. In some embodiments, such compounds can be administered along with, or subsequent to, DNA-damaging agent (e.g., anthracycline) administration.

Another surprising finding is that the compounds bind to and/or activate nicotinamide phosphoribosyltransferase (NAMPT). The compounds may enhance an activity of NAMPT. The compounds may also enhance nicotinamide adenine dinucleotide (NAD) levels. In some embodiments, the compounds enhance intracellular production of NAD by agonizing an activity of NAMPT. Thus, in addition to the cell-protective activities that render these compounds useful in treating diseases or conditions associated with, for example, unwanted cell death and/or insufficient cell production, they can also be used as potential treatments for generalized frailty typical of aged animals and humans, since NAD is an important coenzyme found in all living cells and is involved in numerous redox reactions in metabolism.

DEFINITIONS

Unless defined otherwise, all technical and scientific terms used herein have the meaning commonly understood by one of ordinary skill in the art to which the disclosure pertains. The Definitions section at paragraphs [1001]-[1031] of U.S. Publication No. 2013/0040977 is incorporated herein by reference. Specific terminology is defined below.

As used in the specification and the appended claims, the singular forms "a," "an," and "the" include plural referents unless the context clearly dictates otherwise.

As used herein, the term "about" means within 20%, more preferably within 10% and most preferably within 5%.

The terms "cell-protective" and "cell-protective activity" refer to an activity in promoting the survival, health, integrity, growth, development and/or function of a cell, and/or protecting a cell from cell death, apoptosis and/or degeneration, and/or stimulating generation, production, differentiation and/or multiplication.

The terms "neuroprotective" and "neuroprotective activity" refer to an activity in promoting the survival, health, integrity, growth, development and/or function of neurons, and/or protecting neurons from cell death, apoptosis and/or degeneration, and/or stimulating neurogenesis, particularly CNS, brain, cerebral, and hippocampal neurons.

The term "neurogenesis" refers to the process by which neurons are generated from neural stem cells and progenitor cells, which is responsible for populating the growing brain with neurons. While neurogenesis generally is most active during pre-natal development, in some embodiments the compounds disclosed herein can stimulate or promote post-natal neurogenesis such as hippocampal neurogenesis.

The terms "treating" and "treatment" as used herein refer to reduction in severity and/or frequency of symptoms, elimination of symptoms and/or underlying cause, and improvement or remediation of damage.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing and/or that it is included on the Inactive Ingredient Guide prepared by the U.S. Food and Drug administration.

As used herein, the term "patient" or "individual" or "subject" refers to any person or mammalian subject for whom or which therapy is desired, and generally refers to the recipient of the therapy to be practiced according to the disclosure.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atom therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo, straight chain or branched chain alkyl, alkenyl, alkynyl, cycloalkyl, aryl, heteroaryl, heterocyclyl, alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, alkyl, haloalkyl, alkenyl, alkynyl, cycloalkyl, cycloalkylalkyl, aryl, aralkyl, heterocyclyl, heterocyclylalkyl, heteroaryl or heteroarylalkyl. Unless otherwise noted, all groups described herein optionally contain one or more common substituents, to the extent permitted by valency.

Screening Methods

Aspects of the invention relate to screening methods for identifying a compound having cell-protective (e.g., neuroprotective) activity. These methods can be used in high-throughput screens of many compounds in parallel, e.g., at least 10 compounds, at least 50 compounds, at least 100 compounds, at least 500 compounds, at least 1000 compounds, at least 10,000 compounds, or more or less compounds.

In one aspect, a method for identifying a compound having cell-protective (e.g., neuroprotective) activity is based on the surprising discovery that certain compounds (e.g., the P7C3 class of compounds) are capable of activating nicotinamide phosphoribosyltransferase (NAMPT). The method can include: incubating a test compound with a NAMPT; and measuring an activity of the NAMPT; wherein an increase in the activity of the NAMPT compared to a control that is not incubated with the test compound is indicative of cell-protective (e.g., neuroprotective) activity of the test compound.

In some embodiments, the test compound can be provided at any suitable amount or concentration, e.g., about 0.1-20 uM, or about 0.3-5 uM, about 1 uM or about 3 uM, or any other suitable concentration one of ordinary skill can determine through routine experimentation depending on the specific compound. The test compound can be any compound or agent of interest. The test compound can be a small molecule (e.g., having a molecular weight less than 1000 Da). The test compound can be from a library. In one example, the test compound may be selected from the compounds listed in Table 1. The test compound can also be those disclosed in U.S. Pat. No. 8,362,277; U.S. Publication No. 2011/0015217; U.S. Publication No. 2012/0022096 and U.S. Publication No. 2013/0040977; U.S. application Ser. No. 14/339,772 filed Jul. 24, 2014; U.S. Provisional Patent Application No. 61/902,680 filed Nov. 11, 2013 and U.S. Provisional Patent Application No. 61/912,625 filed Dec. 6, 2013, all of which are hereby incorporated herein by reference in their entirety, in particular the compounds disclosed in the Examples section.

In some embodiments, the NAMPT can be recombinantly produced and optionally further purified. The NAMPT can be from a mammalian source such as human. Purified NAMPT is also commercially available. The NAMPT is present at about 0.1 to about 10 μM, about 0.5 to about 5 μM, or about 1 μM in the reaction mixture.

NAMPT activity can be measured by any suitable methods such as known immunometric, fluorometric and colorimetric assays (e.g., the CycLex® NAMPT Colorimetric Assay Kit by MBL International, and the assay described in Zhang et al., Anal. Biochem. 2011; 412(1):18-25 which is incorporated herein by reference in its entirety). In one example, NAMPT activity is measured by a coupled assay where the reaction mixture can further include nicotinamide, phosphoribosylpyrophosphate, alcohol dehydrogenase, nicotinamide mononucleotide adenylyl-transferase (NMNAT), and an alcohol. NAMPT can convert nicotinamide to nicotinamide mononucleotide (NMN), which is then converted to NAD by NMNAT. In turn, NAD is reduced to the reduced form, NADH, by alcohol dehydrogenase, using alcohol (e.g., ethanol) as a substrate. The amount of NADH can be monitored by ultra violet light (e.g., optical density (OD) 340 nm), mass spectrometry or fluorescence, either directly or after suitable derivatization. The amount of NADH reflects the activity of NAMPT. That is, the higher the amount of NADH, the higher the activity of NAMPT. In another example, an amount of NMN can be measured (e.g., in a reaction mixture containing NAMPT and nicotinamide, which can be measured by ultra violet light, mass spectrometry or fluorescence, either directly or after suitable derivatization.

In some embodiments, the test compound having said cell-protective (e.g., neuroprotective) activity can be further determined to bind and/or activate the NAMPT. Determining the test compound having said cell-protective (e.g., neuroprotective) activity binds and/or activates the NAMPT can be done by any suitable methods such as mass spec and/or gel electrophoresis.

In a further aspect, another method for identifying a compound having cell-protective (e.g., neuroprotective) activity is based on the surprising finding that certain compounds (e.g., the P7C3 class of compounds) are capable of protecting cells from the toxicity induced by DNA-damaging agents. The method can include: exposing a population of cells to a test compound and a DNA-damaging agent; and determining survival rate of the population of cells; wherein an increase in the survival rate compared to a control that is not treated with the test compound is indicative of cell-protective (e.g., neuroprotective) activity of the test compound.

In some embodiments, the exposing step includes incubating the population of cells with the test compound and the DNA-damaging agent at the same time (e.g., in the same reaction mixture for the same amount of time). Alternatively, the population of cells can be incubated with the test compound first (e.g., for a first period of time such as 0.5-5 hours, or about 1-3 hours, or about 2 hours, or any other suitable length one of ordinary skill can determine through routine experimentation depending on the specific cells or compound), followed by the DNA-damaging agent (e.g., for a second period of time such as about 5-200 hours, or about 10-100 hours, or about 72 hours, or any other suitable length one of ordinary skill can determine through routine experimentation depending on the specific cells or the DNA-damaging agent). In yet another embodiment, the population of cells are incubated with the DNA-damaging agent first (e.g., for the second period of time), followed by the test compound (e.g., for the first period of time).

In certain embodiments, the DNA-damaging agent can activate poly-ADP-ribose polymerase (PARP). PARP uses NAD as the donor for poly-ADP-ribose synthesis and hence lowers cellular levels of NAD. Introduction of the compounds disclosed herein (e.g., the P7C3 class), by increasing or replenishing NAD levels, thus can protect the cells from toxicity induced by the DNA-damaging agent, increase their general health, and in some embodiments extend the life span of the cells.

In some embodiments, the DNA-damaging agent can be an anthracycline. Anthracycline is a class of drugs used in cancer chemotherapy. Examples include daunorubicin, doxorubicin, epirubicin, idarubicin, valrubicin and/or mitoxantrone. Anthracyclines have several mechanisms of action, including inhibition of DNA and RNA synthesis by intercalating between base pairs of the DNA/RNA strand, thus preventing the replication of rapidly growing cancer cells; inhibition of topoisomerase II enzyme, preventing the relaxing of super-coiled DNA and thus blocking DNA transcription and replication; iron-mediated generation of free oxygen radicals that damage the DNA, proteins and cell membranes; and induction of histone eviction from chromatin that deregulates DNA damage response, epigenome and transcriptome. These all lead to toxicity to the cells, eventually cell death. The compounds disclosed herein (e.g., the P7C3 class) can mitigate and reverse the toxicity and/or cell death induced by anthracyclines. In one example, doxorubicin can be used as the DNA-damaging agent in the screen.

It has been surprisingly found that certain compounds having cell-protective (e.g., neuroprotective) activity (e.g., the P7C3 class) protect the cells from DNA-damaging agent (e.g., anthracycline) mediated toxicity, while failing to protect cells from toxicity induced by other powerful toxins such as bortezomib, staurosporine, taxol, brefeldin, cytochalasin D, TNFa and TRAIL. While without wishing to be bound by theory, it is hypothesized that because DNA-damaging agent (e.g., anthracycline) activates PARP which lowers cellular levels of NAD, cell-protective (e.g., neuroprotective) compounds can increase or replenish NAD levels, thereby protecting the cells from DNA-damaging agent (e.g., anthracycline) mediated toxicity, increasing the general health of the cells, and in some embodiments extending the life span of the cells.

Any cells can be used in the screen. As long as the cells contain DNA to be targeted by the DNA-damaging agent, they can be used to screen for compounds that mitigate or reverse toxicity mediated by the DNA-damaging agent. In some embodiments, the cells are mammalian cells. The cells can also be established cell lines commonly used in laboratory experiments.

In some embodiments, the test compound can be provided at any suitable amount or concentration, e.g., about 1-20 uM, or about 2-10 uM or about 5 uM, or any other suitable concentration one of ordinary skill can determine through routine experimentation depending on the specific cells or the compound. The test compound can be any compound or agent of interest. The test compound can be a small molecule (e.g., having a molecular weight less than 1000 Da). The test compound can be from a library. In one example, the test compound may be selected from the compounds listed in Table 1. The test compound can also be those disclosed in U.S. Pat. No. 8,362,277; U.S. Publication No. 2011/0015217; U.S. Publication No. 2012/0022096 and U.S. Publication No. 2013/0040977; U.S. application Ser. No. 14/339,772 filed Jul. 24, 2014; U.S. Provisional Patent Application No. 61/902,680 filed Nov. 11, 2013 and U.S. Provisional Patent Application No. 61/912,625 filed Dec. 6, 2013, all of which are hereby incorporated herein by reference in their entirety, in particular the compounds disclosed in the Examples section.

The DNA-damaging agent is provided at can be provided at any suitable amount or concentration, e.g., about 0.01-20 uM, or about 0.05-10 uM, or about 0.1-1.5 uM, or about 0.5 uM, or any other suitable concentration one of ordinary skill can determine through routine experimentation depending on the specific cells or the DNA-damaging agent.

In some embodiments, the DNA-damaging agent based screen can be combined with the NAMPT based screen, to further confirm the cell-protective (e.g., neuroprotective) activity of the test compounds. For example, compounds of interest identified from the DNA-damaging agent based screen can be further incubated with NAMPT, and an activity of the NAMPT can be measured thereafter, wherein an increase in the activity of the NAMPT additionally confirms the cell-protective (e.g., neuroprotective) activity of the compound. Alternatively, compounds of interest identified from the NAMPT based screen can be further incubated with a population of cells and a DNA-damaging agent (the cells can be incubated with the compound and the DNA-damaging agent together or separately in two sequential steps), and survival rate of the population of cells can be determined thereafter; wherein an increase in the survival rate compared to a control that is not treated with the compound is indicative of cell-protective (e.g., neuroprotective) activity of the compound.

In some embodiments, the test compound having said cell-protective (e.g., neuroprotective) activity can be further determined to bind and/or activate the NAMPT. Determining the test compound having said cell-protective (e.g., neuroprotective) activity binds and/or activates the NAMPT can be done by any suitable methods such as mass spec and/or gel electrophoresis.

Compounds, Compound Forms and Salts

Compounds identified by the above screen methods are included in the present invention. In some embodiments, the compound can have formula (I):

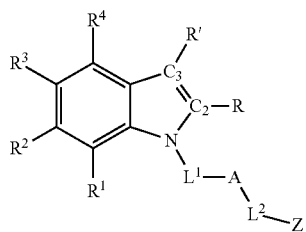

(I)

wherein:
each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), nitro, —C(O)O($C_1$-$C_6$ alkyl), —C(O)$NH_2$, —C(O)NH($C_1$-$C_6$ alkyl), —C(O)N($C_1$-$C_6$ alkyl)$_2$, —S(O)$_2$$NH_2$, —S(O)$_2$NH($C_1$-$C_6$ alkyl), and —S(O)$_2$N($C_1$-$C_6$ alkyl)$_2$;
R and R' are defined according to (1), (2), (3) or (4) below:
(1) R and R' together with $C_2$ and $C_3$, respectively, form a fused phenyl ring having formula (II):

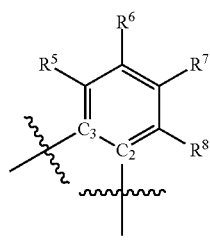

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), nitro, —C(O)O($C_1$-$C_6$ alkyl), —C(O)$NH_2$, —C(O)NH($C_1$-$C_6$ alkyl), —C(O)N($C_1$-$C_6$ alkyl)$_2$, —S(O)$_2$$NH_2$, —S(O)$_2$NH($C_1$-$C_6$ alkyl), and —S(O)$_2$N($C_1$-$C_6$ alkyl)$_2$; or (2) R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$; or (3) R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$; or (4) each of R and R' is, independently, hydrogen, $C_1$-$C_6$ alkyl, or $C_1$-$C_6$ haloalkyl;
each of $L^1$ and $L^2$ is, independently, $C_1$-$C_3$ alkylene, which is optionally substituted with from 1-2 independently selected $R^c$;
A is:
(i) $CR^{A1}R^{A2}$, wherein each of $R^{A1}$ and $R^{A2}$ is independently selected from hydrogen, halo, $C_1$-$C_3$ alkyl, $OR^9$, wherein $R^9$ is hydrogen or $C_1$-$C_3$ alkyl that is optionally substituted with hydroxyl or $C_1$-$C_3$ alkoxy, or a double bond formed between A and one of $L^1$ and $L^2$; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;
Z is:
(i) —$NR^{10}R^{11}$; or
(ii) —C(O)$NR^{10}R^{11}$; or
(iii) —$OR^{12}$; or
(iv) —S(O)$_n$$R^{13}$, wherein n is 0, 1, or 2; or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$; or
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$; or
(ix) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
(x) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
(xi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

each of $R^{10}$ and $R^{11}$ is independently selected from the substituents delineated collectively in (a) through (l) below:
  (a) hydrogen;
  (b) $C_6$-$C_{10}$ aryl that is optionally substituted with from 1-4 $R^b$;
  (c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
  (d) $C_1$-$C_6$ alkyl or $C_1$-$C_6$ haloalkyl, each of which is optionally substituted with from 1-3 $R^d$;
  (e) —C(O)($C_1$-$C_6$ alkyl), —C(O)($C_1$-$C_6$ haloalkyl), —C(O)O($C_1$-$C_6$ alkyl), —S(O)$_2$($C_1$-$C_6$ alkyl), —S(O)$_2$ ($C_6$-$C_{10}$ aryl), or —S(O)$_2$($C_1$-$C_{13}$ heteroaryl), wherein the $C_6$-$C_{10}$ aryl and $C_1$-$C_{13}$ heteroaryl are each independently optionally substituted with 1-4 $R^b$;
  (f) $C_2$-$C_6$ alkenyl or $C_2$-$C_6$ alkynyl;
  (g) $C_8$-$C_{14}$ arylcycloalkyl, wherein:
    (1) the aryl portion is optionally substituted with from 1-4 independently selected $R^b$, and
    (2) the cycloalkyl portion is optionally substituted with from 1-4 independently selected $R^a$;
  (h) arylheterocyclyl containing from 8-14 ring atoms, wherein:
    (1) the aryl portion from is optionally substituted with from 1-4 independently selected $R^b$, and
    (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
  (i) heteroarylheterocyclyl containing from 8-14 ring atoms, wherein:
    (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
    (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
  (j) heteroarylcycloalkyl containing from 8-14 ring atoms, wherein:
    (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
    (2) the cycloalkyl portion is optionally substituted with from 1-4 independently selected $R^a$;
  (k) $C_3$-$C_8$ cycloalkyl or $C_3$-$C_8$ cycloalkenyl, each of which is optionally substituted with from 1-4 independently selected $R^a$; and
  (l) $C_7$-$C_{12}$ aralkyl, wherein the aryl portion is optionally substituted with from 1-4 independently selected $R^b$, provided that one of $R^{10}$ and $R^{11}$ must be selected from (b), (c), (g), (h), (i), (j), and (k);

$R^{12}$ is:
  (i) $C_6$-$C_{10}$ aryl that is optionally substituted with from 1-4 $R^b$; or
  (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
  (iii) $C_1$-$C_6$ alkyl or $C_1$-$C_6$ haloalkyl, each of which is substituted with from 1-3 $R^d$; or
  (iv) $C_8$-$C_{14}$ arylcycloalkyl, wherein:
    (1) the aryl portion is optionally substituted with from 1-4 independently selected $R^b$, and
    (2) the cycloalkyl portion is optionally substituted with from 1-4 independently selected $R^a$; or
  (v) arylheterocyclyl containing from 8-14 ring atoms, wherein:
    (1) the aryl portion from is optionally substituted with from 1-4 independently selected $R^b$, and
    (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
  (vi) heteroarylheterocyclyl containing from 8-14 ring atoms, wherein:
    (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
    (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
  or
  (vii) heteroarylcycloalkyl containing from 8-14 ring atoms, wherein:
    (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
    (2) the cycloalkyl portion is optionally substituted with from 1-4 independently selected $R^a$;

$R^{13}$ is:
  (i) $C_6$-$C_{10}$ aryl that is optionally substituted with from 1-4 $R^b$; or
  (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or (iii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;

or (iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:

(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$-[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;

(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); —C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), —N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); —N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); —C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—.

In some embodiments, one or more of (A), (B), or (C) apply:

(A) Provided that when R and R' are defined according to definition (3), then:

(i) each of l2 and $L^2$ must be $C_1$-$C_3$ alkylene, which is optionally substituted with from 1-2 independently selected $R^c$ when A is $CH_2$; or (ii) -$L^3$-A-$L^2$- cannot be —$CH_2$—$CH_2$— when Z is 2-methylpyridyl; or (iii) Z must be other than heteroaryl containing from 5-14 (e.g., 5-6 or 6) ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., $CH_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

In some embodiments, (A), (B), or (C) applies. In other embodiments, (A) and (B); or (A) and (C); or (B) and (C) applies. In still other embodiments, (A), (B), and (C) apply.

In certain embodiments, the compounds are of formula (III):

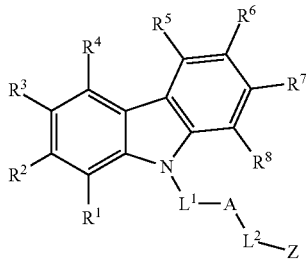

(III)

in which $R^1$, $R^2$, $R^3$, $R^4$, $L^1$, $L^2$, A, and Z can be as defined anywhere herein.

In some embodiments, one or more of the following can apply:
each of $L^1$ and $L^2$ is $CH_2$;
A is $CR^{41}R^{42}$, wherein one of $R^{41}$ and $R^{42}$ is $OR^9$, and the other is hydrogen;
Z is $-NR^{10}R^{11}$; and
each of $R^{10}$ and $R^{11}$ is independently selected from:
  (a) hydrogen;
  (b) $C_6$-$C_{10}$ aryl that is optionally substituted with from 1-4 $R^b$;
  (c) heteroaryl containing from 5-14 ring atoms, wherein from 1-6 of the ring atoms is independently selected from N, NH, N($C_1$-$C_3$ alkyl), O, and S, and wherein said heteroaryl is optionally substituted with from 1-4 $R^b$; e.g., pyridyl optionally substituted with 1 $R^b$; e.g., 2-methoxypyridyl;
  (d) $C_1$-$C_6$ alkyl or $C_1$-$C_6$ haloalkyl, each of which is optionally substituted with from 1-3 $R^d$;
  (f) $C_2$-$C_6$ alkenyl or $C_2$-$C_6$ alkynyl.

In embodiments, one or more of the following may apply:
provided that $R^3$ and $R^6$ cannot both be hydrogen when A is $CH_2$, and R and R' are defined according to definition (1);
provided that $R^3$ cannot be hydrogen when A is $CH_2$, and R and R' are defined according to definition (2);
provided that $R^3$ and $R^6$ cannot both be chloro when A is $CH_2$, R and R' are defined according to definition (1), Z is $-OR^{12}$, and $R^{12}$ is unsubstituted phenyl;
provided that $R^3$ and $R^6$ cannot both be bromo when A is $CH_2$, R and R' are defined according to definition (1), Z is $-OR^{12}$, and $R^{12}$ is phenyl that is substituted with pyridyl or alkyl that is substituted with from 1-3 $R^e$;
provided that $R^3$ and $R^6$ cannot both be hydrogen when A is $CH(CH_3)$, R and R' are defined according to definition (1), Z is $NR^{10}R^{11}$, $R^{10}$ is $CH_3$, and $R^{11}$ is unsubstituted phenyl;
provided that when A is $CR^{41}R^{42}$, and one of $R^{41}$ and $R^{42}$ is OH (i.e., $R^9$ is H), then the other of $R^{41}$ and $R^{42}$ is $C_1$-$C_3$ alkyl.

In certain embodiments, one or more of the following apply, e.g., when A is CHOH and Z is $NR^{10}R^{11}$:
each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);
each of $R^{10}$ and $R^{11}$ is other than hydrogen;
each of $R^{10}$ and $R^{11}$ is hydrogen;

one of $R^{10}$ and $R^{11}$ is heteroaryl (optionally substituted) as defined herein; and
$L^1$ and/or $L^2$ is $C_2$-$C_3$ alkylene (optionally substituted).

In certain embodiments, when $R^3$ and $R^6$ are both halo, one of $R^{41}$ and $R^{42}$ is OH and the other is hydrogen, Z is $-NHR^{10}$, and $R^{10}$ is $C_6$-$C_{10}$ aryl that is optionally substituted with 1 to 4 $R^b$, then $R^{10}$ is unsubstituted phenyl or phenyl substituted with 1 $R^b$.

In some embodiments, one of $R^{10}$ and $R^{11}$ must be (b) or (c).

The compound, in some embodiments, can be (+) or (−) (dextrorotatory) when in the presence of plane polarized light. In some embodiments, the (+) (dextrorotatory) compound can be substantially free of (e.g., containing less than about 5% of, less than about 2% of, less than about 1%, less than about 0.5%) a compound that is (levorotatory). In some embodiments, the (−) (levorotatory) compound can be substantially free of (e.g., containing less than about 5% of, less than about 2% of, less than about 1%, less than about 0.5%) a compound that is (+) (dextrorotatory).

In embodiments, the carbon attached to $R^{41}$ and $R^{42}$ is substituted with four different substituents (for purposes of clarification, these four substituents include $R^{41}$ and $R^{42}$) and is therefore a stereogenic center.

In certain embodiments, the carbon attached to $R^{41}$ and $R^{42}$ is (R) configured, meaning that the carbon attached to $R^{41}$ and $R^{42}$ has the (R) configuration (Cahn Ingold Prelog sequence rules notation). Such compounds are sometimes referred to herein as an "(R)-configured compound" (this term also includes compounds that further contain one or more stereogenic centers in addition to the (R)—$CR^{41}R^{42}$ stereogenic center). In other embodiments, the carbon attached to $R^{41}$ and $R^{42}$ is (S) configured, meaning that the carbon attached to $R^{41}$ and $R^{42}$ has the (S) configuration (Cahn Ingold Prelog sequence rules notation). Such compounds are sometimes referred to herein as an "(S)-configured compound" (this term also includes compounds that further contain one or more stereogenic centers in addition to the (S)—$CR^{41}R^{42}$ stereogenic center). In embodiments, the (R) configured compound (or salt, e.g., a pharmaceutically acceptable salt, thereof) is substantially free of (e.g., contains less than about 5% of, less than about 2% of, less than about 1%, less than about 0.5% of) a compound (or salt thereof as described herein) that is (S) configured at the carbon attached to $R^{41}$ and $R^{42}$ (i.e., a compound in which the carbon attached to $R^{41}$ and $R^{42}$ has the (S) configuration). For example, the (R) configured compound can be an (R)-enantiomer that is substantially free of its opposing (S) enantiomer. As another example, an (R) configured compound can be substantially free of a diastereomer in which the carbon attached to $R^{41}$ and $R^{42}$ has the (S) configuration. In certain embodiments, the (R) configured compound can be additionally in substantially pure form (e.g., contains less than about 5% of, less than about 2% of, less than about 1%, less than about 0.5% of other substances, including, for example, one or more of other compounds). In embodiments, the (S) configured compound (or salt, e.g., a pharmaceutically acceptable salt, thereof) is substantially free of (e.g., contains less than about 5% of, less than about 2% of, less than about 1%, less than about 0.5% of) a compound (or salt thereof as described herein) that is (R) configured at the carbon attached to $R^{41}$ and $R^{42}$ (i.e., a compound in which the carbon attached to $R^{41}$ and $R^{42}$ has the (R) configuration). For example, the (S) configured compound can be an (S)-enantiomer that is substantially free of its opposing (R) enantiomer. As another example, the (S) configured compound can be substantially free of a diastereomer in which the carbon attached to $R^{41}$ and $R^{42}$ has the (R)

configuration. In certain embodiments, the (S) configured compound can be additionally in substantially pure form (e.g., contains less than about 5% of, less than about 2% of, less than about 1%, less than about 0.5% of other substances, including, for example, one or more of other compounds).

The cell-protective (e.g., neuroprotective) compound of the present invention can include any one or more compounds selected from:

R-1-(3,6-Dibromo-9H-carbazol-9-yl)-3-(3-methoxyphenylamino)-propan-2-ol;
S-1-(3,6-Dibromo-9H-carbazol-9-yl)-3-(3-methoxyphenylamino)-propan-2-ol;
1-(3,6-dibromo-9H-carbazol-9-yl)-3-(2-iminopyridin-1(2H)-yl)propan-2-ol;
1-(3,6-dibromo-9H-carbazol-9-yl)-3-(phenylthio)propan-2-ol;
N-(3-(3,6-dibromo-9H-carbazol-9-yl)-2-hydroxypropyl)-N-(3-methoxyphenyl)acetamide;
5-((3,6-dibromo-9H-carbazol-9-yl)methyl)-3-(3-methoxyphenyl)-oxazolidin-2-one;
N-(3-(3,6-dibromo-9H-carbazol-9-yl)-2-fluoropropyl)-3-methoxyaniline;
1-(3,6-dibromo-9H-carbazol-9-yl)-3-(3-methoxyphenylamino)-propan-2-one;
N-(3-(3,6-dibromo-9H-carbazol-9-yl)-2-methoxypropyl)-3-methoxyaniline;
1-(3,6-Dimethyl-9H-carbazol-9-yl)-3-(3-methoxyphenylamino)propan-2-ol;
1-(3-Bromo-6-methyl-9H-carbazol-9-yl)-3-(3-methoxyphenylamino)-propan-2-ol;
1-(3,6-Dichloro-9H-carbazol-9-yl)-3-(3-methoxyphenylamino)propan-2-ol;
1-(5-bromo-2,3-dimethyl-1H-indol-1-yl)-3-(phenylamino)propan-2-ol;
1-(3,6-Dibromo-9H-pyrido[3,4-b]indol-9-yl)-3-(phenylamino)propan-2-ol;
1-(3-Azidophenylamino)-3-(3,6-dibromo-9H-carbazol-9-yl)propan-2-ol;
1,3-Bis(3,6-dibromo-9H-carbazol-9-yl)propan-2-ol;
1-(9H-Carbazol-9-yl)-3-(3,6-dibromo-9H-carbazol-9-yl)propan-2-ol;
3-(3,6-Dibromo-9H-carbazol-9-yl)-2-hydroxy-N-(3-methoxyphenyl)-propanamide;
Ethyl 5-(2-Hydroxy-3-(3-methoxyphenylamino)propyl)-8-methyl-3,4-dihydro-1H-pyrido[4,3-b]indole-2(5H)-carboxylate;
4-(3,6-dibromo-9H-carbazol-9-yl)-1-(phenylamino)butan-2-ol;
N-(3-(3,6-dibromo-9H-carbazol-9-yl)propyl)aniline;
1-(3,6-dibromo-9H-carbazol-9-yl)-4-(phenylamino)butan-2-ol;
1-(3,6-dibromo-9H-carbazol-9-yl)-3-(pyridin-2-ylamino)propan-2-ol;
1-(3,6-dibromo-9H-carbazol-9-yl)-3-((3-methoxyphenyl)(methyl)-amino)propan-2-ol;
3-(3,6-dibromo-9H-carbazol-9-yl)-1-(3-methoxyphenylamino)-1-(methylthio)propan-2-one;
3-amino-1-(3-(3,6-dibromo-9H-carbazol-9-yl)-2-hydroxypropyl)pyridinium;
1-(3,6-dibromo-9H-carbazol-9-yl)-3-(pyrimidin-2-ylamino)propan-2-ol;
N-(3-(3,6-dibromo-9H-carbazol-9-yl)-2-fluoropropyl)-3-methoxy-N-methylaniline;
1-(3,6-dibromo-9H-carbazol-9-yl)-3-methoxypropan-2-ol;
1-(3,6-dibromo-9H-carbazol-9-yl)-4-phenylbutan-2-ol;
1-(3,6-dibromo-9H-carbazol-9-yl)-3-(1H-indol-1-yl)propan-2-ol;
3-(1-(3-(3,6-dibromo-9H-carbazol-9-yl)-2-hydroxypropyl)-1H-1,2,3-triazol-4-yl)propan-1-ol;
1-(3,6-dibromo-9H-carbazol-9-yl)-3-(3-ethoxyphenylamino)propan-2-ol;
1-(3,6-dibromo-9H-carbazol-9-yl)-3-(3,5-dimethyl-1H-pyrazol-1-yl)propan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
1-(3-bromo-9H-carbazol-9-yl)-3-(3-methoxyphenylamino)propan-2-ol;
N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide;
1-(3,6-dibromo-9H-carbazol-9-yl)-3-phenoxypropan-2-ol;
N-(2-(3-(3,6-dibromo-9H-carbazol-9-yl)-2-hydroxypropoxy)ethyl)-acetamide;
1-(3,6-dibromo-9H-carbazol-9-yl)-3-(pyridin-3-ylamino)propan-2-ol;
1-(3,6-dibromo-9H-carbazol-9-yl)-3-(pyridin-4-ylamino)propan-2-ol;
1-(2,8-dimethyl-3,4-dihydro-1H-pyrido[4,3-b]indol-5(2H)-yl)-3-(phenylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
1-(3,6-dibromo-9H-carbazol-9-yl)-3-(phenylamino)propan-2-ol;
1-(3,6-dibromo-9H-carbazol-9-yl)-3-(o-tolylamino)propan-2-ol;
1-(3,6-dibromo-9H-carbazol-9-yl)-3-(m-tolylamino)propan-2-ol;
1-(3,6-dibromo-9H-carbazol-9-yl)-3-(2-methoxyphenylamino)propan-2-ol;
1-(3,6-dibromo-9H-carbazol-9-yl)-3-(naphthalen-1-ylamino)propan-2-ol;
1-(4-bromophenylamino)-3-(3,6-dichloro-9H-carbazol-9-yl)propan-2-ol;
1-(4-bromophenylamino)-3-(3,6-dibromo-9H-carbazol-9-yl)propan-2-ol;
1-(3,6-dibromo-9H-carbazol-9-yl)-3-(4-ethoxyphenylamino)propan-2-ol;
1-(4-chlorophenylamino)-3-(3,6-dibromo-9H-carbazol-9-yl)propan-2-ol;
1-(3,6-dibromo-9H-carbazol-9-yl)-3-(phenethylamino)propan-2-ol;
1-(3,6-dibromo-9H-carbazol-9-yl)-3-(2-hydroxyethylamino)propan-2-ol;
1-(3,6-dibromo-9H-carbazol-9-yl)-3-(2,4-dimethoxyphenylamino)propan-2-ol;
1-(3,6-dibromo-9H-carbazol-9-yl)-3-(2,3-dimethylphenylamino)propan-2-ol;
1-(2-chlorophenylamino)-3-(3,6-dibromo-9H-carbazol-9-yl)propan-2-ol;
1-(tert-butylamino)-3-(3,6-dibromo-9H-carbazol-9-yl)propan-2-ol;
1-(3,6-dibromo-9H-carbazol-9-yl)-3-(isopropylamino)propan-2-ol;
1-(3,6-dibromo-9H-carbazol-9-yl)-3-(4-methoxyphenylamino)propan-2-ol;
1-(3,6-dibromo-9H-carbazol-9-yl)-3-(3-methoxyphenylamino)propan-2-ol;
1-(3,6-dibromo-9H-carbazol-9-yl)-3-(m-tolylamino)propan-2-ol;
1-(3,6-dibromo-9H-carbazol-9-yl)-3-(3,5-dimethylphenylamino)propan-2-ol;

1-(3,6-dibromo-9H-carbazol-9-yl)-3-(3,4-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(2,5-dimethylphenylamino)propan-2-ol;
1-(4-bromophenylamino)-3-(2,3-dimethyl-1H-indol-1-yl)propan-2-ol;
1-(2,3-dimethyl-1H-indol-1-yl)-3-(4-methoxyphenylamino)propan-2-ol;
1-(2,3-dimethyl-1H-indol-1-yl)-3-(4-ethoxyphenylamino)propan-2-ol;
1-(2,3-dimethyl-1H-indol-1-yl)-3-(p-tolylamino)propan-2-ol;
1-(2,3-dimethyl-1H-indol-1-yl)-3-(phenylamino)propan-2-ol oxalate;
1-(1H-indol-1-yl)-3-(4-methoxyphenylamino)propan-2-ol hydrochloride;
1-(1H-indol-1-yl)-3-(phenylamino)propan-2-ol oxalate;
1-(3,4-dihydro-1H-carbazol-9(2H)-yl)-3-(m-tolylamino)propan-2-ol;
1-(9H-carbazol-9-yl)-3-(phenylamino)propan-2-ol;
1-(3,6-dichloro-9H-carbazol-9-yl)-3-(phenylamino)propan-2-ol;
1-(9H-carbazol-9-yl)-3-(p-tolylamino)propan-2-ol;
1-(3,6-dichloro-9H-carbazol-9-yl)-3-(p-tolylamino)propan-2-ol;
1-(3,6-dibromo-9H-carbazol-9-yl)-3-(p-tolylamino)propan-2-ol;
N-(4-(3-(9H-carbazol-9-yl)-2-hydroxypropoxy)phenyl)acetamide;
1-(9H-carbazol-9-yl)-3-phenoxypropan-2-ol;
1-(9H-carbazol-9-yl)-3-(4-methoxyphenylamino)propan-2-ol;
1-(benzylamino)-3-(9H-carbazol-9-yl)propan-2-ol;
methyl 4-(3-(9H-carbazol-9-yl)-2-hydroxypropoxy)benzoate;
1-(9H-carbazol-9-yl)-3-(4-methoxyphenoxy)propan-2-ol;
1-amino-3-(3,6-dibromo-9H-carbazol-9-yl)propan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(2,8-dimethyl-3,4-dihydro-1H-pyrido[4,3-b]indol-5(2H)-yl)-3-(3-methoxyphenylamino)propan-2-ol;
1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy)propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino) propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate; and
N-(3-(3,6-dibromo-9H-carbazol-9-yl)-2-fluoropropyl)-4-(2-(2-methoxyethoxyl)ethoxy)aniline;
N-(2-(2-(4-(3-(3,6-dibromo-9H-carbazol-9-yl)-2-fluoropropylamino)phenoxy)acetamido)ethyl)-5-(2-oxohexahydro-1H-thieno[3,4-d]imidazol-4-yl)pentanamide;
2-(4-(3-(3,6-dibromo-9H-carbazol-9-yl)-2-fluoropropylamino)phenoxy)-N,N-dimethylacetamide;
2-(4-(3-(3,6-dibromo-9H-carbazol-9-yl)-2-fluoropropylamino)phenoxy)-N-(2-hydroxyethyl)acetamide;
1-(bis(4-bromophenyl)amino)-3-(phenylamino)propan-2-ol;
(E)-3,6-dibromo-9-(3-phenoxyallyl)-9H-carbazole;
(E)-3,6-dibromo-9-(3-phenoxyprop-1-en-1-yl)-9H-carbazole;
1-(3,6-bis(trifluoromethyl)-9H-carbazol-9-yl)-3-(phenylamino)propan-2-ol;
1-(2,8-Dibromo-10,11-dihydro-5H-dibenzo[b,f]azepin-5-yl)-3-(3-methoxyphenylamino)propan-2-ol;
1-(3,6-Dibromo-9H-carbazol-9-yl)-3-(3-methoxyphenylthio)propan-2-ol;
1-(3,6-Dibromo-9H-carbazol-9-yl)-3-(4-methoxyphenylthio)propan-2-ol;
3,6-Dibromo-9-(2-fluoro-3-(3-methoxyphenylthio)propyl)-9H-carbazole;
3,6-Dibromo-9-(2-fluoro-3-(4-methoxyphenylthio)propyl)-9H-carbazole;
3,6-Dibromo-9-(2-fluoro-3-(3-methoxyphenylsulfonyl)propyl)-9H-carbazole;
1-(3,6-Dibromo-9H-carbazol-9-yl)-3-(3-methoxyphenylsulfonyl)propan-2-ol;
3,6-Dibromo-9-(2-fluoro-3-(4-methoxyphenylsulfonyl)propyl)-9H-carbazole;
1-(3,6-Dibromo-9H-carbazol-9-yl)-3-(4-methoxyphenylsulfonyl)propan-2-ol;
3-(3-(3,6-Dibromo-9H-carbazol-9-yl)-2-hydroxypropylthio)phenol;
4-(3-(3,6-Dibromo-9H-carbazol-9-yl)-2-hydroxypropylthio)phenol;
3-(3-(3,6-Dibromo-9H-carbazol-9-yl)-2-hydroxypropylsulfonyl)phenol;
4-(3-(3,6-Dibromo-9H-carbazol-9-yl)-2-hydroxypropylsulfonyl)phenol;
1-(3-Aminophenylthio)-3-(3,6-dibromo-9H-carbazol-9-yl)propan-2-ol;
1-(4-Aminophenylthio)-3-(3,6-dibromo-9H-carbazol-9-yl)propan-2-ol;
1-(3,6-dibromo-9H-carbazol-9-yl)-3-phenoxypropan-2-amine;
N-Benzyl-2-(3-(3-(3,6-dibromo-9H-carbazol-9-yl)-2-hydroxypropylthio)-phenoxy)acetamide;
N-Benzyl-2-(4-(3-(3,6-dibromo-9H-carbazol-9-yl)-2-hydroxypropylthio)-phenoxy)acetamide;

3-(3-(3,6-Dibromo-9H-carbazol-9-yl)-2-fluoropropylsulfonyl)phenol;
N-Benzyl-2-(3-(3-(3,6-dibromo-9H-carbazol-9-yl)-2-hydroxypropylsulfonyl)-phenoxy)acetamide;
4-(3-(3,6-Dibromo-9H-carbazol-9-yl)-2-fluoropropylsulfonyl)phenol;
5-(5-(3-(3-(3,6-dibromo-9H-carbazol-9-yl)-2-hydroxypropylamino)phenoxy)pentylcarbamoyl)-2-(6-hydroxy-3-oxo-3H-xanthen-9-yl)benzoic acid;
1-(8-bromo-3,4-dihydro-1H-pyrido[4,3-b]indol-5(2H)-yl)-3-phenoxypropan-2-ol;
1-(8-bromo-2-cyclopropyl-3,4-dihydro-1H-pyrido[4,3-b]indol-5(2H)-yl)-3-phenoxypropan-2-ol;
8-bromo-5-(2-hydroxy-3-phenoxypropyl)-3,4-dihydro-1H-pyrido[4,3-b]indole-2(5H)-carbonitrile;
8-bromo-5-(2-fluoro-3-phenoxypropyl)-2,3,4,5-tetrahydro-1H-pyrido[4,3-b]indole;
1-(cyclohexylamino)-3-(3,6-dibromo-9H-carbazol-9-yl)propan-2-ol;
(9-(2-hydroxy-3-(phenylthio)propyl)-9H-carbazole-3,6-dicarbonitrile;
9-(2-hydroxy-3-phenoxypropyl)-9H-carbazole-3,6-dicarbonitrile;
R—N-(3-(3,6-dibromo-9H-carbazol-9-yl)-2-fluoropropyl)-3-methoxyaniline
S—N-(3-(3,6-dibromo-9H-carbazol-9-yl)-2-fluoropropyl)-3-methoxyaniline
N-(2-(3,6-dibromo-9H-carbazol-9-yl)ethyl)aniline;
2-(6-Amino-3-imino-3H-xanthen-9-yl)-4-(6-(5-(3-(3-(3,6-dibromo-9H-carbazol-9-yl)-2-hydroxypropylamino)phenoxy)pentylamino)-6-oxohexylcarbamoyl)benzoic acid AND
2-(6-amino-3-imino-3H-xanthen-9-yl)-5-(6-(5-(3-(3-(3,6-dibromo-9H-carbazol-9-yl)-2-hydroxypropylamino)phenoxy)pentylamino)-6-oxohexylcarbamoyl)benzoic acid;
1-(8-bromo-2-methyl-3,4-dihydro-1H-pyrido[4,3-b]indol-5(2H)-yl)-3-phenoxypropan-2-ol;
6-((4-bromophenyl)(2-hydroxy-3-phenoxypropyl)amino)nicotinonitrile;
1-(3-(3,6-dibromo-9H-carbazol-9-yl)-2-hydroxypropyl)pyridin-2(1H)-one;
9-(2-hydroxy-3-phenoxypropyl)-9H-carbazole-3-carbonitrile;
tert-butyl(5-(4-((3-(3,6-dibromo-9H-carbazol-9-yl)-2-hydroxypropyl)sulfonyl) phenoxy)pentyl)carbamate;
6-bromo-9-(2-hydroxy-3-phenoxypropyl)-9H-carbazole-3-carbonitrile;
6-bromo-9-(2-hydroxy-3-phenoxypropyl)-9H-carbazole-3-carboxamide;
1-(3,6-dibromo-9H-carbazol-9-yl)-3-(pyridin-2-yloxy)propan-2-ol;
methyl 6-bromo-9-(2-hydroxy-3-phenoxypropyl)-9H-carbazole-3-carboxylate;
6-bromo-9-(2-hydroxy-3-phenoxypropyl)-9H-carbazole-3-carboxylic acid;
6-bromo-9-(2-hydroxy-3-phenoxypropyl)-9H-pyrido[2,3-b]indole-3-carbonitrile;
9-(2-hydroxy-3-phenoxypropyl)-9H-pyrido[2,3-b]indole-3-carbonitrile;
tert-butyl 3-(2-(2-(2-(3-((3-(3,6-dibromo-9H-carbazol-9-yl)-2-hydroxypropyl)amino)phenoxy)ethoxy)ethoxy)ethoxy)propanoate;
1-(3,6-dibromo-1,4-dimethoxy-9H-carbazol-9-yl)-3-(phenylamino)propan-2-ol;
1-(3,6-dibromo-1,8-dimethyl-9H-carbazol-9-yl)-3-(phenylamino)propan-2-ol;
2-(3,6-dibromo-9H-carbazol-9-yl)acetic acid;
1-(6-bromo-3-methoxy-1-methyl-9H-carbazol-9-yl)-3-(phenylamino)propan-2-ol;
1-(4,6-dibromo-3-methoxy-1-methyl-9H-carbazol-9-yl)-3-(phenylamino)propan-2-ol;
1-(3,6-dibromo-4-methoxy-9H-carbazol-9-yl)-3-(phenylamino)propan-2-ol;
9-(2-hydroxy-3-phenoxypropyl)-9H-pyrido[3,4-b]indole-3-carboxylic acid;
6-bromo-9-(2-hydroxy-3-phenoxypropyl)-9H-pyrido[3,4-b]indole-3-carboxylic acid;
ethyl 6-bromo-9-(2-hydroxy-3-phenoxypropyl)-9H-pyrido[3,4-b]indole-3-carboxylate;
9-(2-fluoro-3-phenoxypropyl)-9H-carbazole-3,6-dicarbonitrile;
9-(2-hydroxy-2-methyl-3-phenoxypropyl)-9H-carbazole-3,6-dicarbonitrile;
1-(cyclohexyloxy)-3-(3,6-dibromo-9H-carbazol-9-yl)propan-2-ol;
(E)-N-(3-(3,6-dibromo-9H-carbazol-9-yl)prop-1-en-1-yl)-1,1,1-trifluoro-N-(3-methoxyphenyl)methanesulfonamide;
1-(3,6-dibromo-9H-pyrido[2,3-b]indol-9-yl)-3-phenoxypropan-2-ol;
1-(3,6-dibromo-9H-carbazol-9-yl)-3-((6-methoxypyridin-2-yl)amino)propan-2-ol;
1-(8-bromo-5H-pyrido[4,3-b]indol-5-yl)-3-phenoxypropan-2-ol;
6-bromo-9-(2-hydroxy-3-phenoxypropyl)-9H-pyrido[3,4-b]indole-3-carboxamide;
8-bromo-5-(2-hydroxy-3-phenoxypropyl)-5H-pyrido[4,3-b]indole 2-oxide;
8-bromo-5-(2-hydroxy-3-phenoxypropyl)-5H-pyrido[3,2-b]indole 1-oxide;
(6-bromo-9H-pyrido[3,4-b]indol-3-yl)methanol;
ethyl 6-bromo-9H-pyrido[3,4-b]indole-3-carboxylate;
tert-butyl(3-(3,6-dibromo-9H-carbazol-9-yl)-2-fluoropropyl)carbamate;
2-(3,6-dibromo-9H-carbazol-9-yl)-N-methylacetamide;
3-(3,6-dibromo-9H-carbazol-9-yl)-2-fluoropropan-1-amine hydrochloride;
N-(3-(3,6-dibromo-9H-carbazol-9-yl)-2-fluoropropyl)acetamide;
2-(3,6-dibromo-9H-carbazol-9-yl)propanamide;
6-bromo-9H-pyrido[3,4-b]indole-3-carbonitrile;
6-bromo-3-methyl-9H-pyrido[3,4-b]indole;
methyl(2-(3,6-dibromo-9H-carbazol-9-yl)acetyl)carbamate;
N-(3-(3,6-dibromo-9H-carbazol-9-yl)-2-fluoropropyl)-1,1,1-trifluoro-N-(3-methoxyphenyl)methanesulfonamide;
N-(3-(3,6-dibromo-9H-carbazol-9-yl)-2-fluoropropyl)-6-methoxypyridin-2-amine;
N-(3-(3,6-dibromo-9H-carbazol-9-yl)-2-hydroxypropyl)-1,1,1-trifluoro-N-(3-methoxyphenyl)methanesulfonamide;
1-(3,6-dibromo-9H-carbazol-9-yl)-3-((4-methoxybenzyl)(3-methoxyphenyl)amino)propan-2-ol;
N-(3-(3,6-dibromo-9H-carbazol-9-yl)-2-hydroxypropyl)-2,2,2-trifluoroacetamide;
tert-butyl(3-(3,6-dibromo-9H-carbazol-9-yl)-2-hydroxypropyl)carbamate;
5-(2-hydroxy-3-phenoxypropyl)-5H-pyrimido[5,4-b]indole-2-carboxylic acid;
N-(3-(3,6-dibromo-9H-carbazol-9-yl)-2-hydroxypropyl)acetamide;
ethyl(3-(3,6-dibromo-9H-carbazol-9-yl)-2-hydroxypropyl)carbamate;
6-bromo-9-(3-(4-bromophenoxy)-2-hydroxypropyl)-9H-carbazole-3-carbonitrile;
methyl 9-(2-hydroxy-3-phenoxypropyl)-9H-pyrido[3,4-b]indole-3-carboxylate;

N-(3-(3-bromo-6-methyl-9H-carbazol-9-yl)-2-fluoropropyl)-6-methoxypyridin-2-amine;

or a salt (e.g., a pharmaceutically acceptable salt) thereof.

In some embodiments, the compound can be those listed in Table 1, in particular those having a Δ(Sinf−S0)/AC50 value greater than about 0, or greater than about 1, or greater than about 2, or greater than about 3, or greater than about 4, or greater than about 5, or greater than about 10, or greater than about 20, or greater than about 30, or greater than about 40, or greater than about 50, or greater than about 60, or greater than about 70, or greater than about 80, or greater than about 90, or greater than about 100.

The compounds can be further studied, purified and/or modified. For example, the compounds may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the present disclosure. The compounds of the present disclosure may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present disclosure. The compounds of the present disclosure may also be represented in multiple tautomeric forms, in such instances, the present disclosure expressly includes all tautomeric forms of the compounds described herein, even though only a single tautomeric form may be represented. All such isomeric forms of such compounds are expressly included in the present disclosure.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the present disclosure encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the present disclosure include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present disclosure and their pharmaceutically acceptable acid addition salts. Salts derived from appropriate bases include alkali metal (e.g., sodium), alkaline earth metal (e.g., magnesium), ammonium and N-(alkyl)$_4^+$ salts. The present disclosure also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present disclosure which is administered as an ester (the "prodrug"), but then is metabolically hydrolyzed to the carboxylic acid, the active entity. Additional examples include peptidyl derivatives of a compound of the present disclosure.

The present disclosure also includes various hydrate and solvate forms of the compounds.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

Synthesis

The compounds of the present disclosure can be conveniently prepared in accordance with the procedures outlined in the Examples sections of U.S. Pat. No. 8,362,277; U.S. Publication No. 2011/0015217; U.S. Publication No. 2012/0022096; U.S. Publication No. 2013/0040977; U.S. application Ser. No. 14/339,772 filed Jul. 24, 2014; U.S. Provisional Patent Application No. 61/902,680 filed Nov. 11, 2013 and U.S. Provisional Patent Application No. 61/912,625 filed Dec. 6, 2013, all of which are hereby incorporated herein by reference in their entirety. The compounds can also be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}F$ NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

Pharmaceutical Compositions

The term "pharmaceutically acceptable carrier" refers to a carrier or adjuvant that may be administered to a subject (e.g., a patient), together with a compound of the present disclosure, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of the present disclosure include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multi-pack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of capsule formulations.

Capsule Formulations

| | Capsule Formulation | | | |
|---|---|---|---|---|
| | Formulation 1 mg/capsule | Formulation 2 mg/capsule | Formulation 3 mg/capsule | Formulation 4 mg/capsule |
| Compound (solid solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline compound (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

Use

The compounds disclosed herein can be used, in one aspect, to treat DNA-damaging agent (e.g., anthracycline) mediated cardiotoxicity. The compounds can also be used to treat one or more diseases, disorders, or conditions caused by, or associated with, aberrant (e.g., insufficient) neurogenesis or accelerated neuron cell death in a subject in need thereof.

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions. The methods include administering to the subject an effective amount of a compound of formula (I) (and/or any other compound described herein) or a salt (e.g., a pharmaceutically acceptable salt) thereof as defined anywhere herein to the subject.

In another aspect, the use of a compound of formula (I) (and/or any other compound described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions.

In embodiments, the one or more diseases, disorders, or conditions can include DNA-damaging agent (e.g., anthracycline) mediated cardiotoxicity, neuropathies, nerve trauma, and neurodegenerative diseases. In embodiments, the one or more diseases, disorders, or conditions can be diseases, disorders, or conditions caused by, or associated with aberrant (e.g., insufficient) neurogenesis (e.g., aberrant hippocampal neurogenesis as is believed to occur in neuropsychiatric diseases) or accelerated death of existing neurons. Examples of the diseases, disorders, or conditions include, but are not limited to, DNA-damaging agent (e.g., anthracycline) mediated cardiotoxicity, schizophrenia, major depression, bipolar disorder, normal aging, epilepsy, traumatic brain injury and/or a visual symptom associated therewith, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuro-active drug, retinal degeneration, spinal cord injury, peripheral nerve injury, physiological weight loss associated with various conditions, cognitive decline and/or general frailty associated with normal aging and/or chemotherapy, chemotherapy induced neuropathy, concussive injury, crush injury, peripheral neuropathy, diabetic neuropathy, post-traumatic headache, multiple sclerosis, retinal degeneration and dystrophy (such as Leber congenital amaurosis, retinitis pigmentosa, cone-rod dystrophy, microphthalmia, anophthalmia, myopia, and hyperopia), spinal cord injury, traumatic spinal cord injury, peripheral nerve injury (such as peripheral nerve crush injury, neonatal brachial plexus palsy, and traumatic facial nerve palsy), retinal neuronal death related diseases (such as glaucoma and age related macular degeneration, diabetic retinopathy, retinal blood vessel occlusions, retinal medication toxicity (such as what amino glycosides or plaquenil can cause), retinal trauma (e.g., post-surgical), retinal infections, choroidal dystrophies, retinal pigmentary retinopathies, inflammatory and cancer mediated auto immune diseases that result in retinal neuronal cell death), Autism, Stargardt disease, Kearns-Sayre syndrome, Pure neurosensory deafness, Hereditary hearing loss with retinal diseases, Hereditary hearing loss with system atrophies of the nervous system, Progressive spinal muscular atrophy, Progressive bulbar palsy, Primary lateral sclerosis, Hereditary forms of progressive muscular atrophy and spastic paraplegia, Frontotemporal dementia, Dementia with Lewy bodies, Corticobasal degeneration, Progressive supranuclear palsy, Prion disorders causing neurodegeneration, Multiple system atrophy (olivopontocerebellar atrophy), Hereditary spastic paraparesis, Friedreich ataxia, Non-Friedreich ataxia, Spinocerebellar atrophies, Amyloidoses, Metabolic-related (e.g., Diabetes) neurodegenerative disorders, Toxin-related neurodegenerative disorders, Multiple sclerosis, Charcot Marie Tooth, Diabetic neuropathy, Metabolic neuropathies, Endocrine neuropathies, Orthostatic hypotension, Creutzfeldt-Jacob Disease, Primary progressive aphasia, Frontotemporal Lobar Degeneration, Cortical blindness, Shy-Drager Syndrome (Multiple, System Atrophy with Orthostatic Hypotension), Diffuse cerebral cortical atrophy of non-Alzheimer type, Lewy-body dementia, Pick disease (lobar atrophy), Thalamic degeneration, Mesolimbocortical dementia of non-Alzheimer type, Nonhuntingtonian types of chorea and dementia, Cortical-striatal-spinal degeneration, Dementia-Parkinson-amyotrophic lateral sclerosis complex, Cerebrocerebellar degeneration, Cortico-basal ganglionic degeneration, Familial dementia with spastic paraparesis or myoclonus, and Tourette syndrome.

The resultant promotion of neurogenesis or survival of existing neurons (i.e., a resultant promotion of survival, growth, development, function and/or generation of neurons) may be detected directly, indirectly or inferentially from an improvement in, or an amelioration of one or more symptoms of the disease or disorder caused by or associated with aberrant neurogenesis or survival of existing neurons. Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol Neurobiol. 2008 Nov. 6); protection against motor neuron degeneration in mice (e.g. Poesen et al., J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., Behav Pharmacol. 2007 September; 18(5-6):391-418; Krishnan et al., Nature 2008, 455, 894-902); and/or those exemplified herein.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the present disclosure may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of the present disclosure (e.g., sequentially, e.g., on different overlapping schedules with the administration of one or more compounds of formula (I) (including any subgenera or specific compounds thereof)). In other embodiments, these agents may be part of a single dosage form, mixed together with the compounds of the present disclosure in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of the present disclosure include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the present disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of the present disclosure may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of the present disclosure may also be administered in the form of suppositories for rectal administration. These compositions can be prepared by mixing a compound of the present disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of the present disclosure is useful when the desired treatment involves areas or organs readily accessible by topical application. For application topically to the skin, the composition should be formulated with a suitable ointment containing the active components suspended or dissolved in a carrier. Carriers for topical administration of the compounds of the present disclosure include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of the present disclosure may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in the present disclosure. Also within the present disclosure is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of the present disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in the present disclosure. For example, timed-release formulations based on polymer technologies, sustained-release techniques and encapsulation techniques (e.g., polymeric, liposomal) can also be used for delivery of the compounds and compositions delineated herein.

The present disclosure will be further described in the following examples. It should be understood that these examples are for illustrative purposes only and are not to be construed as limiting the present disclosure in any manner. For example, while the examples refer to neuroprotective compounds, it should be understood that these compounds can also be used to protect other cells from DNA-damaging agent induced cell toxicity, and/or promote the general health, survival and growth of other cells.

Examples

Active members of the "pool seven compound three" (P7C3) class of aminopropyl carbazole chemicals foster the survival of neurons in a variety of rodent models of neurodegeneration or nerve cell injury. A P7C3 derivative modified to contain a benzophenone moiety facilitated UV light-mediated cross linking to nicotinamide phosphoribosyltransferase (NAMPT), the rate limiting enzyme involved in the conversion of nicotinamide into nicotinamide adenine dinucleotide (NAD). Administration of active variants of this class of chemicals to cells treated with doxorubicin led to a rebound in intracellular levels of NAD and concomitant protection from doxorubicin-mediated toxicity. Active P7C3 variants likewise enhanced the activity of the purified NAMPT enzyme. Optimized aminopropyl carbazole chemicals offer promise for the development of therapeutics for the treatment of neurodegenerative diseases and other conditions involving nerve cell injury.

Background

No substantive therapeutics are available for the treatment of almost any form of disease entailing nerve cell death. Patients suffering from any of a wide spectrum of neurodegenerative diseases, including Parkinson's disease, Alzheimer's disease, amyotrophic lateral sclerosis, fronto-temporal dementia and Huntington's disease are condemned to progressive demise of the CNS by virtue of nerve cell death. It is likewise the case that no effective treatments exist for injuries to the brain or peripheral nervous system, including traumatic or concussive brain injury, spinal cord injury, or peripheral nerve injury. Any chemical having the capacity to safely impede nerve cell death in the context of these varied diseases or injuries would offer the opportunity for transformative impact in modern medicine.

Previously we performed a target-agnostic, in vivo screen in search of chemicals that might enhance hippocampal neurogenesis in adult mice (Pieper et al., 2010). The screen was simple in concept. With help from chemists in the Department of Biochemistry at UTSWMC, we selected 1,000 druglike chemicals from the 250,000 compounds in our high throughput screening center. The compounds were selected to preserve representative chemical diversity of the entire library. They were further selected to enhance the representation of chiral molecules, and to avoid untoward chemical properties such as reactive moieties. The 1,000 molecules were randomly pooled into groups of ten, and each pool was administered directly into the left ventricle of two adult mice. Intracranial delivery was facilitated by stereotactic positioning of a canula fed directly by an Alzet mini-pump containing the mixture of ten chemicals. The drug mixture was administered over a week-long period at concentrations anticipated to deliver mid-nanomolar levels of the ten test compounds. Daily injections of the thymidine analog, bromodeoxyuridine (BrdU), were coadministered in order to monitor the formation of new hippocampal nerve cells. Following compound administration, animals were sacrificed such that brain tissue could be recovered, sectioned and stained with antibodies to BrdU. This two-year screen led to the discovery of a handful of pools that enhanced neurogenesis in both test mice that had been exposed to the pool. Breakdown of the active pools allowed the individual testing of each of the ten chemicals in the pool, leading to the discovery of eight pro-neurogenic chemicals (Pieper et al., 2010).

Among the eight, pro-neurogenic chemicals, pharmacological testing gave evidence that only one of the compounds had favorable pharmacological properties. Pool seven (P7) contained an aminopropyl carbazole as its active, third compound (C3). When administered to mice via intraperitoneal (IP), intravenous (IV) or oral routes, the P7C3 compound revealed favorable half-life, volume of distribution and brain penetration. It was also found that P7C3 could be safely administered to mice and rats for prolonged periods at concentrations well above those required to stimulate hippocampal neurogenesis, giving evidence that the molecule was not overtly toxic to rodents.

Although it was initially anticipated that pro-neurogenic compounds would act by stimulating the mitotic birth of newborn nerve cells in the subgranular layer of the dentate gyrus, P7C3 revealed no such activity. The two-fold enhanced level of BrdU-positive neurons observed over a week-long dose of P7C3 was absent when animals were pulsed with BrdU for only 24 hours. More strikingly, when BrdU was pulsed for only one day, and animals were subsequently administered P7C3 for a month, we observed a far larger enhancement in BrdU-positive hippocampal neurons (500%). Instead of stimulating the mitotic division of neuronal stem cells, these observations gave evidence that P7C3 mitigated the death of newborn neurons. Under the conditions of our study only 10-20% of newborn neurons survive the month-long differentiation process to become properly wired hippocampal neurons. Prolonged administration of P7C3 significantly mitigated the death of newborn neurons, such that upwards of half of the cells survive the month-long "differentiation gauntlet" taking place between stem cell mitosis and terminal nerve cell differentiation. Indeed, localized expression of pro-apoptotic proteins in newborn neurons has been found to limit neurogenesis, whereas expression of anti-apoptotic proteins enhances neurogenesis in adult mice (Kim et al., 2009) (Kuhn et al., 2005) (Sun et al., 2004). It has likewise been found that the pro-neurogenic benefits of wheel running and/or enriched environment for caged rodents is primarily attributable to neuroprotective effects on newborn hippocampal neurons (Kempermann et al., 1997; Kim et al., 2010) (van Praag et al., 1999).

Having discovered the aminopropyl carbazole chemical in an unbiased, in vivo screen, and having found that it protects newborn neurons from death, we use methods of medicinal chemistry to improve the potency and pharmacological properties of P7C3 (MacMillan et al., 2011; Naidoo et al., 2014; Pieper et al., 2014). Using these improved, active derivatives of P7C3 we have observed neuroprotective activity in animal models of Parkinson's disease (De Jesus-Cortes et al., 2012), amyotrophic lateral sclerosis (Tesla et al., 2012), as well as concussive injury to the rodent brain (accompanying manuscript). Of significant concern, however, was the fact that the mechanism of action of the P7C3 class of neuroprotective chemicals remained unknown. Here we provide evidence that these chemicals function by enhancing the activity of the rate-limiting enzyme in the salvage of nicotinamide adenine dinucleotide (NAD) from nicotinamide.

Results

Figure 8:
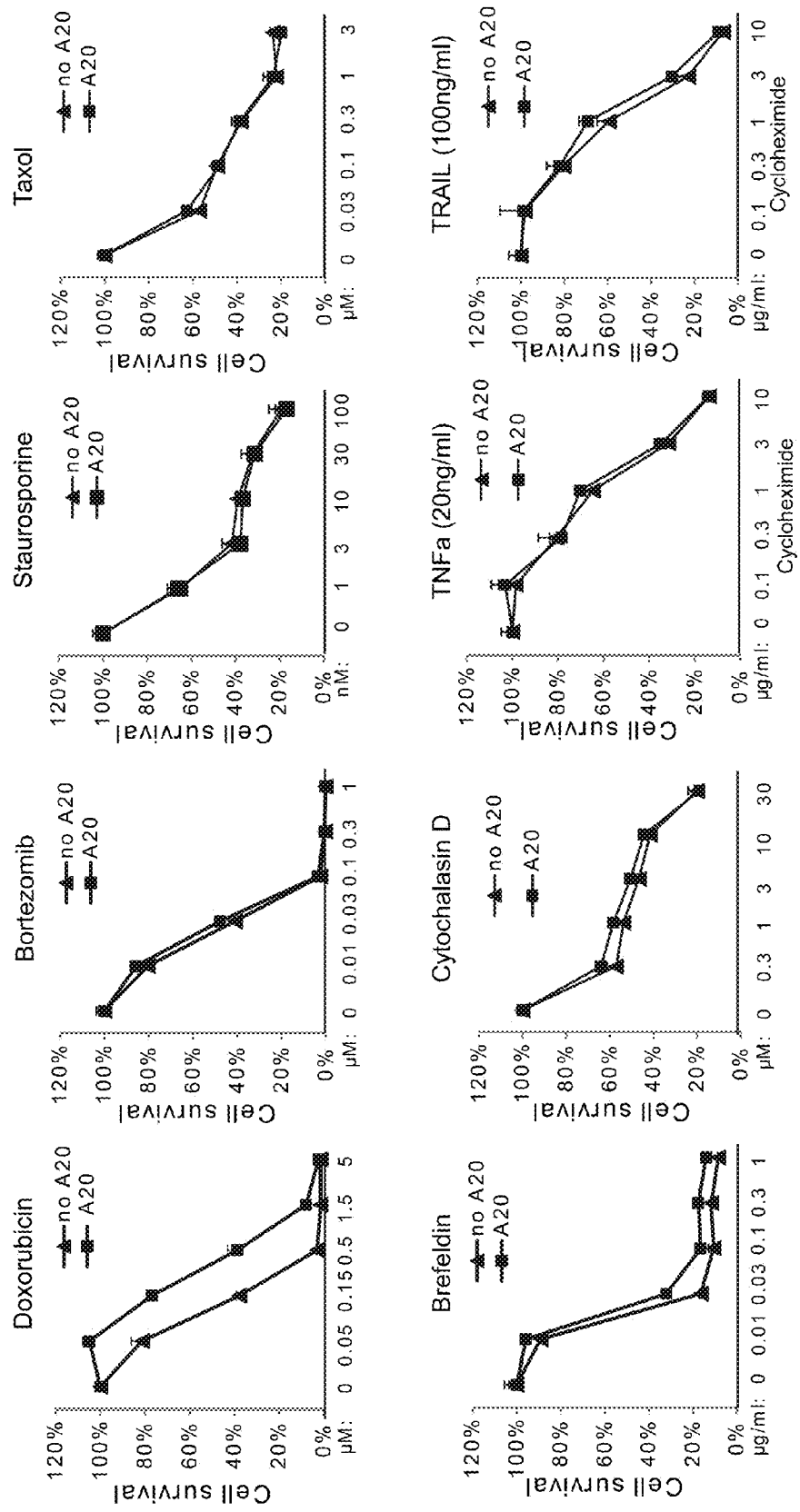
FIG. 8. P7C3A20 protects U2OS cells from doxorubicin-mediated toxicity. U2OS cells were treated with 5 µM P7C3-A20 for 2 h prior to incubation with the indicated concentrations of eight toxins for 72 h.
Figure 9:
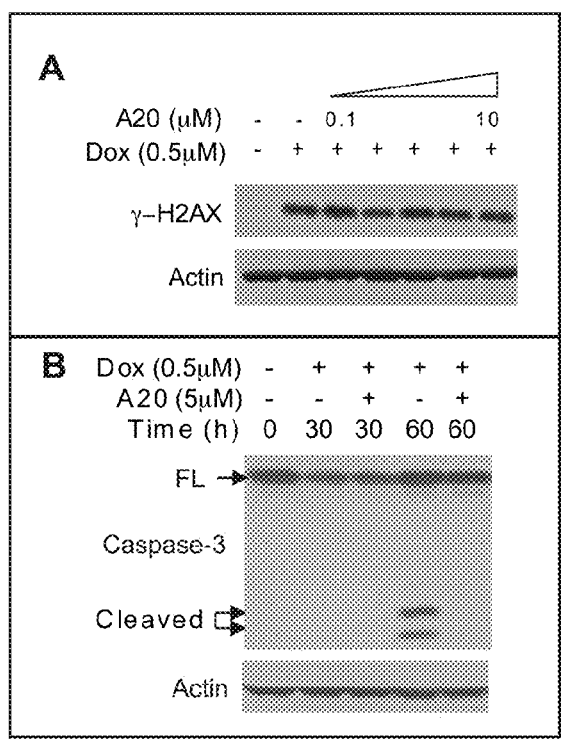
FIGS. 9A-9B. P7C3A20 blocks apoptosis, but not DNA damage response induced by doxorubicin.

Active Variants of P7C3 Protect Cultured Cells from Doxorubicin-Mediated Toxicity Progress on studies aimed towards resolving the mode of action of P7C3 has been hampered by the fact that we have been limited to studies of drug action in living animals. Our standard assay of neurogenesis requires, under optimal conditions, a one month turn-around from the synthesis of a new derivative to a score for its neuroprotective activity. In efforts to break this logjam, we tested whether P7C3 might have cell-protective activity to any of eight generic toxins. The active A20 variant of P7C3 was found to protect cultured U2OS cells from doxorubicin-mediated toxicity (FIG. 1A). By contrast, no evidence of drug-mediated protection was observed for any of seven other toxins (FIG. 8). Furthermore, as judged by the DNA damage marker—phosphorylation of H2AX, and the hallmark of apoptosis—caspase-3 activation, co-administration of A20 blocked doxorubicin-induced apoptosis, but not DNA damage response (FIG. 9).

Figure 10:
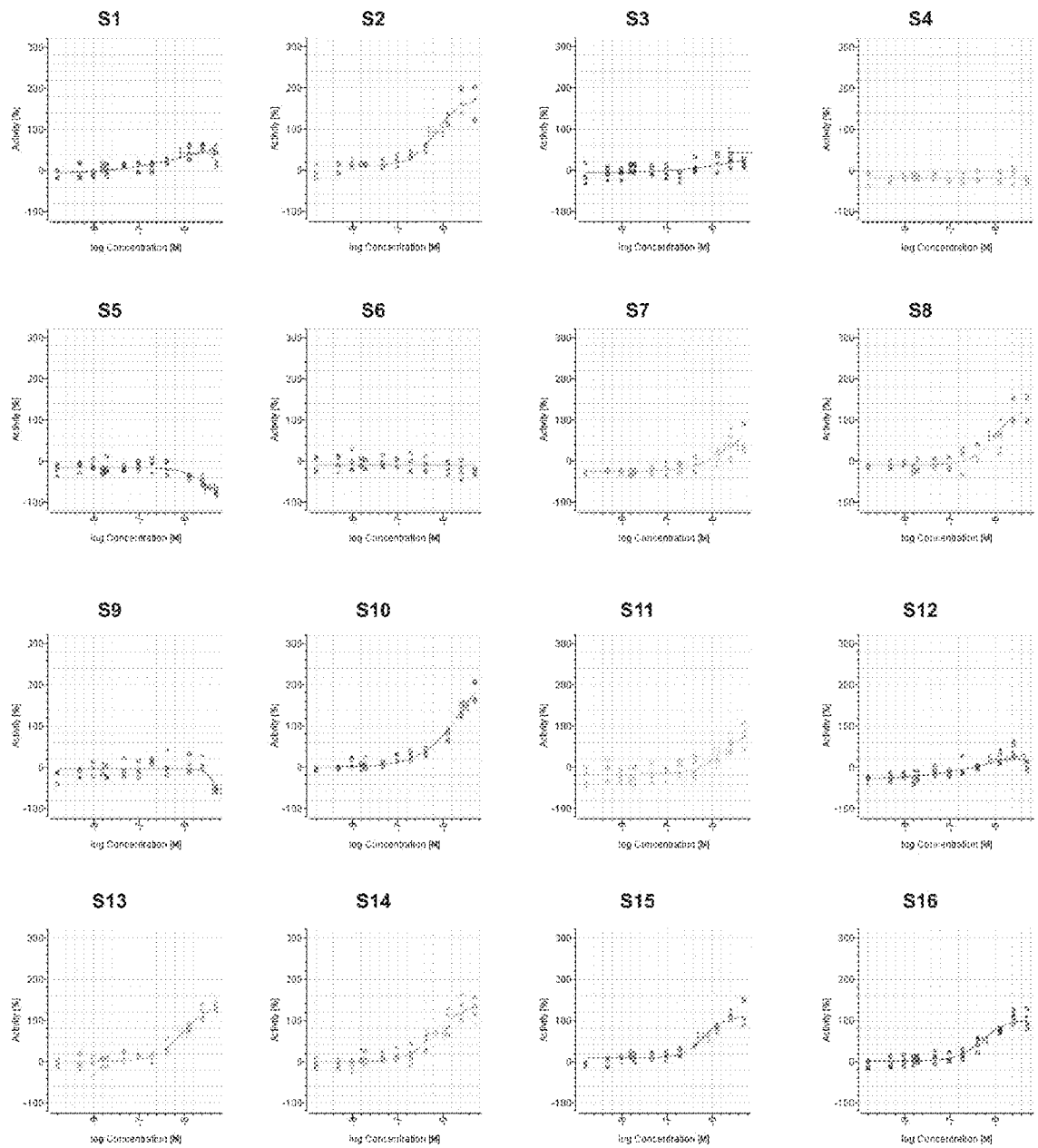
FIG. 10. Twelve-point dose response curves (DRC) of all tested compounds in doxorubicin toxicity protection assay. The cells were grown in 384-well plates and treated with 5 µM-1.7 nM (3-fold serial dilution) of various P7C3 derivatives together with 0.5 µM doxorubicin for 72 h. Cell viability was determined by Cell Titer Glo assay kit.
Figure 10:
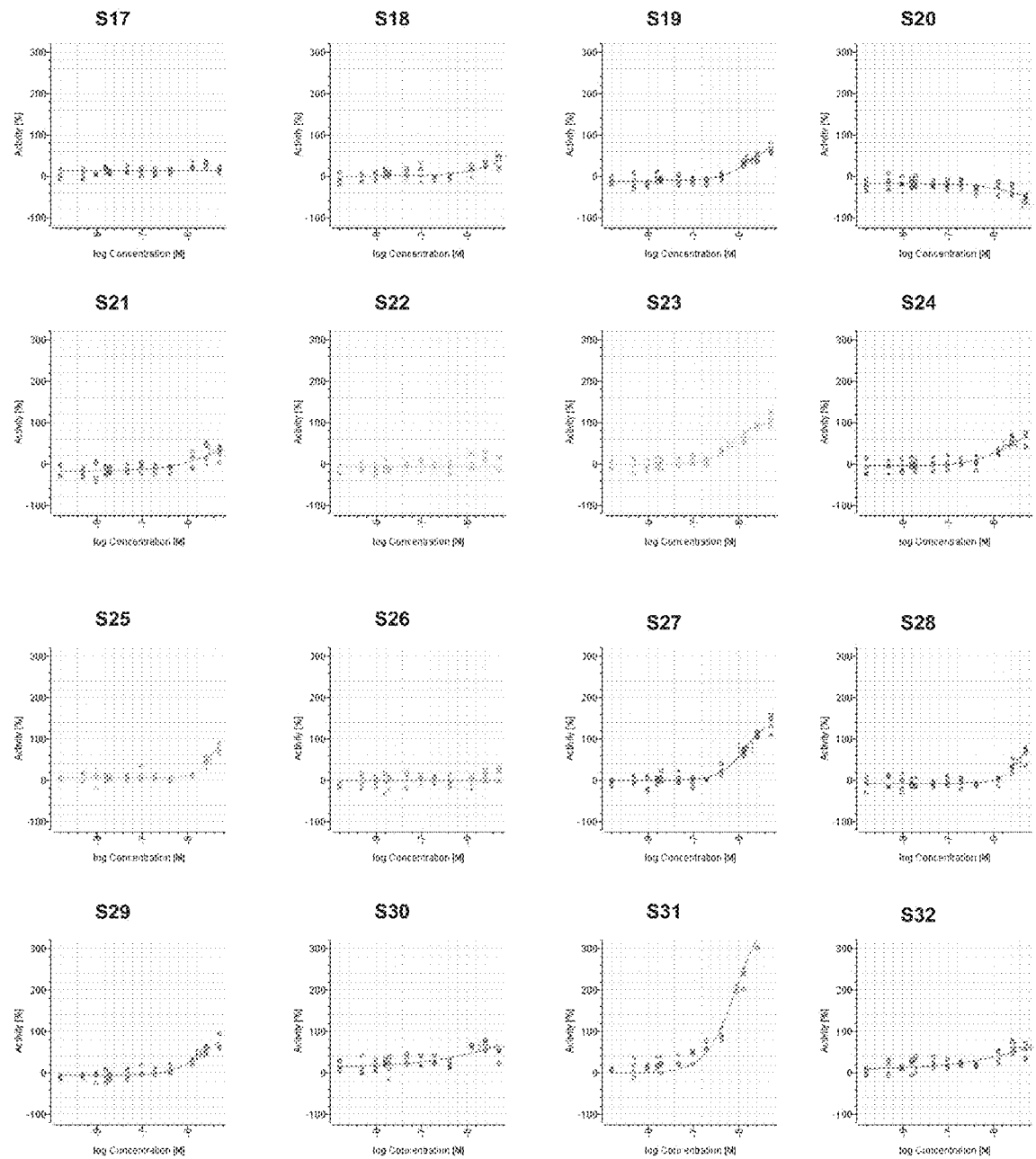
Figure 10:
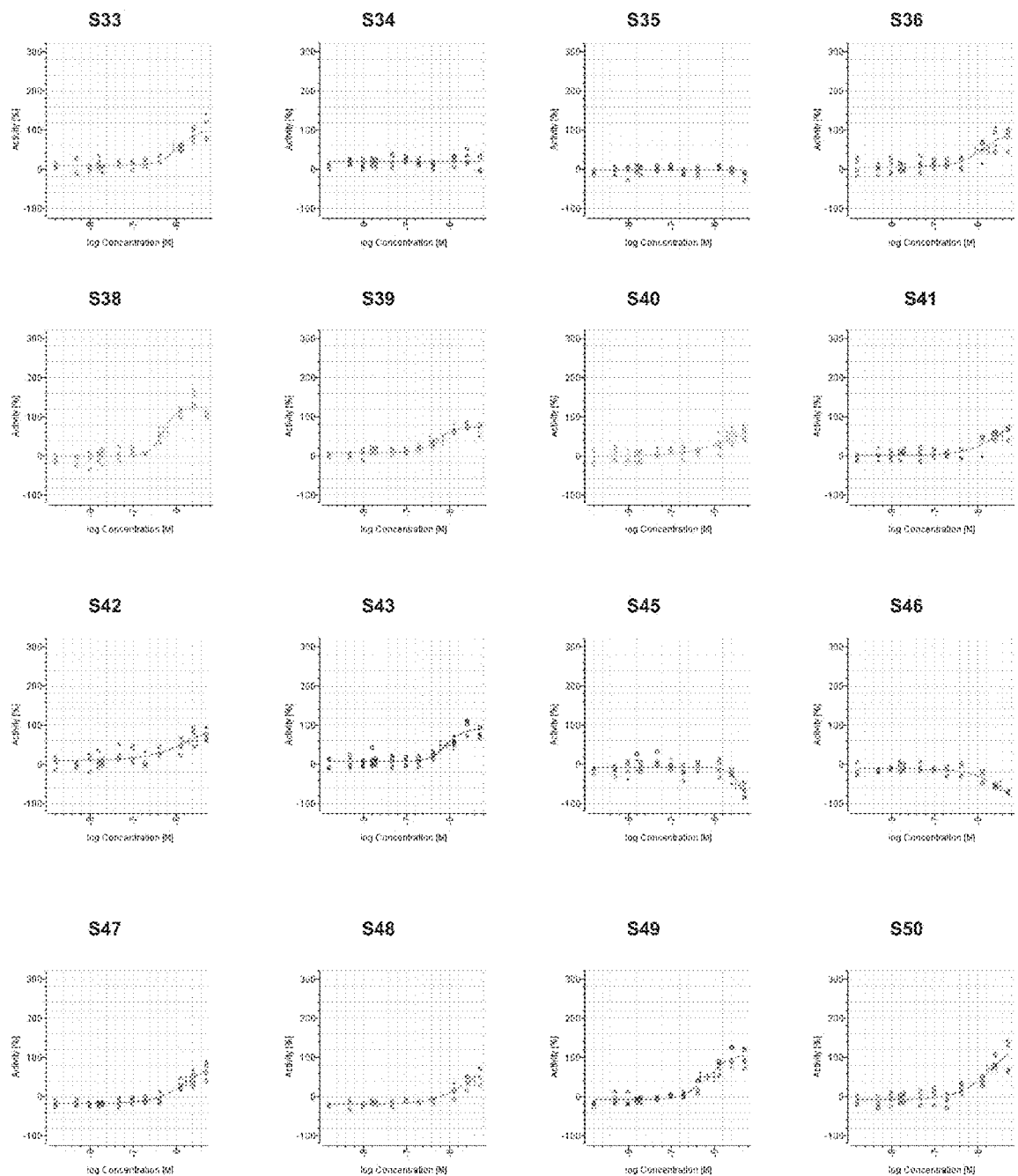
Figure 10:
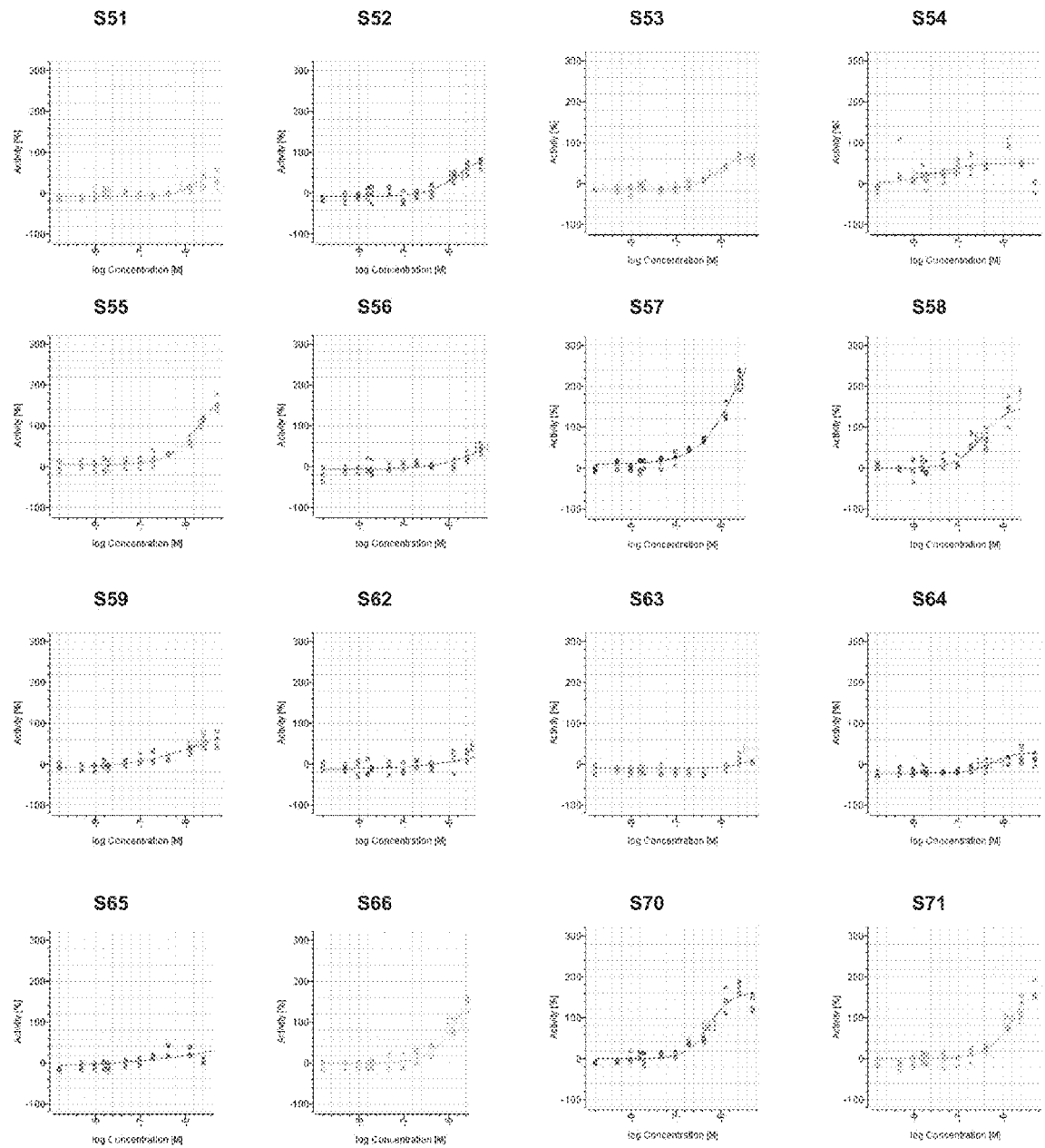
Figure 10:
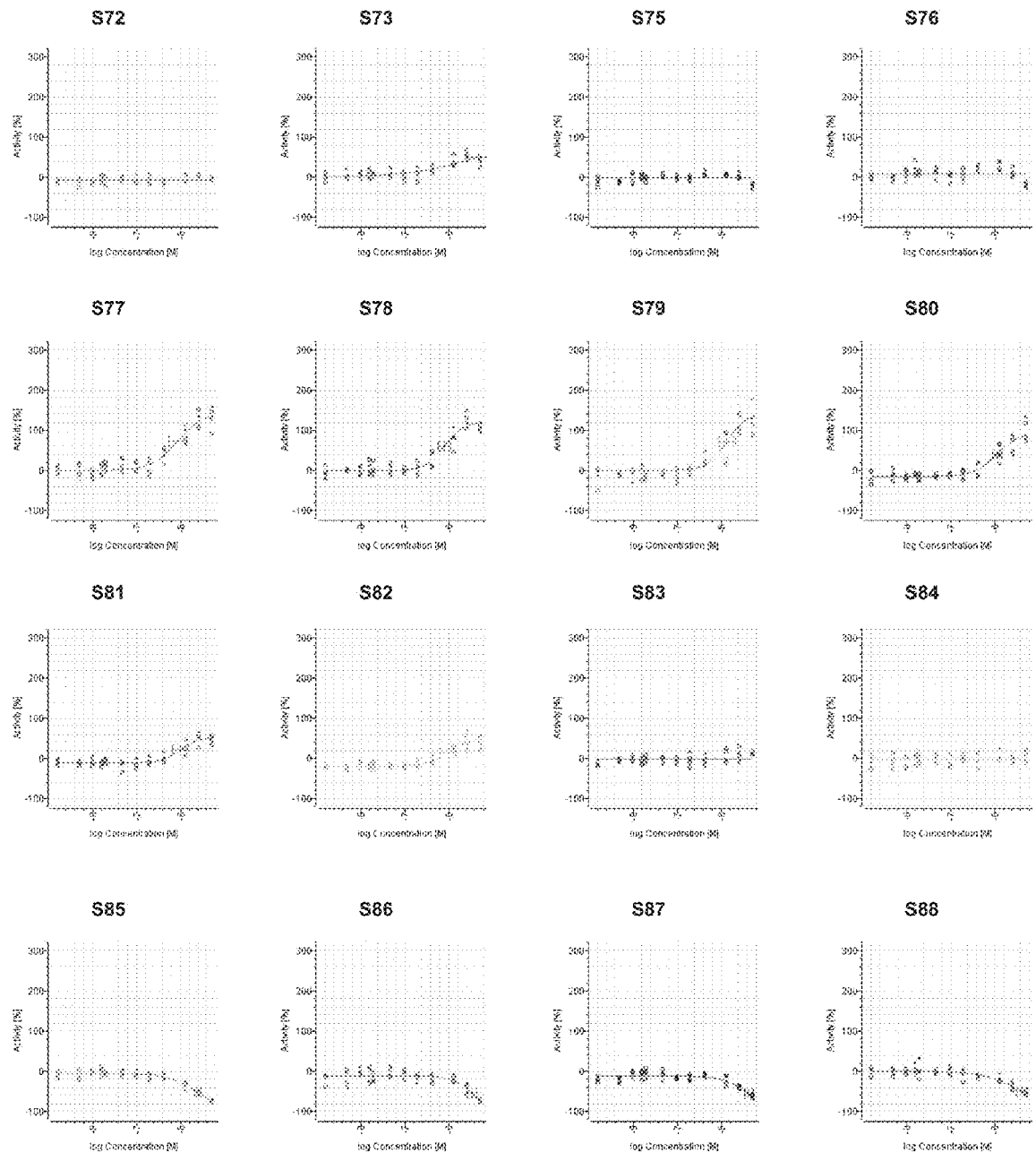
Figure 10:
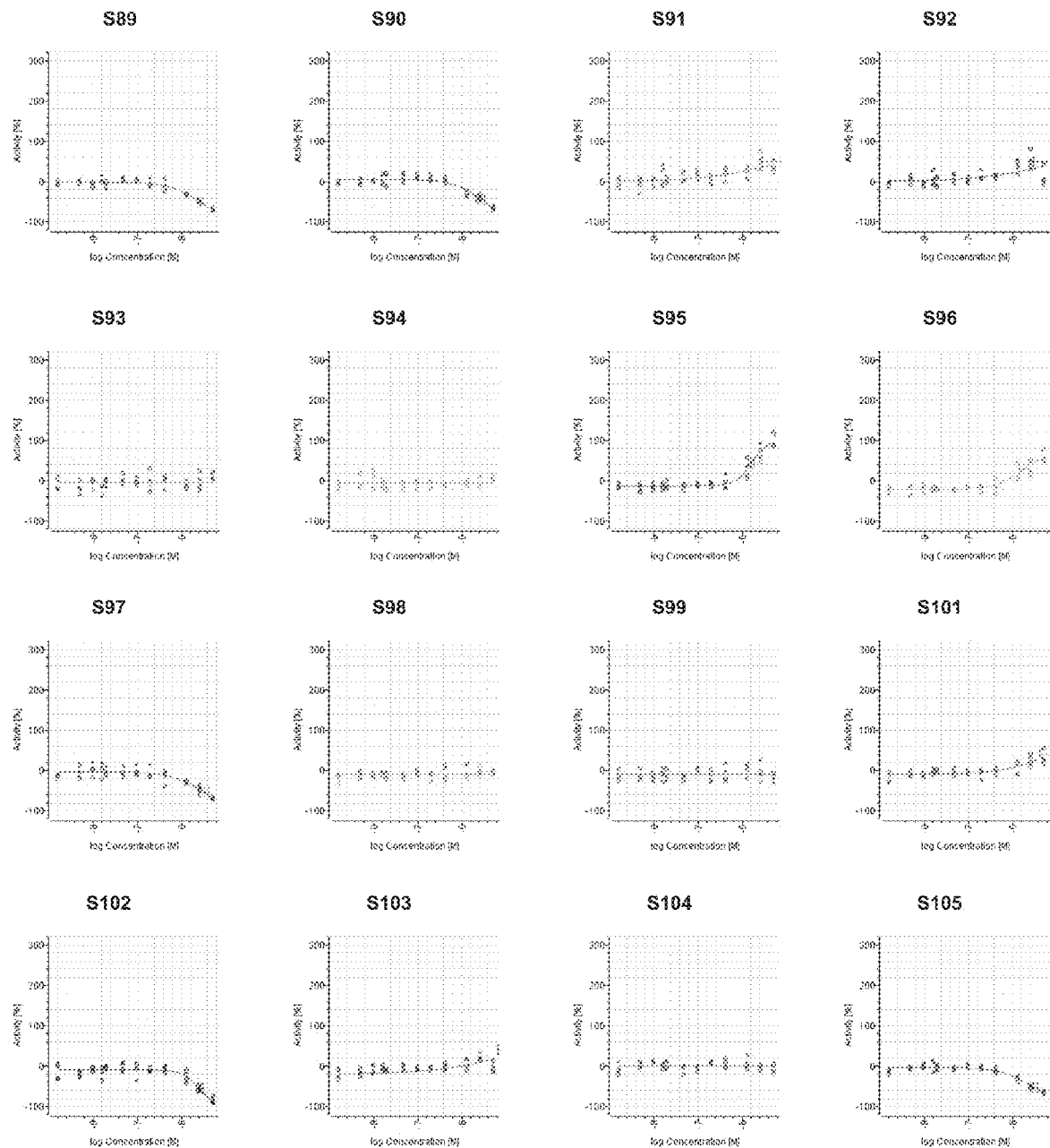
Figure 10:
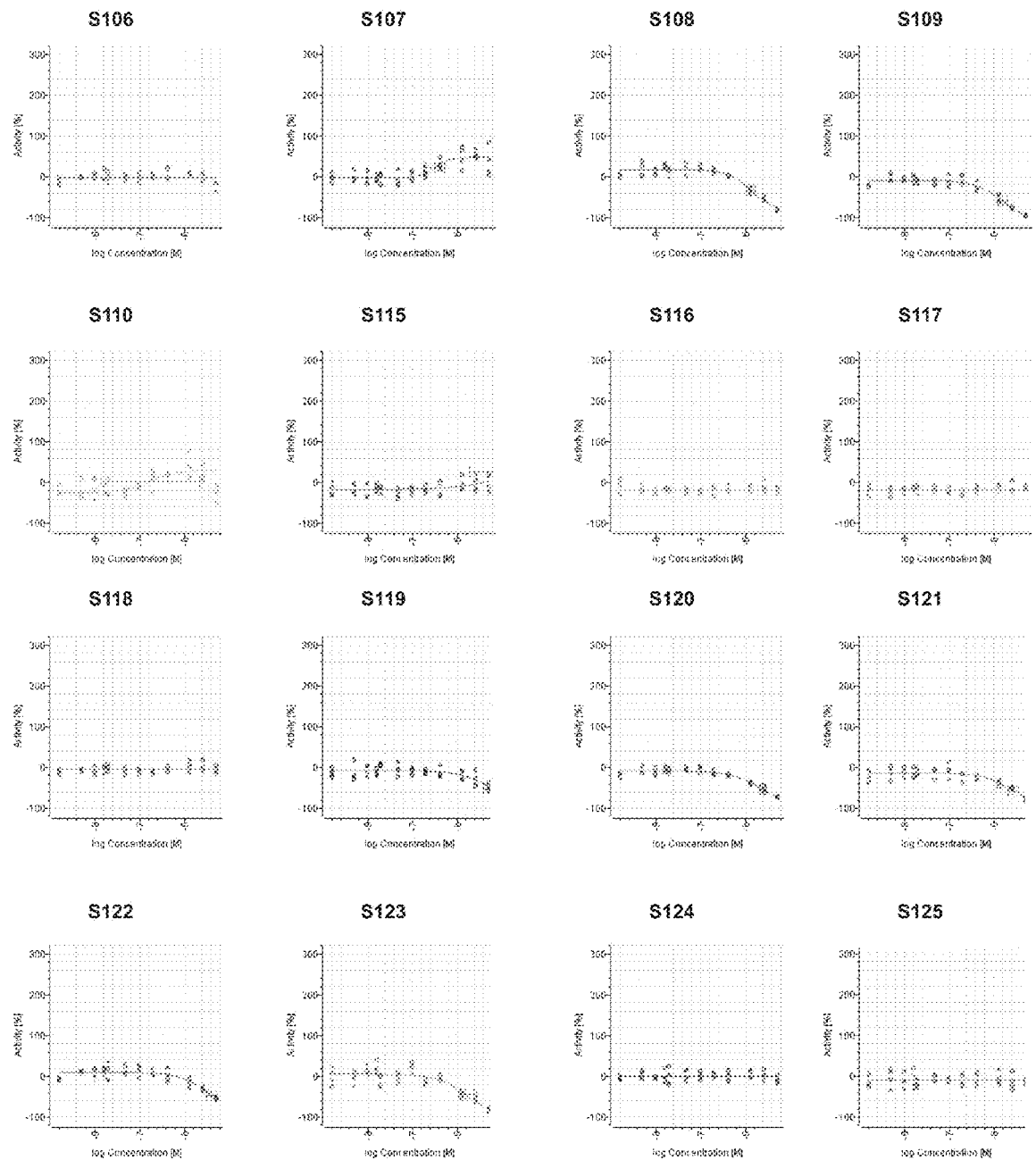
Figure 10:
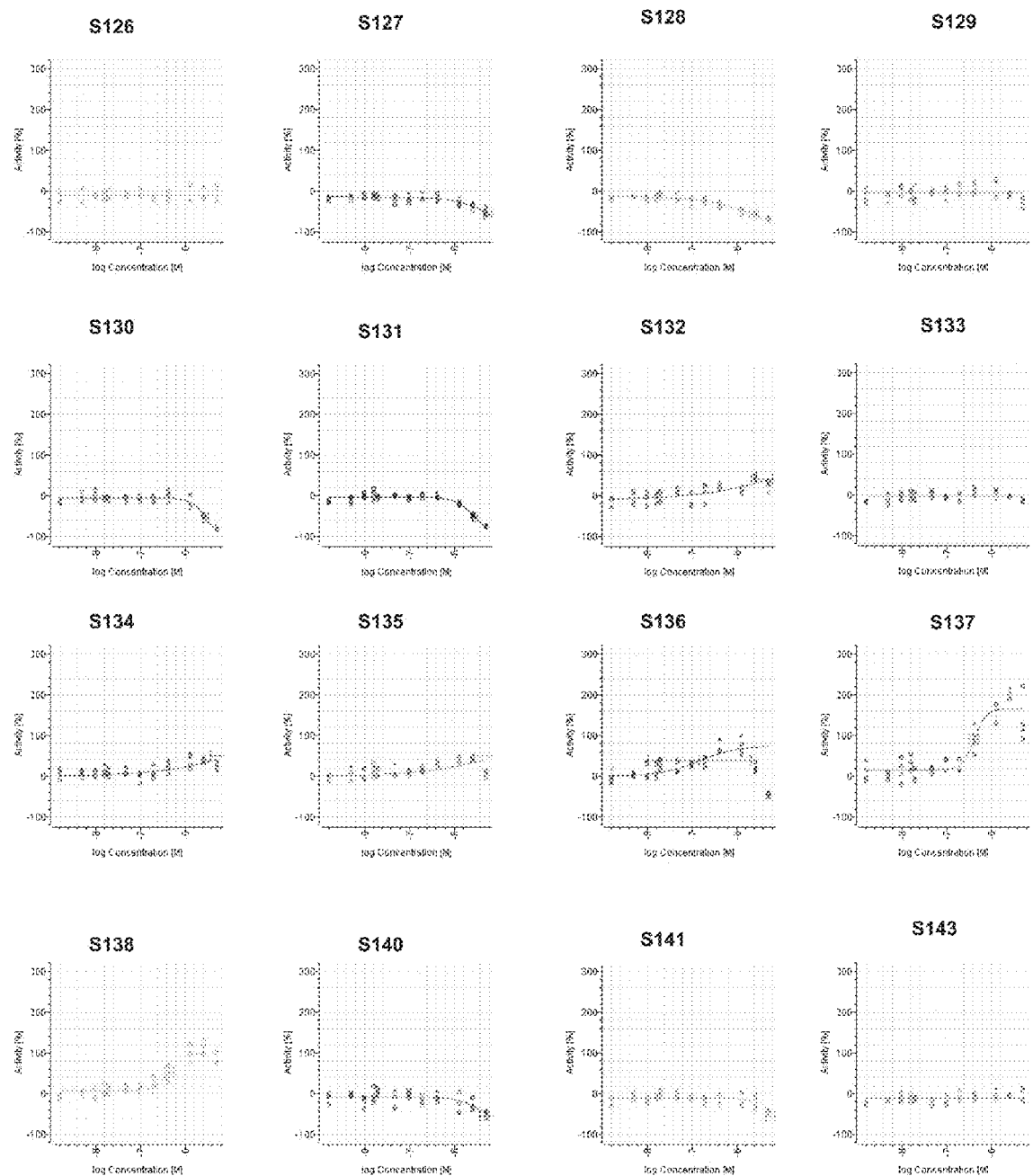
Figure 10:
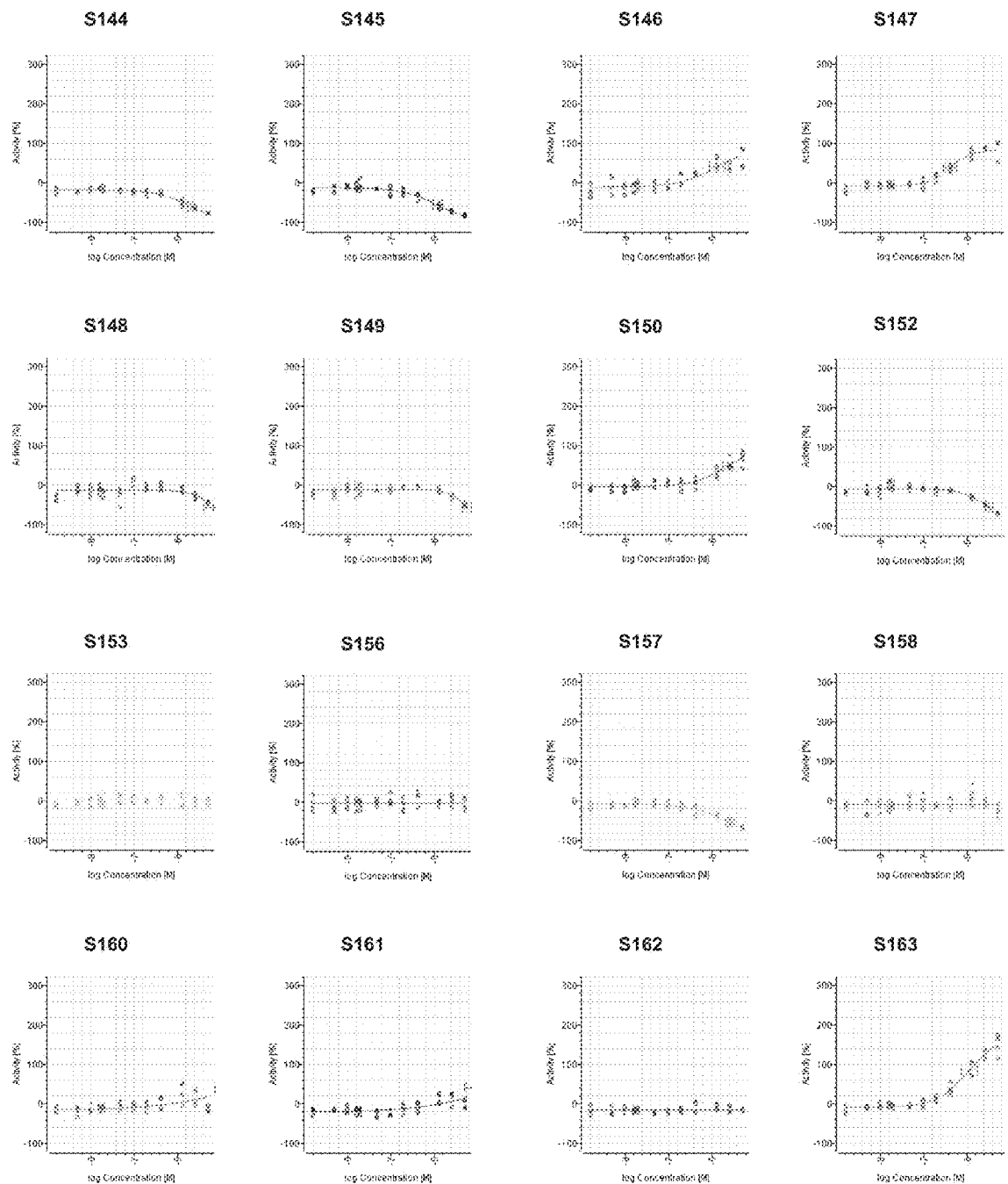
Figure 10:
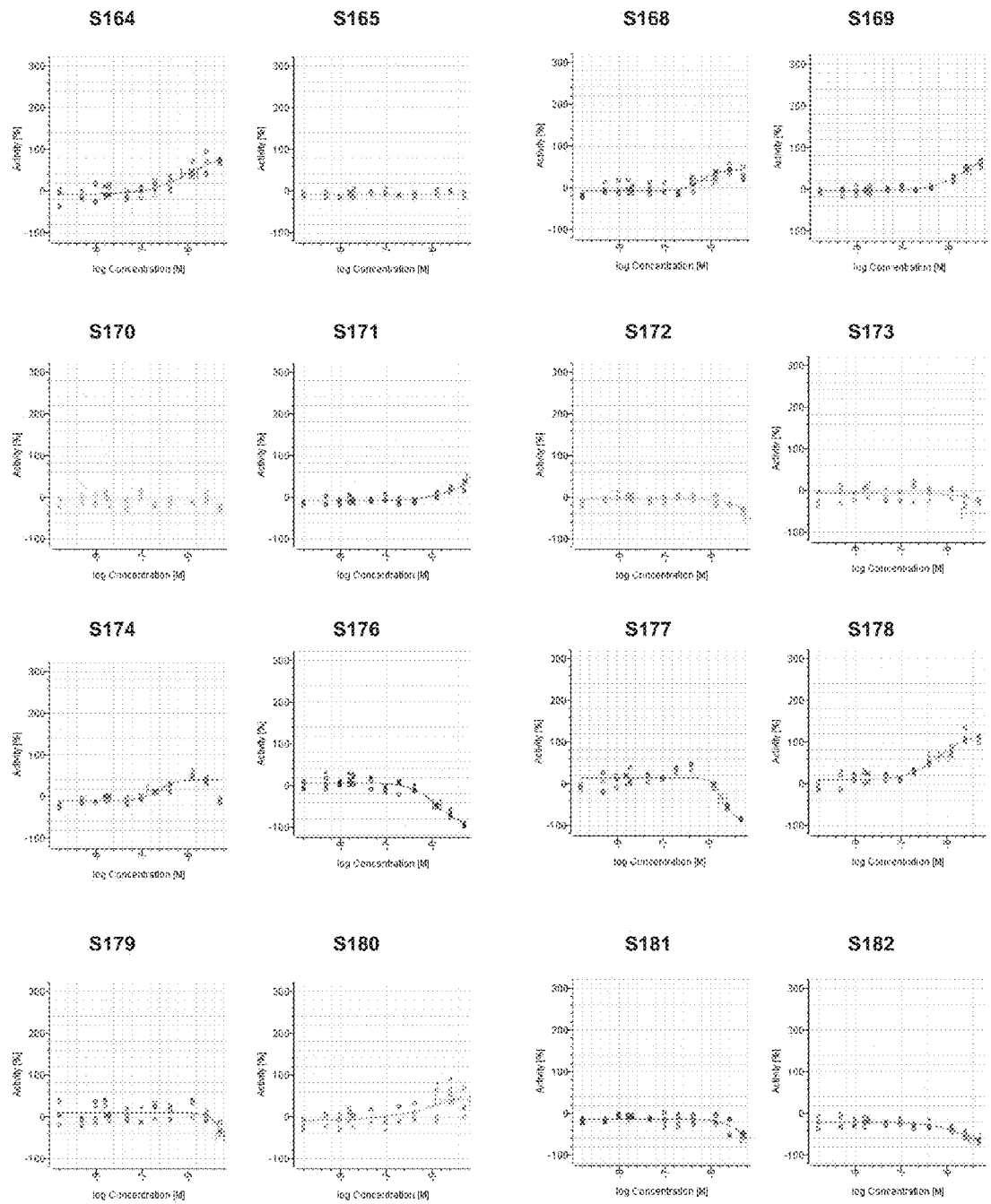
Figure 10:
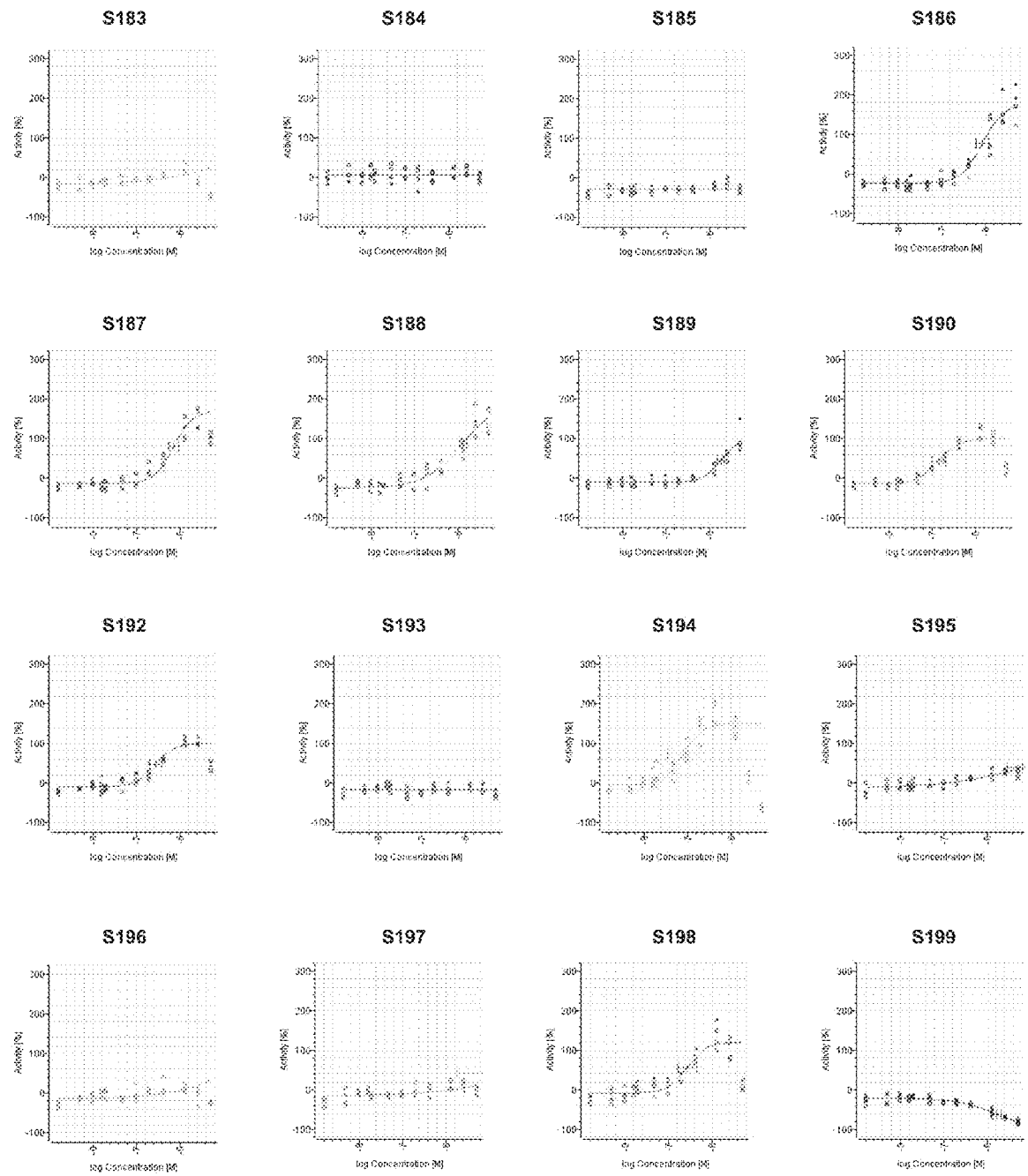
Figure 10:
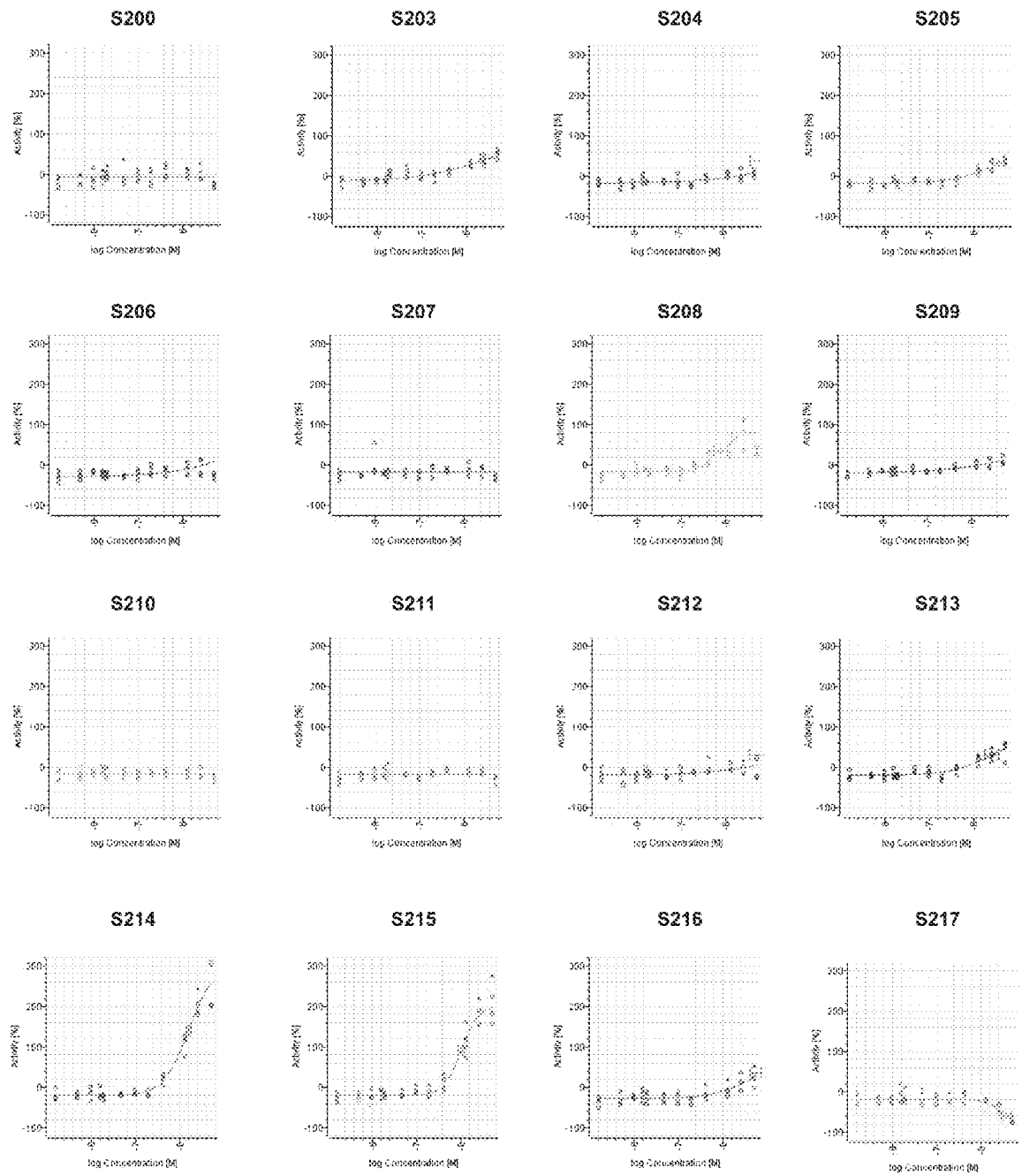
Figure 10:
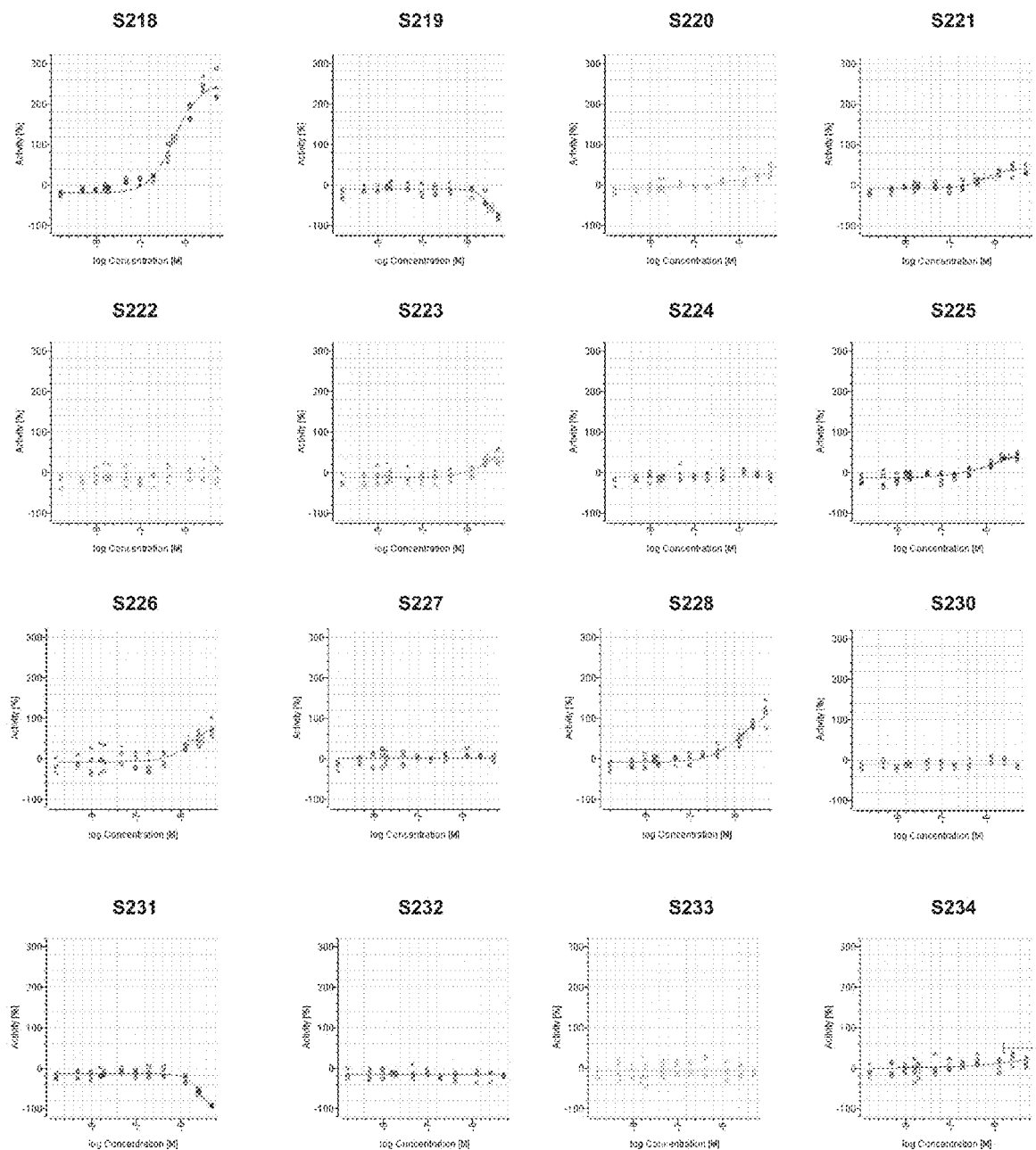
Figure 10:
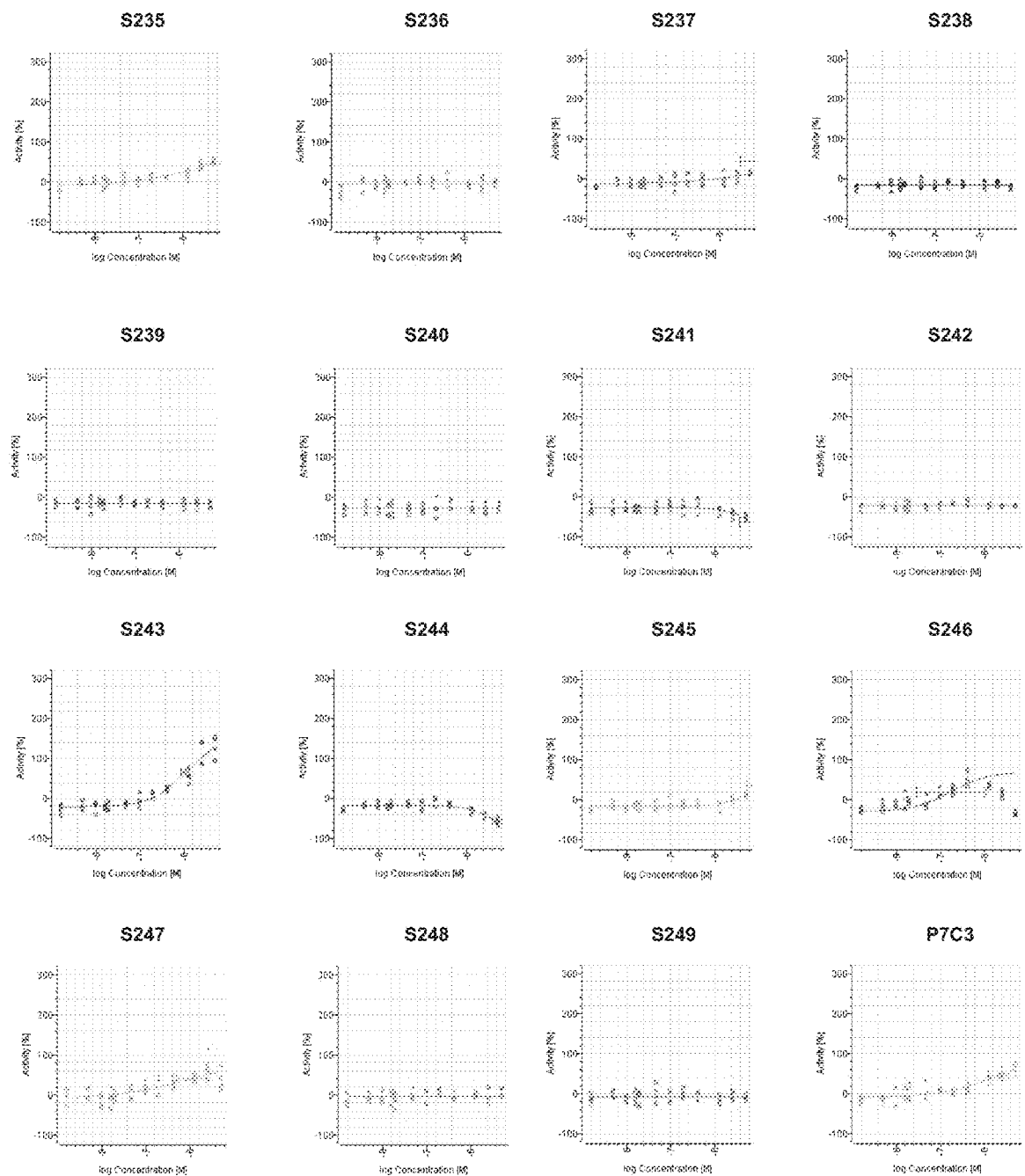
Figure 10:
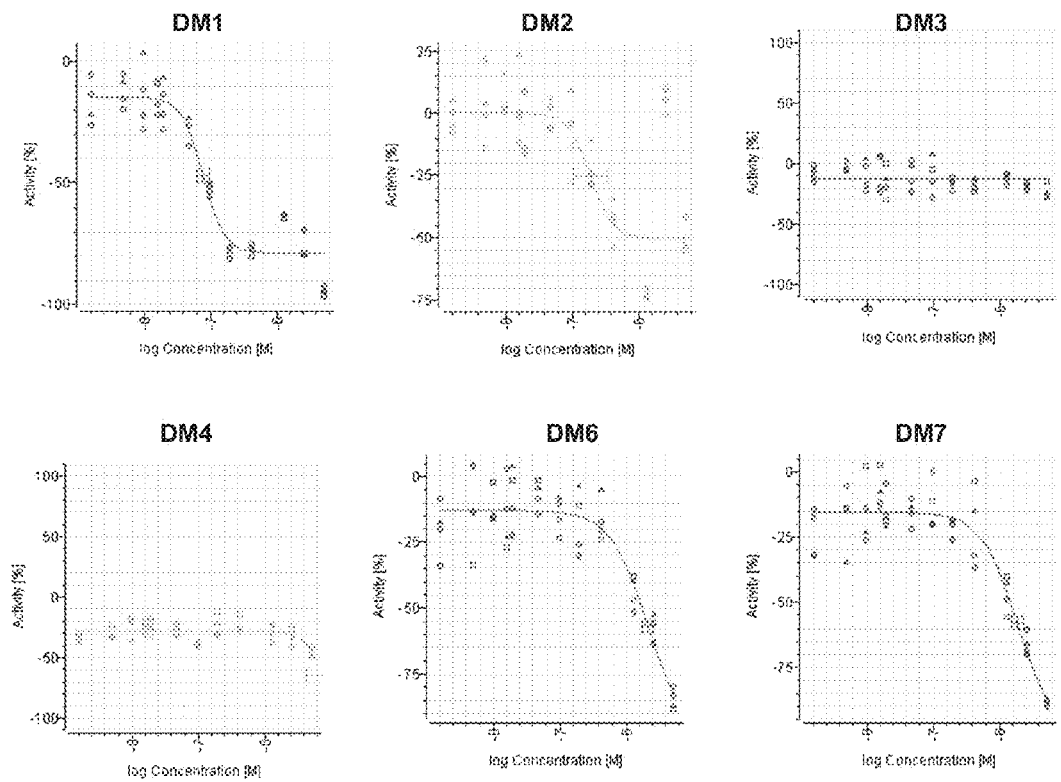

In order to assess whether a correlation might exist between pro-neurogenic activity in living mice and doxorubicin toxicity (dox:tox) protection, we assayed 224 compounds that have been synthesized and assayed for pro-neurogenic activity over the past 4-5 years (Table 1). These include hundreds of structure:activity relationship (SAR) derivatives of P7C3, as well as a number of tricyclic antidepressants reported in the literature to have pro-neurogenic activity (Malberg et al., 2000). P7C3 derivatives were the only molecules having dox:tox protective activity (FIG. 10). Further inspection of the data revealed that the chemical features of the carbazole ring, length of the aliphatic linker, and nature of the aromatic ring were all important determinants for both pro-neurogenic activity and dox:tox protection. Perhaps most compellingly, it was observed that the (−)-P7C3-S243 enantiomer that was active in the in vivo neurogenesis assay (Naidoo et al., 2014), the MPTP model of Parkinson's disease (Naidoo et al., 2014), and the concussive blast injury model (co-submitted manuscript) was also protective in the dox:tox assay (FIG. 1B). By contrast, the (+)-P7C3-S243 enantiomer that was far less active in the three in vivo assays of neuroprotection was also considerably less active in the dox:tox protection assay. From these observations we conclude that active derivatives of P7C3 function by a related mechanism to protect neurons in living animals as well as cultured U2OS cells exposed to doxorubicin.

Identification of p70 and p55 as Intracellular Targets of P7C3

Figure 2:
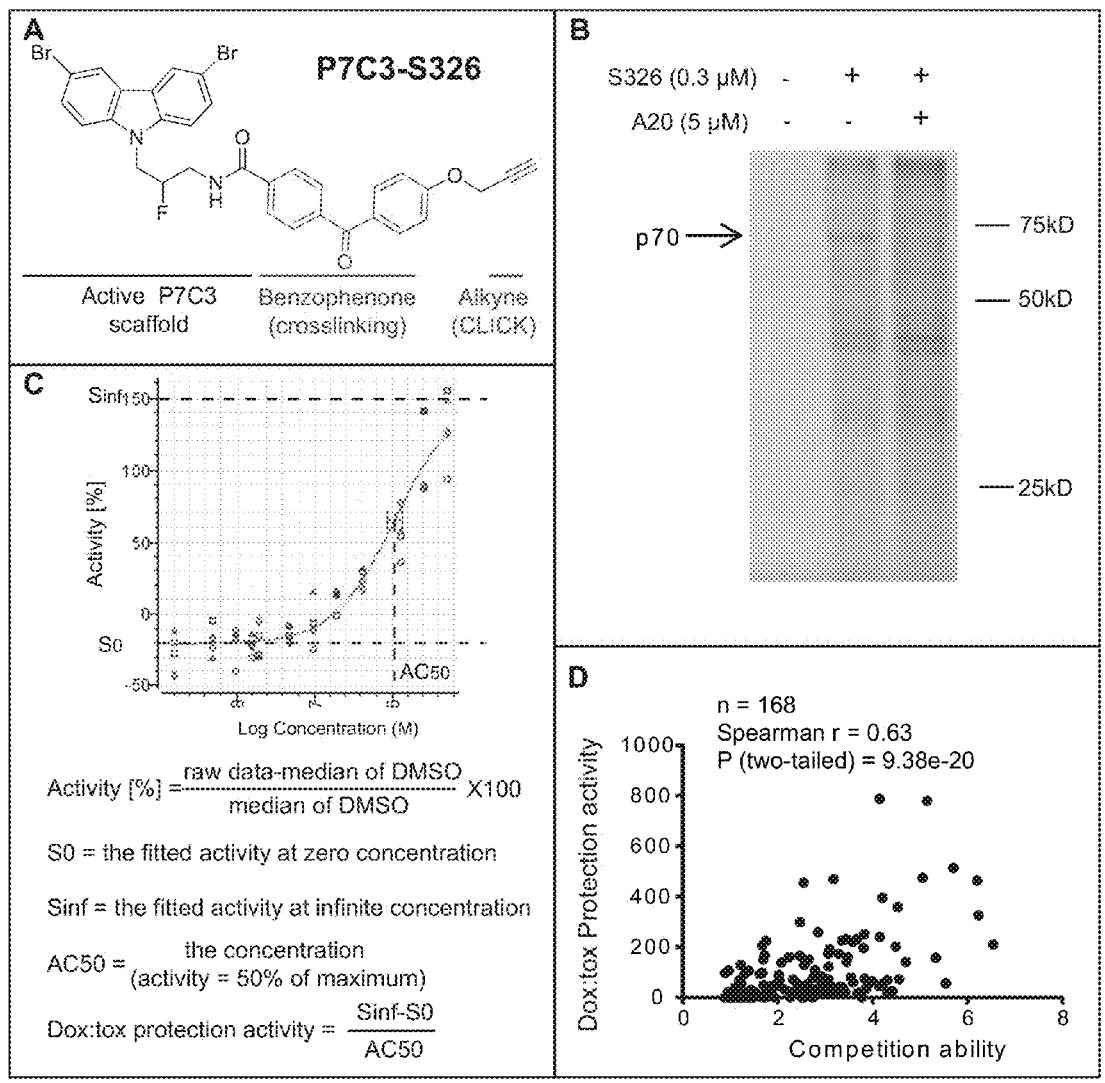
FIGS. 2A-2D. Identification of the P7C3 binding protein p70 using the P7C3-S326 photo-crosslinking probe.

Various methods have been employed in efforts to identify the intracellular target of P7C3, including biotinylation followed by affinity purification, radiolabeling followed by filter binding assays, and photo-crosslinking. Among these strategies, the photo-crosslinking approach has been uniquely successful. P7C3-S326 was prepared to contain both a benzophenone for photo-crosslinking and an alkyne moiety for use in click chemistry (FIG. 2A). This derivative was found to be active in both the in vivo neurogenesis assay and the dox:tox assay. When incubated with cultured cells, exposed to UV light, subjected to click chemistry-mediated addition of a fluorescent dye, then resolved on SDS polyacrylamide gels, the P7C3-S326 derivative became covalently attached to roughly a dozen proteins. Among the covalently modified proteins, only one could be competed when the cells were co-incubated with a 30× excess of the active A20 variant of P7C3. This polypeptide exhibited an apparent molecular mass of 70 kD (FIG. 2B).

Figure 11:
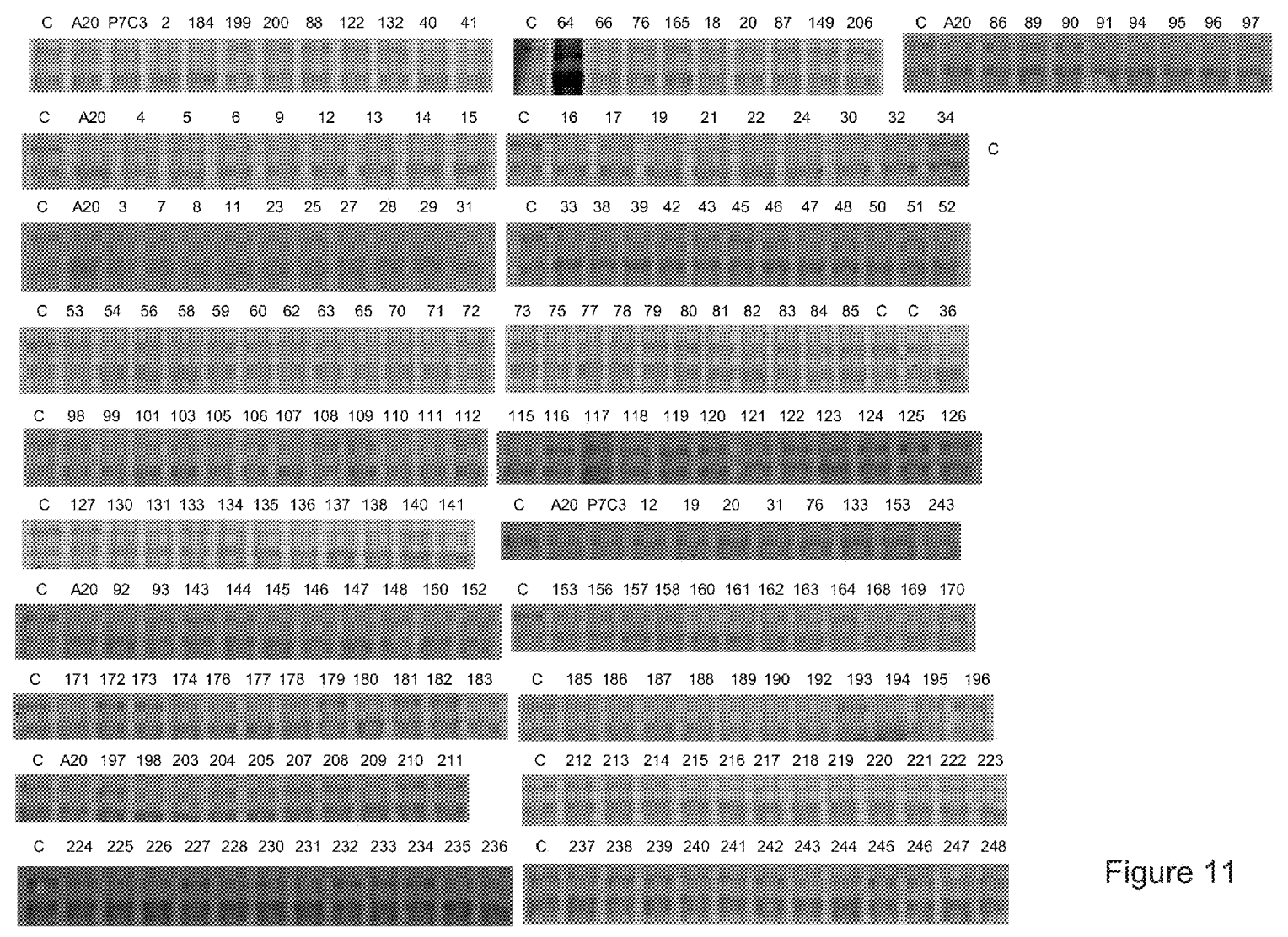

Binding competition assays were conducted with 168 chemical derivatives of P7C3 as a means of testing whether there might be a correlation between dox:tox protection and binding competition. Cultured cells were co-exposed to P7C3-S326 (0.3 uM) and the individual P7C3 variants (5 uM), exposed to UV light, lysed, clicked to a fluorescent dye and run on SDS gels (FIG. 11). The scatter plot shown in FIG. 2D revealed a statistically significant correlation between the two activities, yielding a P value of $9.4\times10^{-20}$. It can thus be predicted with a high level of confidence that active variants of P7C3 are able to compete for P7C3-S326 crosslinking, but that inactive variants cannot. Armed with this knowledge, cell fractionation experiments were performed in order to enrich for the p70 band. During the course of these studies it was periodically observed that P7C3-S326 could also be crosslinked to a second band running with an apparent molecular weight of 55 kD. Just as was the case for p70, active variants of P7C3 competed for p55 binding, whereas inactive variants did not. Moreover, both proteins co-purified with a cellular fraction following centrifugation at 12,000 G.

The p70 and p55 Targets of P7C3 Correspond to NAMPT

Figure 3:
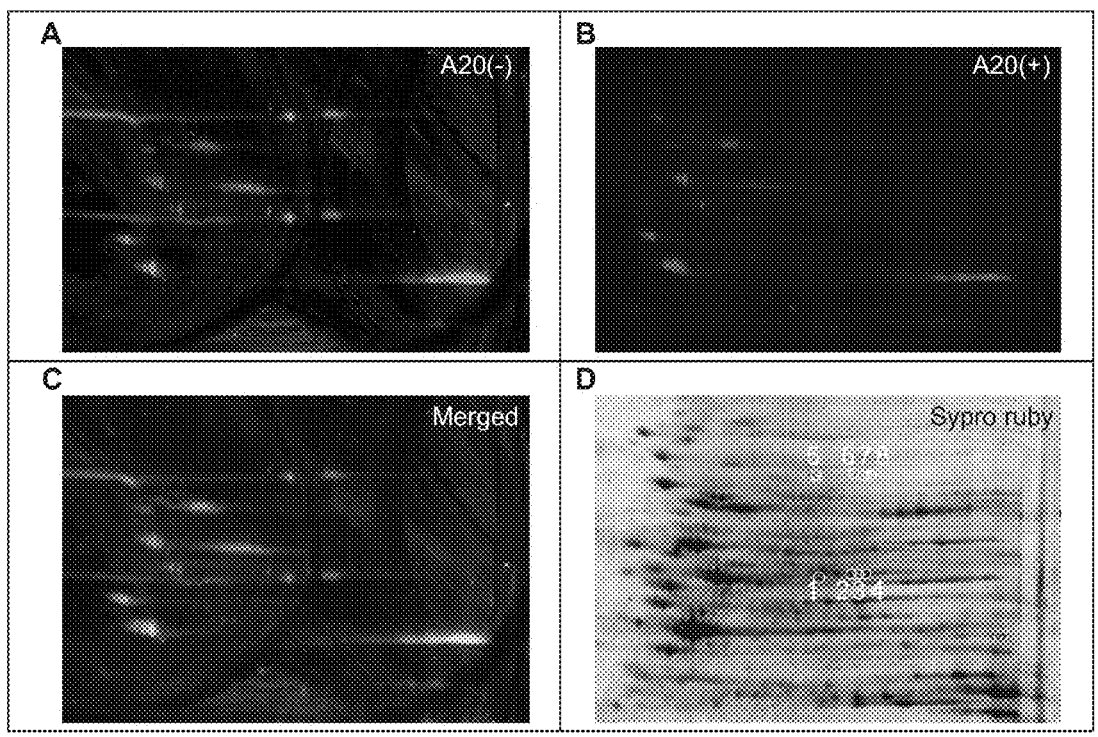

Partially purified protein preparations were resolved by 2D gel electrophoresis. In order to discriminate between protein spots competed by an excess of the active, A20 variant of P7C3, and those that were not, separate lysates were prepared from cells that had been co-exposed to the P7C3-A20 competitor or not. Click chemistry was used to append a red fluorescent dye onto P7C3-S326-modified proteins of the former lysates (Kolb et al., 2001). The latter lysates were modified by a green dye, such that in imaging 2D gels, we could focus on green protein spots and avoid spots labeled by both green and red dyes. Such efforts led to the identification of green-only spots migrating at either 70 kD or 55 kD (FIGS. 3A-3C). Proteins of both molecular weights migrated in the isoelectric focusing dimension at four closely spaced pH positions. This electrophoretic behavior might be consistent with post-translational modifications of the same protein, leading to different isoforms bearing slight differences in ionic charge. Perplexingly, the pattern of charge distribution was identical for the 70 kD and 55 kD polypeptides.

The eight green-only spots, four from p70 and four from p55, were picked and subjected to shotgun mass spectrometry for protein identification. All four of the p55 spots yielded by far the highest number of spectral counts for nicotinamide phosphoribosyltransferase (NAMPT) (Table 2). Both the predicted size (55 kD) and isoelectric point (pH 6.7) of NAMPT match spots 1-4 picked from the 2D gel. Likewise, mass spectrometry based analysis gave substantive percentage coverage levels of 12%, 82%, 38% and 62% for the NAMPT enzyme in spots 1-4 (Table 2). By contrast, no proteins could be identified above the false discovery rate for the four p70 spots. Post-staining of the 2D gel with spyro ruby dye showed prominent protein staining for all four of the p55 spots, and no staining for any of the four p70 spots (FIG. 3D). Apparently, despite equivalent photo-crosslinking by P7C3-S326, the molar ratio of drug modification of p70 must be at least three orders of magnitude greater than p55.

Figure 4:
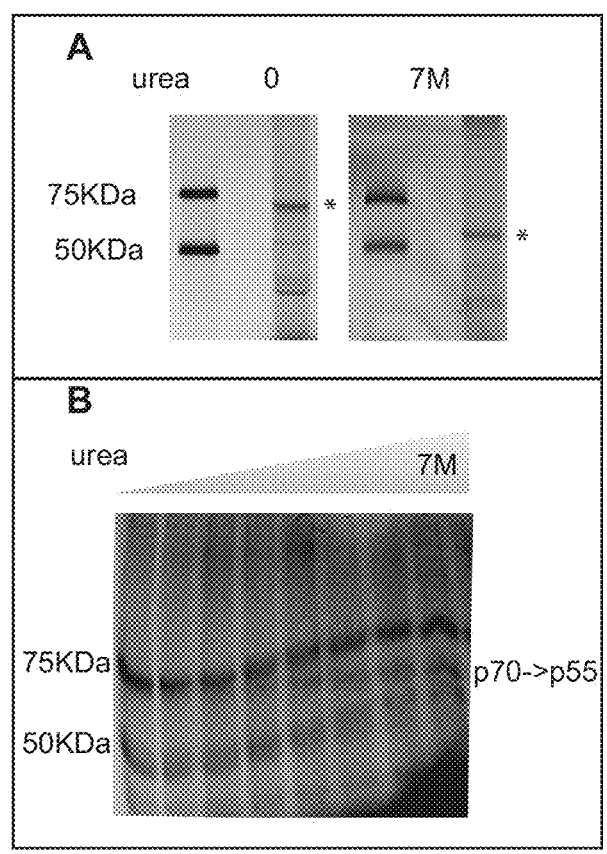
FIGS. 4A-4B. Conversion of p70 into p55 in the presence of urea.

The perplexing relationship between p70 and p55 was clarified upon adding 7M urea to the SDS PAGE gels used to resolve the two bands. In the absence of urea, almost all of the P7C3-S326-modified material migrated as the p70 band. Addition of urea to the gel converted all of the labeled material to the p55 band (FIG. 4A). By running a gel crafted to contain a horizontal gradient of urea, 7M on the right and no urea on the left, it was possible to observe graded conversion of p70 into p55 (FIG. 4B). These observations give evidence that when NAMPT is covalently bound by P7C3-S326, it can adopt an anomalous pattern of electrophoretic migration under gel conditions that are not fully denaturing.

Active Derivatives of P7C3 Restore NAD Levels in Doxorubicin-Treated Cells

Having observed P7C3-S326 crosslinking to both the p70 and p55 forms of NAMPT, we wondered whether active variants of P7C3 might modify the activity of the enzyme. The NAMPT enzyme controls the rate limiting step in the NAD salvage pathway (Preiss and Handler, 1958). NAMPT is an obligate dimer whose molecular structure has been resolved by X-ray crystallography (Khan et al., 2006) (Wang et al., 2006). On the basis of molar ratio of crosslinking, P7C3-S326 strongly prefers the p70 isoform of NAMPT relative to the p55 isoform. Hypothesizing that p70 represents a drug-altered form of NAMPT, we tested whether highly active P7C3-A20 variant might either enhance or reduce NAD levels in living cells.

Figure 5:
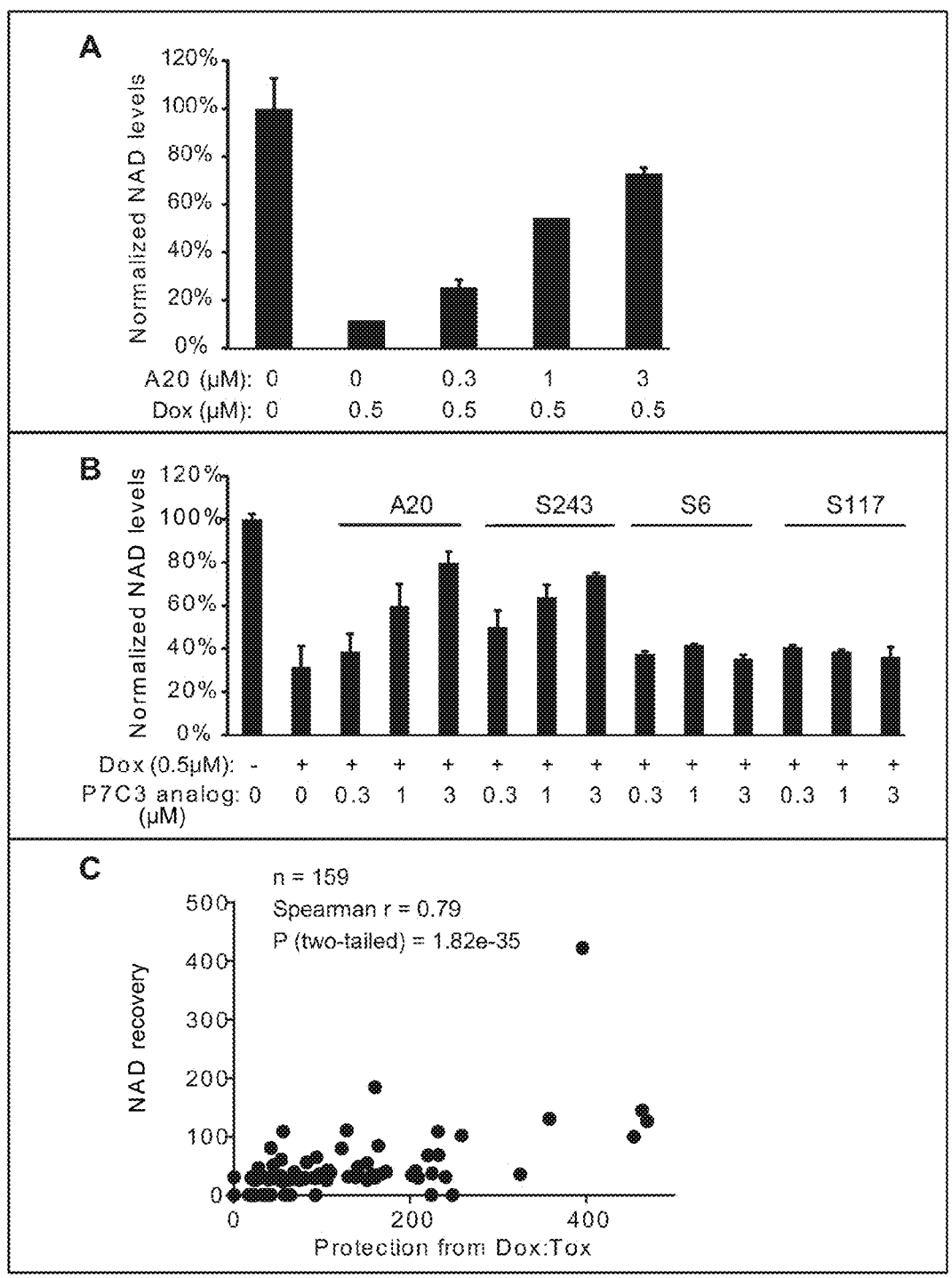
FIGS. 5A-5C. Active variants of P7C3 compensate NAD exhaustion induced by doxorubicin.

Doxorubicin is a DNA-damaging toxin known to activate the poly ADP-ribose polymerase (PARP) enzyme as a central feature of DNA repair (Pacher et al., 2002) (Munoz-Gamez et al., 2009). PARP uses NAD as the donor for poly ADP-ribose synthesis and hence lowers cellular levels of NAD. U2OS cells exposed to sub-lethal levels of doxorubicin were lysed in methanol, cleared by centrifugation and subjected to metabolite analysis by mass spectrometry. These methods allow for the simultaneous, quantitative analysis of hundreds of intracellular metabolites (Tu et al., 2007) (Wang et al., 2009). As expected, doxorubicin treatment led to a significant decline in NAD levels relative to all other metabolites assayed. Co-administration of the A20 variant of P7C3 led to a dose-dependent replenishment of NAD (FIG. 5A). The mass spectrometry methods used to quantitate metabolite levels measured NAD relative to hundreds of other intracellular metabolites. As such, the ability of the A20 variant of P7C3 to restore intracellular levels of NAD does not simply reflect the generalized health of cells, but instead reflects the relative increase in NAD levels compared with hundreds of other metabolites.

Figure 12:
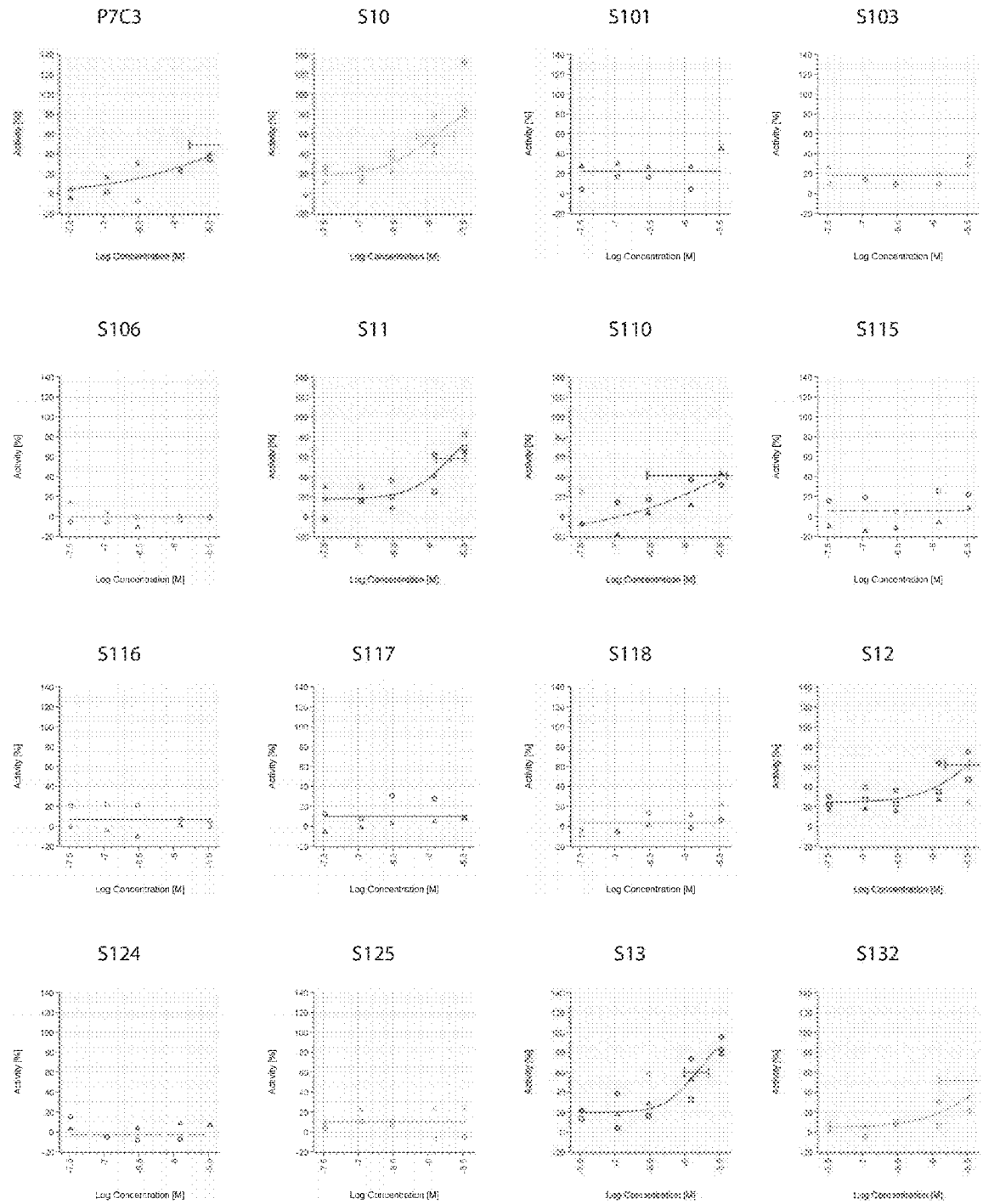
FIG. 12. Five-point dose response curves (DRC) of all tested compounds in NAD rebound assay. Cells were grown in 384-well plates and treated with 5 µM-62 nM (3-fold serial dilution) of various P7C3 derivatives together with 0.5 µM doxorubicin for 45 h. Cellular NAD abundance was determined by NAD/NADH Glo assay kit.
Figure 12:
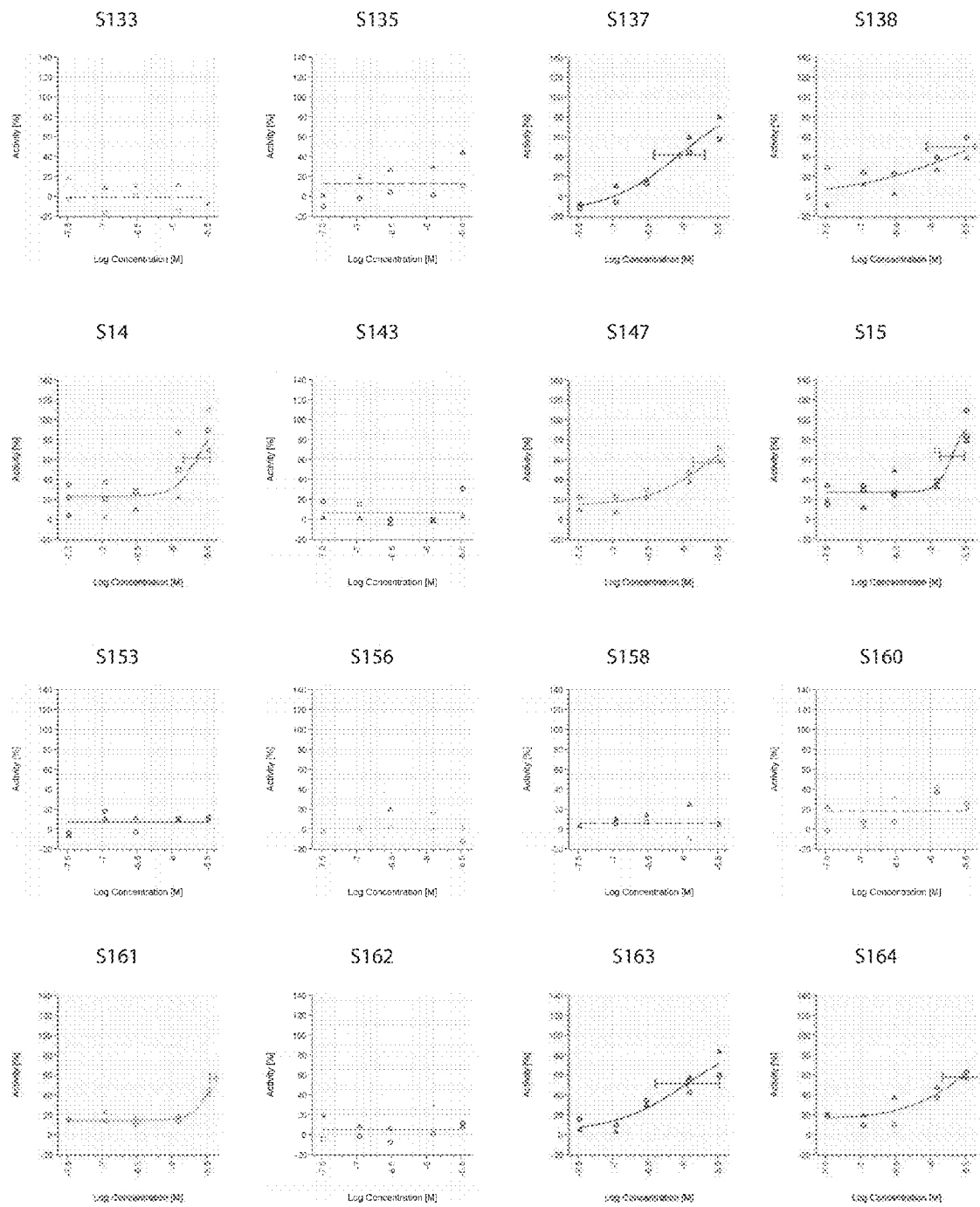
Figure 12:
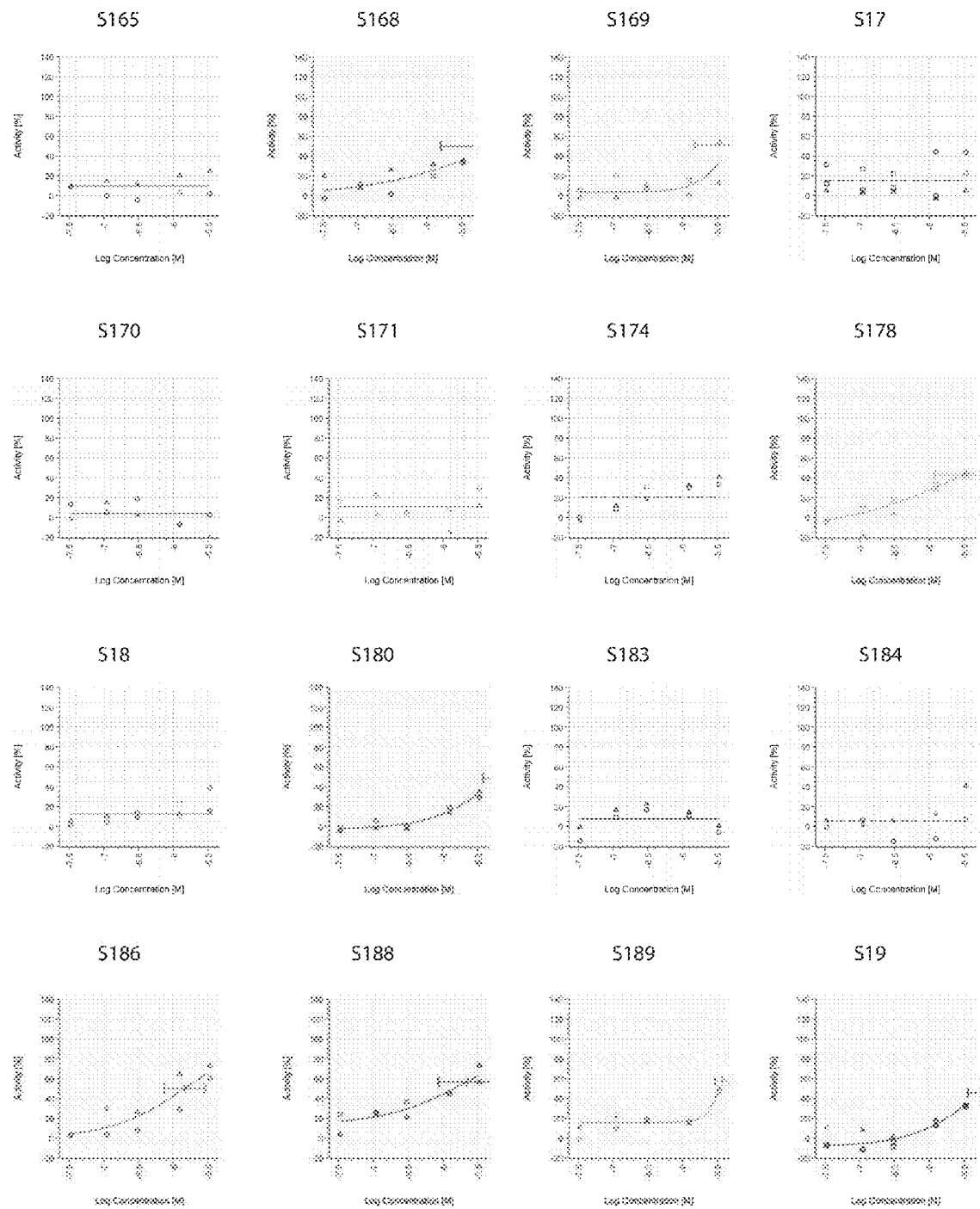
Figure 12:
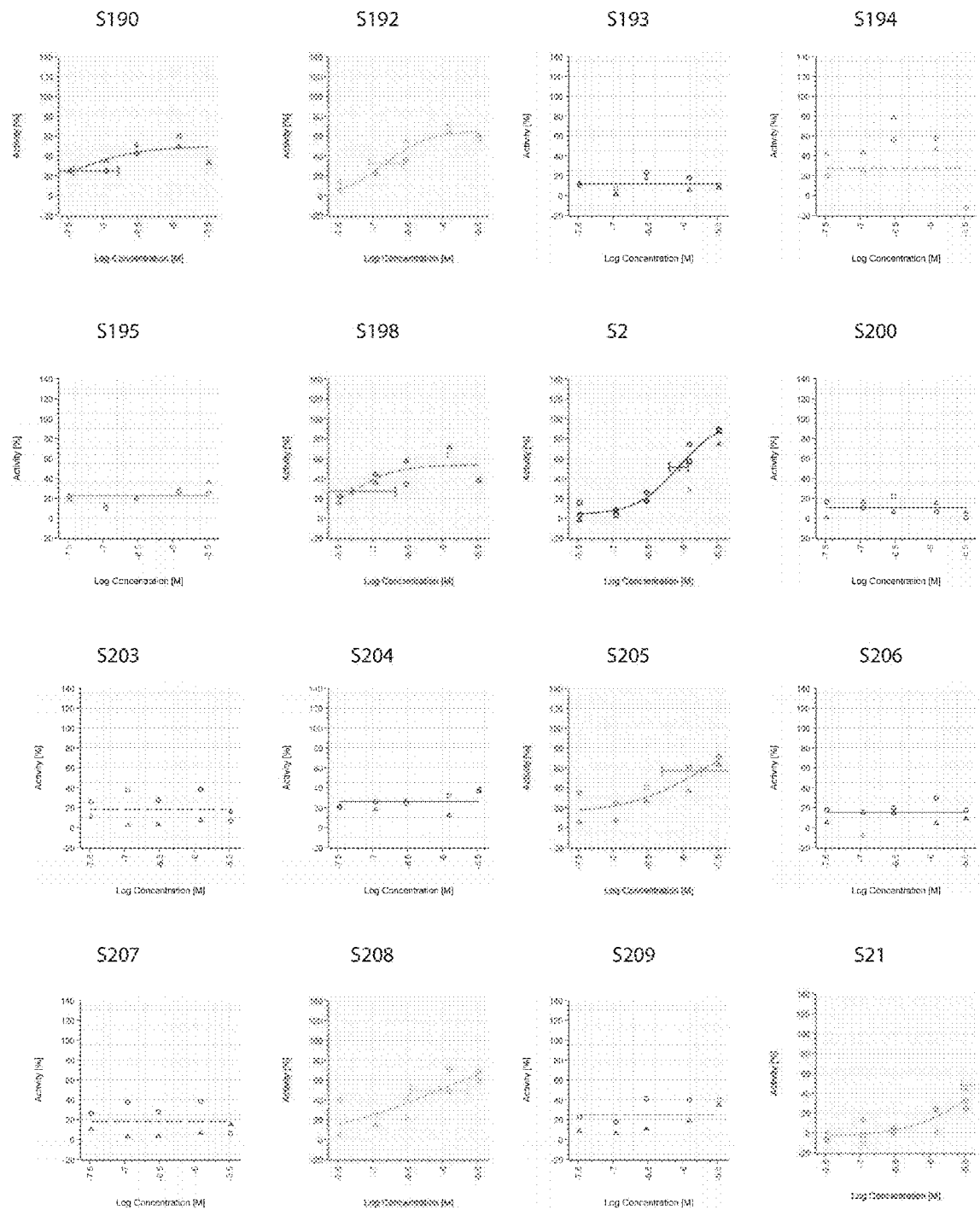
Figure 12:
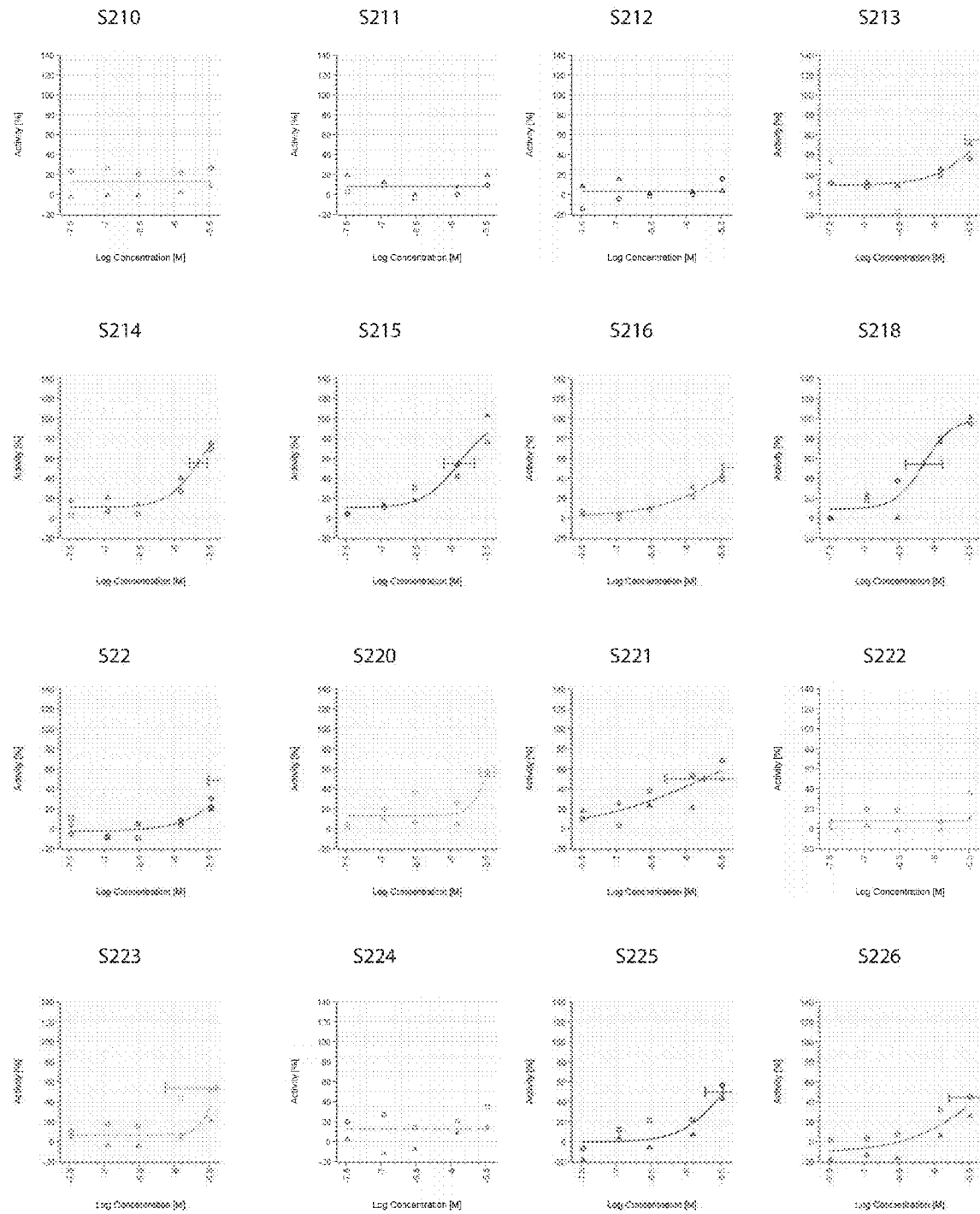
Figure 12:
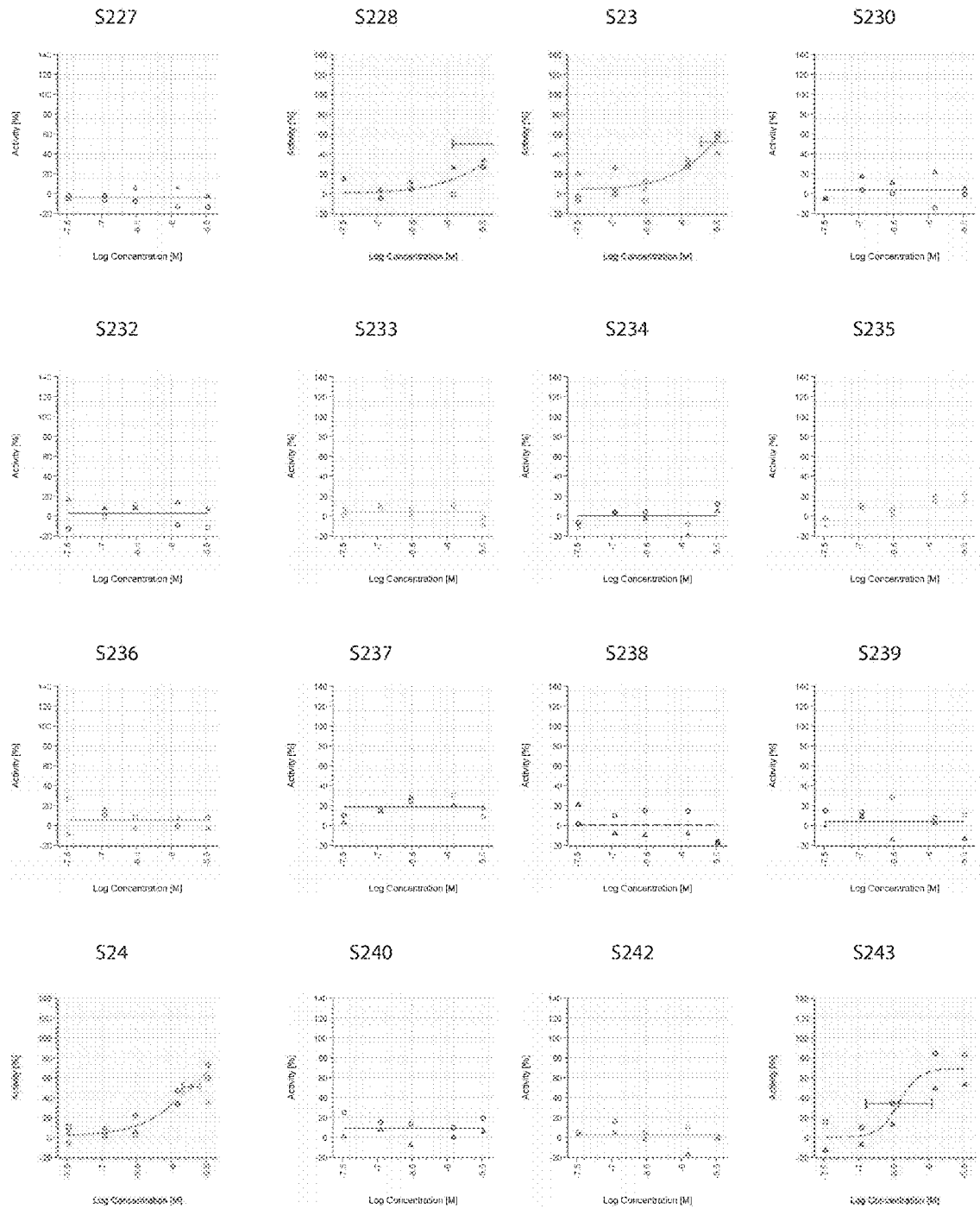
Figure 12:
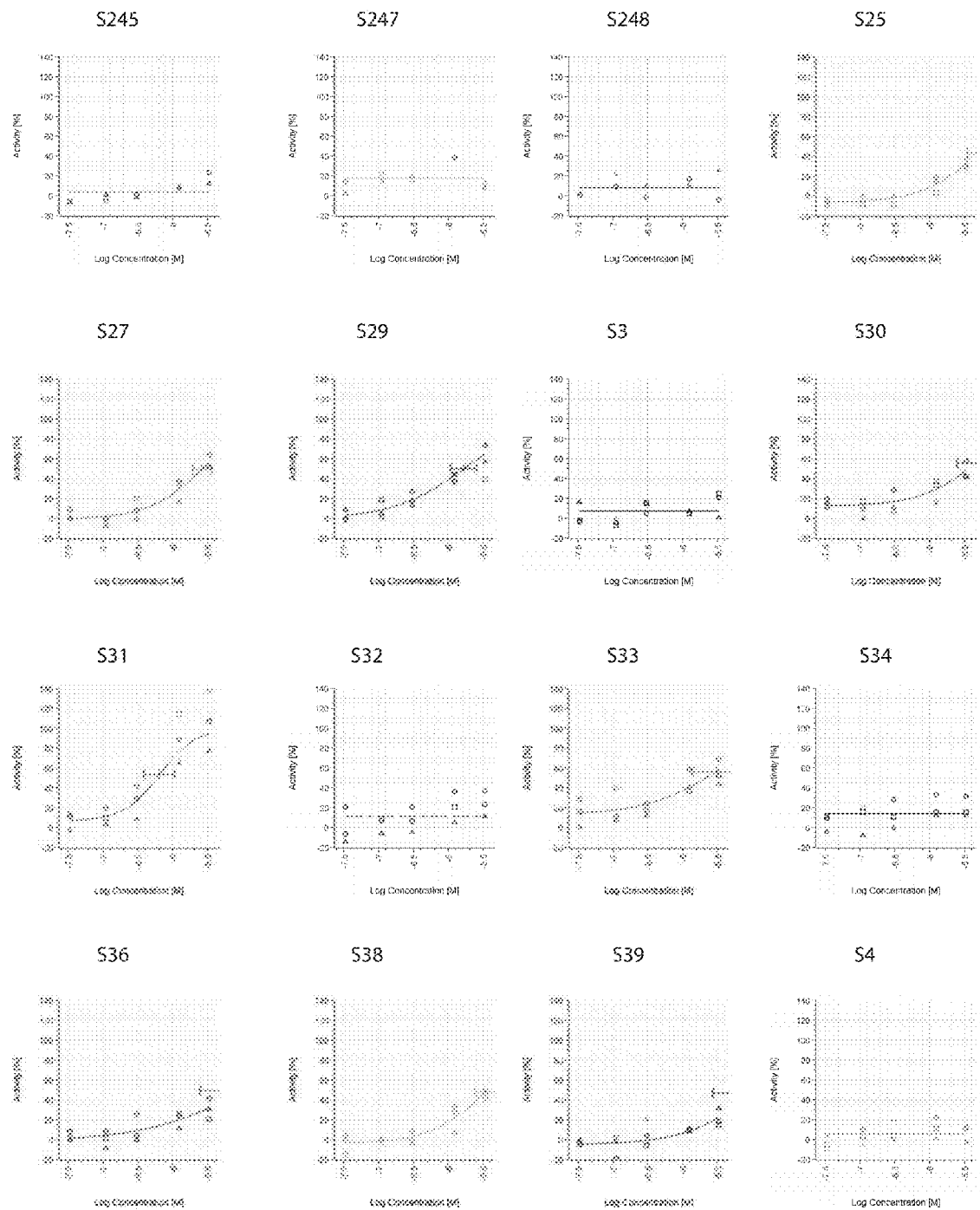
Figure 12:
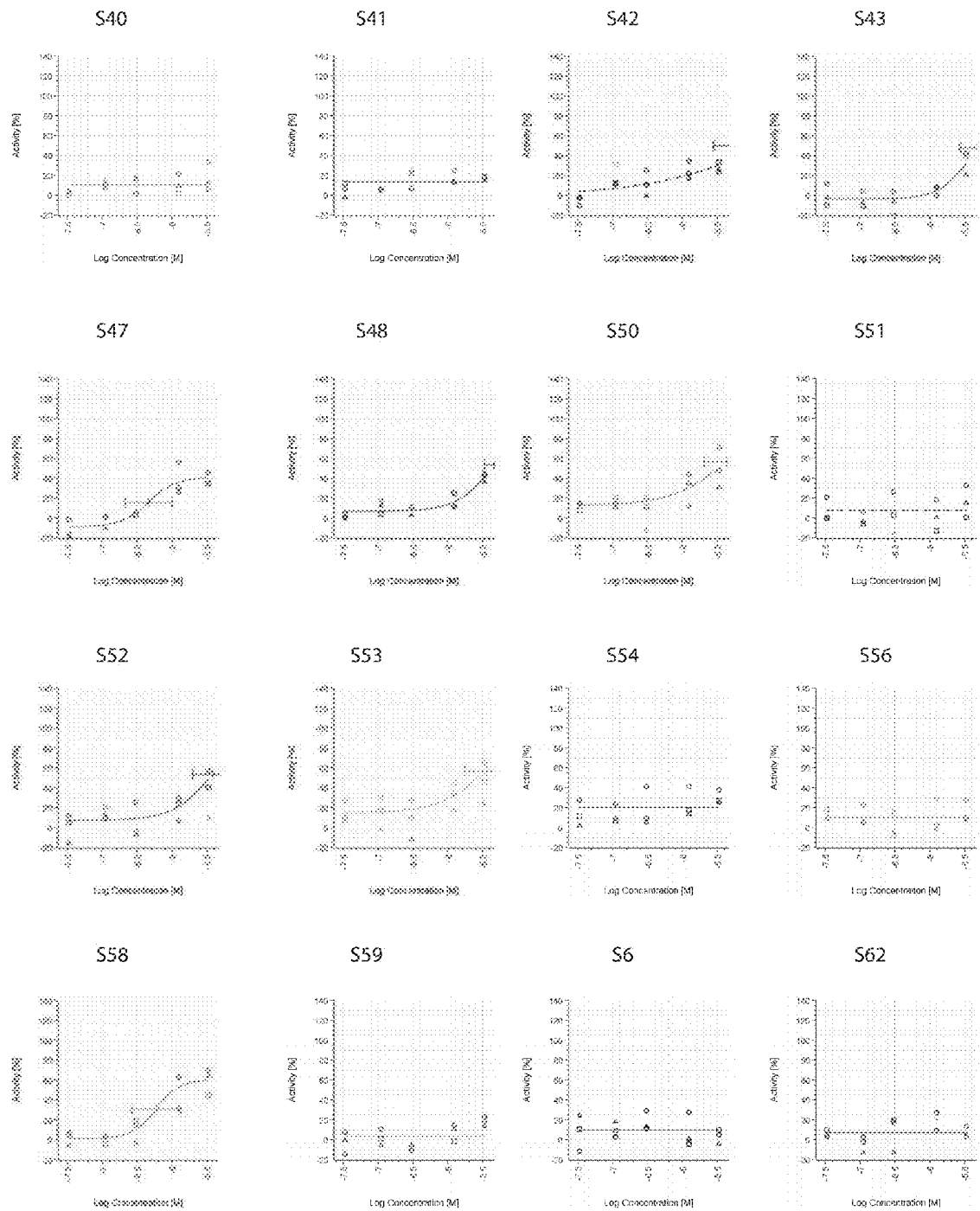
Figure 12:
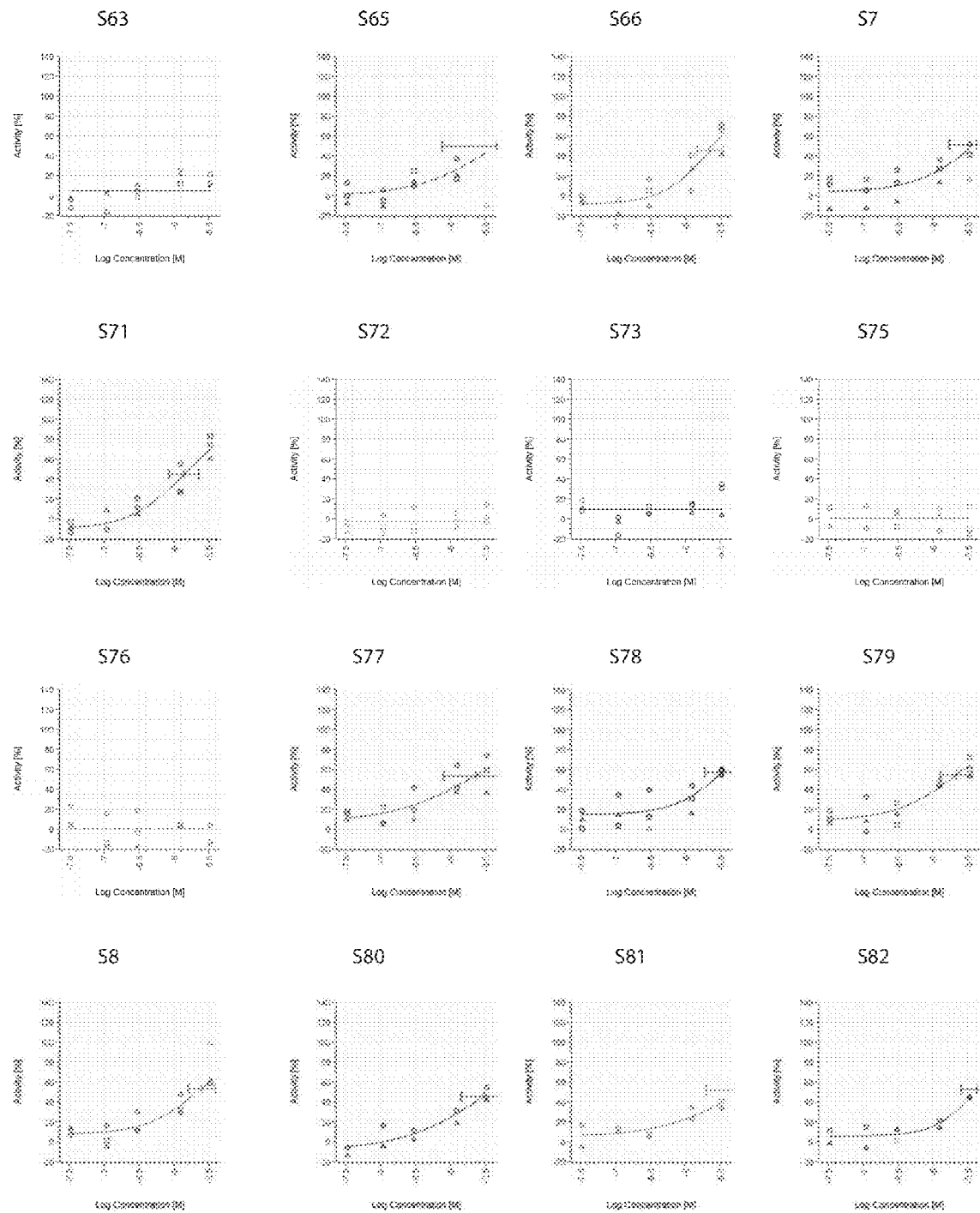
Figure 12:
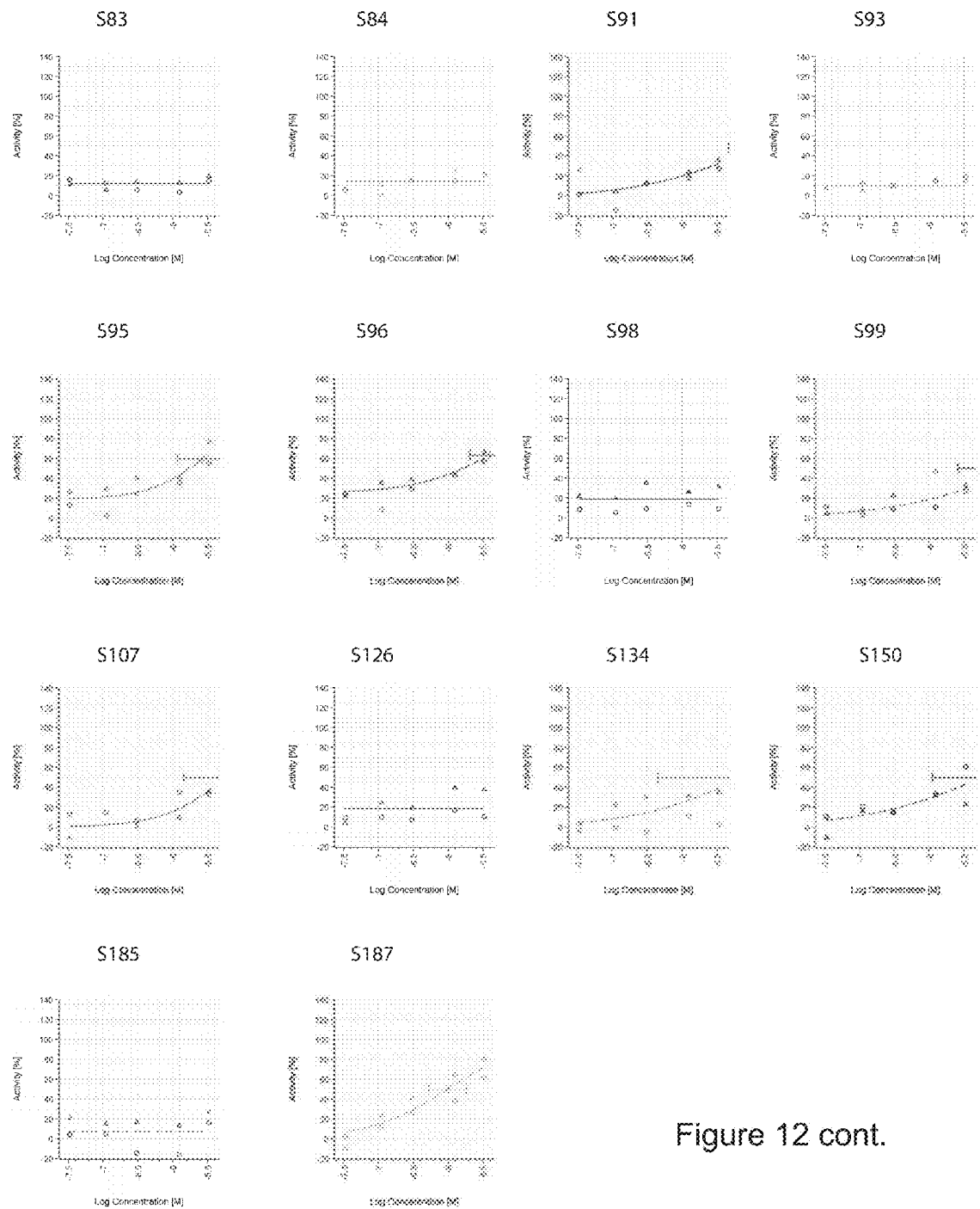

A more facile method of quantifying the NAD analyte, employing the commercially available "NAD/NADH-Glo" kit (Promega), confirmed P7C3-A20-mediated rebound of NAD levels in doxorubicin-treated U2OS cells. We also observed NAD rebound for the racemic mix of the active P7C3-S243 compound, but no rebound at all for the inactive P7C3-S6 and P7C3-S117 compound variants (FIG. 5B). This method of assay was used to test 159 variants of P7C3 that had been used to query the correlative relationship between dox:tox protection and competition in the P7C3-S326 crosslinking assay (Table 1 and FIG. 2D). Each chemical variant of P7C3 was co-incubated with doxorubicin on cultured U2OS cells at five doses (0.03 uM, 0.1 uM, 0.3 uM, 1 uM and 3 uM). After 45 hrs incubation, cells were assayed for intracellular levels of NAD (FIG. 12). The scatter plot shown in FIG. 5C reveals exceptional concordance between the dox:tox protective activities of the 159 compounds and their relative abilities to enhance NAD levels (correlative P value of $1.8 \times 10^{-35}$).

Figure 6:
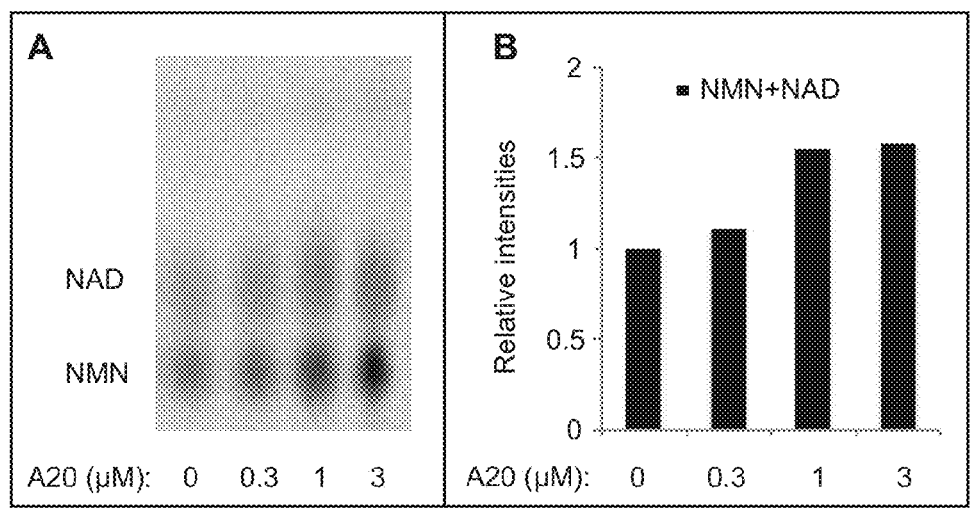
FIGS. 6A-6B. P7C3-A20 enhances the flux of nicotinamide through the salvage pathway.

NAMPT is the rate limiting enzyme in the salvage pathway whereby cells sequentially convert nicotinamide into nicotinamide adenine mononucleotide (NMN) and NAD (Preiss and Handler, 1958). If active variants of P7C3 indeed bind to the NAMPT dimer in a manner fostering its activity, then these compounds should enhance the flux of nicotinamide through the salvage pathway. To test this hypothesis, $^{14}$C-labeled nicotinamide was administered to cultured U2OS cells. Six hours later, cells were lysed in perchloric acid and cleared by centrifugation so that soluble materials could be separated by thin layer chromatography (TLC) followed by autoradiography. As shown in FIG. 6, enhanced conversion of radiolabeled nicotinamide into NMN and NAD was observed in a dose-responsive manner upon exposure of cultured U2OS cells to the active, A20 variant of P7C3.

Active Variants of P7C3 Enhance the Activity of the Purified NAMPT Enzyme

Figure 7:
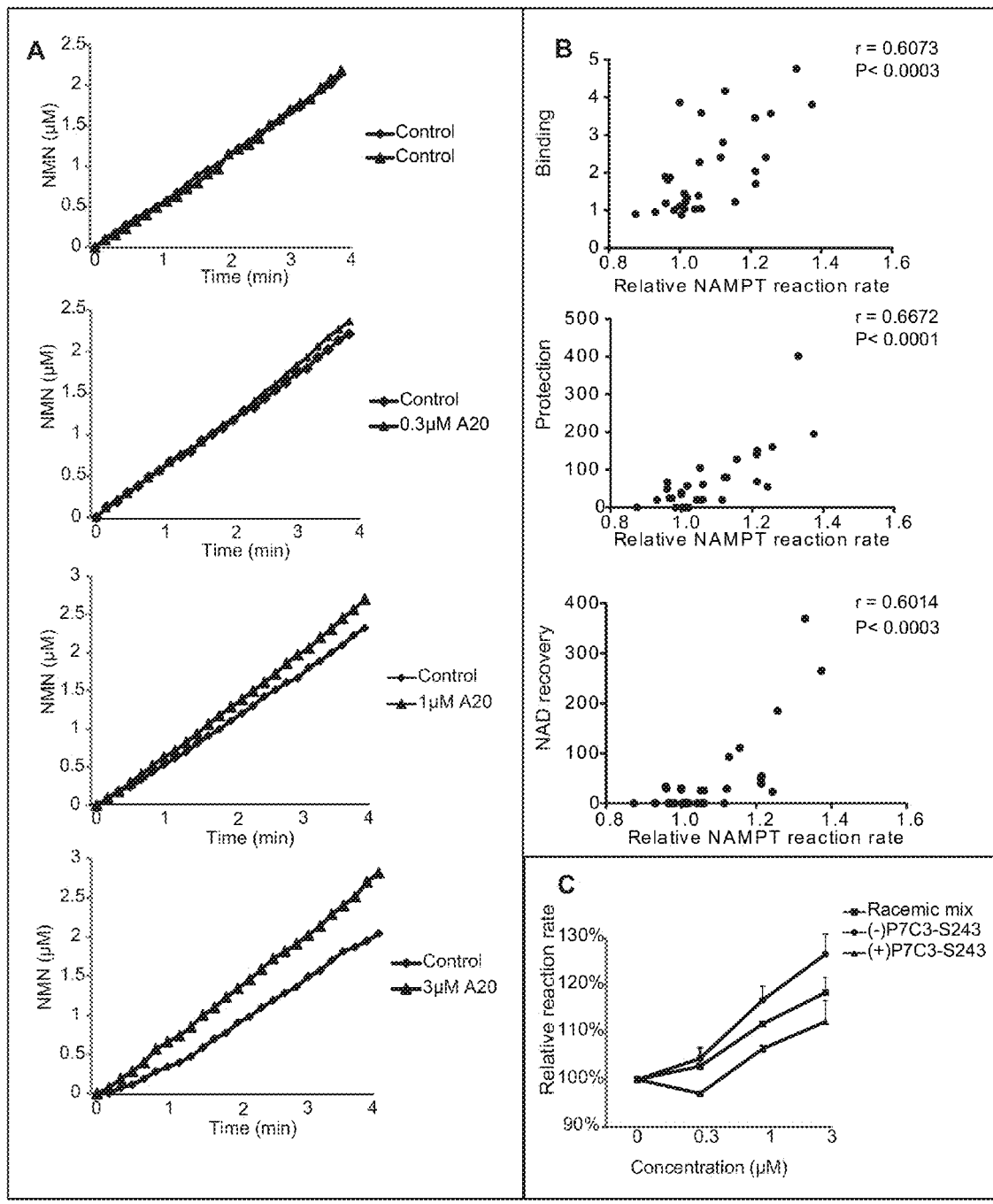
FIGS. 7A-7C. Active variants of P7C3 enhance the activity of purified NAMPT enzyme.

A recombinant form of the human NAMPT enzyme was cloned, expressed and purified according to published conditions (Khan et al., 2006) (Wang et al., 2006). The enzymatic activity of recombinant NAMPT was monitored in a coupled assay wherein nicotinamide conversion to NMN was followed by sequential production of NAD (via the NMNAT enzyme) and NADH (via alcohol dehydrogenase). To minimize variation, a control reaction was run in each assay prior to compound addition. As shown in FIG. 7A, the A20 variant of P7C3 activated the enzyme reaction in a dose dependent manner. No activation of NADH production was observed when NAMPT was eliminated from the reaction, giving evidence that enhancement did not result from compound effects on either NMNAT or alcohol dehydrogenase.

Two additional experiments were conducted to investigate activation of the recombinant NAMPT enzyme. First, thirty derivatives of P7C3 having varied activity were tested for enzyme activation. The ability of the thirty variants to activate NAMPT in the coupled enzyme assay was then correlated on scatter plots to three other measures of compound activity: (i) ability to protect cultured cells from doxorubicin toxicity; (ii) ability to compete with photo cross-linking by P7C3-S326 in living cells; and (iii) ability to restore NAD levels in doxorubicin treated cells (FIG. 7B). In all cases statistically significant evidence of correlation was observed. Second, we compared the activities of the racemic mix of P7C3-S243, the (−)P7C3-S243 enantiomer and the (+)P7C3-S243 enantiomer in NAMPT enzyme assay. As shown in FIG. 7C, the (−)P7C3-S243 enantiomer was more active in stimulating NAMPT than the racemix mix, which—in turn—was more active than the (+)P7C3-S243 enantiomer. This same hierarchy of activity has been observed in all in vivo assays tested to date, including adult neurogenesis, and the MPTP model of Parkinson's disease (Naidoo et al., 2014), concussive blast injury (accompanying manuscript), protection of cultured cells from doxorubicin-mediated activity (FIG. 1) and rebound of NAD levels in doxorubicin-treated cells (FIG. 11).

Discussion

Why is it that active variants of P7C3 were able to protect cultured cells from doxorubicin-mediated toxicity, in the face of no protective activity against seven other toxins? Three observations can now be seen to help understand this selectivity. First, doxorubicin reduces intracellular levels of NAD, likely via activation of poly-ADP ribose polymerase (PARP). Second, active variants of P7C3 protect cultured cells from dox:tox, likely by stimulating a rebound in the intracellular levels of NAD. Third, active variants of P7C3 enhance the activity of the purified, recombinant NAMPT enzyme. We conclude that the dox:tox protective activity of our aminopropyl carbazole chemicals is directly reflective of their ability to enhance the salvage pathway whereby nicotinamide is converted to NAD.

The target-agnostic in vivo screen performed years ago led, in an unbiased manner, to the P7C3 class of neuroprotective chemicals (Pieper et al., 2010). We now hypothesize that the neuroprotective efficacy of our aminopropyl carbazole chemicals can be attributed to their ability to foster salvage of NAD from nicotinamide. This interpretation is concordant with an equally unbiased series of forward genetic studies performed over the past three decades. In the 1980's scientists working in Oxford, England described a variant strain of mice that impedes Wallerian degeneration, designated the Wallerian degeneration slow (wlds) strain (Lunn et al., 1989). In simple terms, Wallerian degeneration can be described as the demise of axonal processes distal from the cell body to a site of nerve crush. Axons of wlds mice survive a nerve crush far longer than those of wild type mice. The wlds gene was positionally cloned in the 1990's and found to exist as a triplicated fusion gene encoding the first 70 amino acids of Ufd2a, a ubiquitin-chain assembly factor, linked directly to the complete coding sequence of nicotinamide mononucleotide adenylyl-transferase 1 (NMNAT1) (Coleman et al., 1998) (Conforti et al., 2000) (Mack et al., 2001). Whereas NAMPT initiates salvage from nicotinamide, NMNAT1 is one of three enzymes that convert the NMN product into NAD. In a beautiful paper published in 2004 in Science, Dr. Jeff Milbrandt and colleagues provided compelling evidence that the wlds phenotype can be attributed primarily to the over-expression of NMNAT1 (Araki et al., 2004). The closing sentence of their manuscript is unusually prescient, reading—"It is possible that the alteration of NAD levels by manipulation of the NAD biosynthetic pathway, Sir2 protein activity, or other downstream effectors will provide new therapeutic opportunities for the treatment of diseases involving axonopathy and neurodegeneration." We offer the conclusion that this is exactly what active variants of the P7C3 category of neuroprotective drugs do—they enhance the intracellular production of NAD by agonizing the activity of the rate limiting enzyme in the NAD salvage pathway.

It has recently been reported that NAD production attenuates as a function of aging in the hippocampus of rodents (Stein and Imai, 2014). This study further reported age-related decline in the expression of NAMPT in the hippocampus, along with evidence that selective elimination of the NAMPT gene in neuronal stem cells significantly impairs hippocampal neurogenesis. Now that we understand that active members of the P7C3 class of compounds function by enhancing the activity of the NAMPT enzyme, the observations of Stein and Imai lend credibility to our original discovery of P7C3 as a chemical stimulant of hippocampal neurogenesis.

In addition to offering progress towards an understanding of the mode of action of the P7C3 class of neuroprotective chemicals, this work also points to a number of important, unanswered questions. First and foremost, where on the NAMPT enzyme do our chemicals bind, and how do they facilitate agonistic activation? Second, why is it that covalent binding of S326 causes NAMPT to migrate in an anomalous manner in SDS PAGE gels? Third, is it indeed the case that NAD levels may be compromised as a function of nerve cell injury or neuronal dysfunction as a consequence of neurodegenerative disease? Fourth, might NAMPT be regulated in vivo by an endogenous metabolite that is either mimicked or counteracted by active variants of the P7C3 class of neuroprotective chemicals?

We close with two observations that may or may not be related. Studies of aged mice have led to the reported decline in tissue NAD levels, and that certain aspects of age-related decline in overall health can be reversed by nutritional supplementation of NMN (Gomes et al., 2013). In our initial studies of P7C3 we reported compound-mediated abrogation of cognitive decline in aged Fisher rats (Pieper et al., 2010). Included in such studies was the unanticipated observation that compound treated rats maintained body weight relative to the frailty of vehicle-treated controls. These distinct studies offer the possibility of considering the P7C3 class of neuroprotective chemicals as potential treatments for generalized frailty typical of aged animals and humans.

Experimental Procedures
Cell Culture

Osteosarcoma U2OS cells were grown in DMEM medium (Sigma) supplemented with 10% FBS. Lung cancer H2122 cells were cultured in RPMI-1640 medium (HyClone) supplemented with 5% FBS. These adherent cell lines were cultured employing standard procedures.

Cell Survival Assay

Cell survival assay was performed in 96-well plates using CellTiter-Glo Luminescent Cell Viability Assay kit (Promega) that measures cellular ATP content. The CellTiter-Glo reagent was diluted by adding 2 volumes of PBS containing 1% Triton X-100. 50 µl of diluted reagent was directly added to 100 µl of cell culture medium per well. Plates were incubated at room temperature for 10 minutes. Luminescence was recorded by Tecan SPECTRAFluor Plus reader (Tecan). Cell survival was presented as the percentage of viable cells compared with untreated control, and mean±SD was calculated from duplicates. The dox:tox assay of P7C3 analogs was carried out in the HTS Core (University of Texas Southwestern Medical Center) using the EnVison multimode plate reader (Perkin Elmer).

Chemical Synthesis of Photo-Crosslinking Probe P7C3-S326

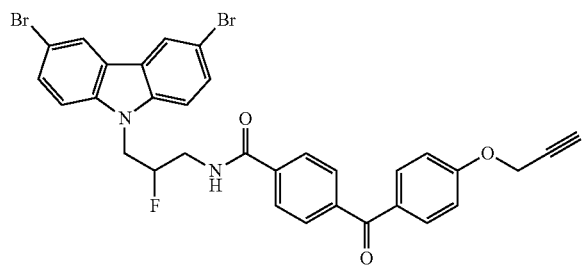 [SMILES: C#CCOc1ccc(C(=O)c2ccc(C(=O)NCC(F)Cn3c4ccc(Br)cc4c4cc(Br)ccc43)cc2)cc1]

N-(3-(3,6-dibromo-9H-carbazol-9-yl)-2-fluoropropyl)-4-(4-(prop-2-yn-1-yloxy)benzoyl)benzamide (P7C3-S326)

3-(3,6-dibromo-9H-carbazol-9-yl)-2-fluoropropan-1-amine (Naidoo et al., 2014) (40.2 mg, 0.10 mmol) was added to a solution of 4-(4-(prop-2-yn-1-yloxy)benzoyl)benzoic acid (Bandyopadhyay et al., 2011) (28.5 mg, 0.10 mmol), N-(3-dimethylaminopropyl)-N'-ethylcarbodiimide hydrochloride (21.2 mg, 0.11 mmol) and 1-hydroxybenzotriazole hydrate (15.0 mg, 0.11 mmol) in dimethylformamide (0.4 ml). The reaction went to completion within an hour. The mixture was diluted with EtOAc and washed several times with water and then brine. The organic layer was dried over $Na_2SO_4$, filtered and condensed to give a light brown solid in 90% yield. $^1$H NMR (Acetone-d6, 400 MHz) δ 8.41 (dd, J=2.0, 0.6 Hz, 2H), 8.07 (d, J=8.4 Hz, 2H), 7.82 (dd, J=10.3, 8.6 Hz, 4H), 7.71-7.56 (m, 4H), 7.16 (d, J=8.9 Hz, 2H), 5.39-5.10 (dm, 1H), 4.94 (d, J=2.4 Hz, 2H), 4.91-4.85 (m, 1H), 4.82 (d, J=5.4 Hz, 1H), 4.05-3.89 (m, 1H), 3.87-3.70 (m, 1H), 3.17 (t, J=2.4 Hz, 1H). $^{13}$C NMR ($CD_2Cl_2$, 100 MHz): 194.6, 167.3, 161.7, 141.4, 140.1, 136.9, 132.8, 130.7, 130.2, 129.7, 127.3, 124.1, 123.6, 114.9, 113.0, 111.2 ($J_{C-F}$=1.9 Hz), 92.1 ($J_{C-F}$=176.2 Hz), 78.2, 76.3, 56.4, 45.8 ($J_{C-F}$=22.5 Hz), 42.3 ($J_{C-F}$=21.2 Hz). MS (ESI), m/z: calculated 660.01. found 660.7 (M+1).

Live-Cell Crosslinking with Photo-Crosslinking Derivative P7C3-S326

P7C3-S326 was diluted to 0.3 µM in culture medium to treat H2122 cells. After incubation at 37° C. for 2 hours, H2122 cells were irradiated for 15 minutes under 306 nm ultraviolet light in a Stratalinker 2400 (Stratagene). Cells were then harvested by dissolving in 1% SDS lysis buffer 50 mM HEPES, pH 8.0, 2 mM MgCl2, 10 mM KCl, 1% SDS, 50 units/ml of Benzonase (Sigma), supplemented with Sigma-fast protease inhibitor (Sigma).

Attachment of Fluorescent Tags Via Copper-Catalyzed Azide-Alkyne Cycloaddition (CUAAC) CLICK Reaction For copper-catalyzed azide-alkyne cycloaddition CLICK reactions, 43 µl of SDS lysate were mixed with 3 µl of 1.7 mM Tris[(1-benzyl-1H-1,2,3-triazol-4-yl)methyl]amine (TBTA), 20 of 50 mM CuSO4, 1 µl of 50 mM Tris(2-carboxyethyl) phosphine (TCEP), and 1 µl of 1.25 mM Alexa 532-azide. The reaction was incubated at room temperature with constant agitation at 1,000 rpm on a thermomixer (Eppendorf) for 1 hour. Samples were then mixed with SDS sample loading buffer and loaded on an 8% SDS-PAGE gel, separated, and imaged using a Typhoon imager (filter settings: excitation 533 nm, emission 555 nm, and high sensitivity).

In Vivo Binding Competition Assay

H2122 cells were incubated with the P7C3-S326 (0.3 µM) in the absence or presence of P7C3 analogs for 2 hours following by UV crosslinking. Cells were lysed in 1% SDS lysis buffer and lysates were conjugated to the fluorescent Alexa 532 dye using CLICK reaction. The samples were run on SDS-PAGE gels scanned using a Typhoon Imager. The p70 band intensity was analyzed and quantified by Image J, and the relative intensity in each assay was normalized to that of the DMSO control.

Two-Dimensional Gel Electrophoresis

H2122 cells were incubated with P7C3-S326 (0.3 µM) in the absence or presence of 5 µM of the active analog P7C3-A20 for 2 hours followed by UV crosslinking. Cells were dissolved in 1% SDS lysis buffer and protein concentration was quantified by the BCA assay. For CLICK reactions, 1 mg of lysate prepared from P7C3-S326 treated cells were reacted with Alexa 532-azide (Red), and 1 mg of lysate from P7C3-S326 and P7C3-A20 treated cells were reacted with Cy5-azide (Green). After the CLICK reaction, the two lysates were combined, mixed with 4 volumes of acetone, incubated at −20° C. overnight. Precipitated proteins were collected by centrifugation at 8,000 g, 15 min, 4° C. After two washes with acetone, the pellet was air-dried and resuspended in 500 µl of 2D rehydration buffer (8M urea, 2% CHAPS (wt/vol), 50 mM dithiothreitol (DTT), 2% of IPG buffer). For two-dimensional gel electrophoresis, 500 µg of proteins was loaded onto immobilized pH gradient (IPG) strip of 24 cm pH 3-10 linear (GE Healthcare) by passive rehydration using rehydration chamber for overnight at room temperature. Isoelectric focusing was conducted on an IPG Phor3 manifold (GE healthcare) with the following protocol: 100V for 3 hours, 300V for 2 hours, 500V for 3 hours (Step-and-hold); 1000V for 1 hour (Gradient); 8000V for 3 hours (Gradient); 8000V for 4 hours (Step-and-hold) with total 42,000 V/hour. After isoelectric focusing, the strip was equilibrated for 15 minutes in equilibration buffer I (6M urea, 2% SDS (wt/vol), 0.375M Tris; pH 8.8, 20% glycerol (v/v), 100 mM DTT) for 15 minutes followed by equilibration buffer II (6M urea, 2% SDS (wt/vol), 0.375M Tris; pH 8.8, 20% glycerol (v/v), 250 mM iodoacetamide) for 15 minutes. Proteins were separated in the second dimension on 7.5% SDS-PAGE using Ettan Daltsix unit (GE Healthcare) at a constant current of 40 mA/gel for 5-6 hours at 100 W. Gel images were scanned at a resolution of 100 µm with on Typhoon FLA9500 scanner using default settings for CyDyes (GE Healthcare) and preprocessed using Image Quant TL software v8.1 (GE Healthcare). Cropped gel images were analyzed using DeCyder2D Differential Analysis Software v7.1 (GE Healthcare) to detect, normalize and quantify the protein features in the images. The P7C3-A20-competed green spots and several background spots were identified and robotically excised by an Ettan Spot Picker (GE Healthcare).

Mass Spectrometry for Protein Identification

Gel pieces were washed using 50 mM TEAB (triethylammonium bicarbonate, pH 8.0) in 50% (v/v) acetonitrile followed by reduction with 20 mM DTT and alkylation with 55 mM iodoacetamide, followed by dehydration using 100% (v/v) acetonitrile, air-dried, and then rehydrated in the presence of 250 ng of sequencing grade trypsin (Sigma) in 50 mM TEAB. Digests were allowed to proceed overnight at 37° C. Mass spectrometry was performed using Q Exactive mass-spectrometers (Thermo Fischer, Bremen), coupled to identical Ultimate 3000 RSLCnano HPLC systems (Dionex, Sunnyvale Calif.). Peptides were loaded onto a 75 µm i.d.×50 cm Thermo Scientific Easy-Spray column packed with 2 µm resin. A 40 minute linear gradient of 1%-28% acetonitrile in 0.1% formic acid followed by a 10 minute ramp to 98% ACN, using a flow rate of at 350 nl/min, was employed to elute peptides from the column. The Easy-Spray column was heated to 55° C. using the integrated heater. HCD analyses were performed on the Q Exactive instrument using a data-dependent top 20 method, with the full-MS scans acquired at 70K resolution (at m/z 200) and MS/MS scans acquired at 17.5K resolution (at m/z 200). The under-fill ratio was set at 0.1%, with a 3 m/z isolation window and fixed first mass of 100 m/z for the MS/MS acquisitions. Charge exclusion was applied to exclude unassigned and charge 1 species, and dynamic exclusion was used with duration of 15 seconds.

Measurement of Intracellular NAD Abundance

By LC-MS:

Cellular metabolites were extracted using 50% methanol by multiple freeze-thaw cycles. The cleared metabolites were dried in a Speed-Vac. The dried materials were dissolved in 0.1% formic acid and subjected to mass spectrometric analysis using a specific method developed for NAD. Relative intracellular NAD levels (NAD ion counts divided by total ion counts) were used for inter-sample comparisons.

By NAD/NADH-Glo Assay Kit:

Assay was performed following the manufacturer's protocol. NAD/NADH-Glo reagent contains the NAD Cycling Enzyme that converts NAD+ to NADH. In the presence of NADH, the enzyme reductase reduces a proluciferin reductase substrate to form luciferin. Cells were grown in 96- or 384-well plates. 50 µl or 15 µl of NAD/NADH-Glo™ Detection Reagent were added to each well. The resulting luminescence signals were measured by Tecan plate reader or EnVison multimode plate reader (Perkin Elmer).

Nicotinamide Flux Analysis with $^{14}$C-Labeled Nicotinamide

Logarithmically growing cells cultured in 6-well plates were treated with doxorubicin (0.5 µM) for 48 hours. Afterwards, 1 µl of 0.5 µCi/ml $^{14}$C nicotinamide (specific activity: 50 mCi/mmol; American Radiolabeled Chemicals, Inc.) was added per well six hours later. Cells were washed with PBS and collected by trypsin digestion. Metabolites were extracted from cells with 50 µl of perchloric acid (0.5 M) by incubating on ice for 20 minutes. The extracts were then neutralized with 13.75 µl of KCl/KOH (0.5 M/2.0 M) and centrifuged at 2500×g for 10 min at 4° C. 10 µl of extracted metabolites were separated and identified using silicon thin-layer chromatography plates with 1M ammonium acetate: ethanol (3:7) as solvent. For autoradiography, chromatograms were exposed to storage Phospho screen for 3 days. Afterwards, the screen was scanned using the Typhoon scanner, and the $^{14}$C-labeled compounds were quantified using Image J.

In Vitro NAMPT Enzyme Assay

NAMPT activity was determined by a coupled-enzyme spectrometric assay as described by Khan et al. (Khan et al., 2006) with minor modifications. Briefly, NAMPT first converted nicotinamide to NMN, which was followed by sequential production of NAD via nicotinamide mononucleotide adenylyl-transferase (NMNAT). NAD was then reduced to NADH by alcohol dehydrogenase (Sigma) using alcohol as the substrate. The resulting NADH was monitored by OD340 nm. Human NAMPT and NMNAT were over-expressed in *E. coli* and purified as described (Wang et al., 2006) and (Zhou et al., 2002), respectively. The reaction mixture contained 50 mM Tris (pH8.0), 0.4 mM phosphoribosylpyrophosphate (PRPP, Sigma) 2.5 mM ATP, 12 mM $MgCl_2$, 1.5% (v/v) ethanol, 10 mM semicarbazide (Sigma), 0.02%(w/v) BSA, 2.4 ug/ml NMNAT, 0.4 unit alcohol dehydrogenase, 1 uM NAMPT, and 150 uM nicotinamide. 10 mM stocks of P7C3 analogs in DMSO were further diluted in ethanol prior to applying to the reaction. To minimize variation, a control reaction was run in each assay prior to compound addition.

Statistics

Correlation data analysis was performed in GraphPad Prism 6. All p values were obtained using Spearman Rank Correlation (v1.0.1) in Free Statistics Software (v1.1.23-r7), Office for Research Development and Education, URL www.wessa.net/rwasp_spearman.wasp/.

REFERENCES

Araki, T., Sasaki, Y., and Milbrandt, J. (2004). Increased nuclear NAD biosynthesis and SIRT1 activation prevent axonal degeneration. Science 305, 1010-1013.

Bandyopadhyay, S., and Bong, D. (2011). Synthesis of trifunctional phosphatidylserine probes for identification of lipid-binding proteins. Eur. J. Org. Chem. 2011, 751-758.

Coleman, M. P., Conforti, L., Buckmaster, E. A., Tarlton, A., Ewing, R. M., Brown, M. C., Lyon, M. F., and Perry, V. H. (1998). An 85-kb tandem triplication in the slow Wallerian degeneration (Wlds) mouse. Proceedings of the National Academy of Sciences of the United States of America 95, 9985-9990.

Conforti, L., Tarlton, A., Mack, T. G., Mi, W., Buckmaster, E. A., Wagner, D., Perry, V. H., and Coleman, M. P. (2000). A Ufd2/D4Cole1e chimeric protein and overexpression of Rbp7 in the slow Wallerian degeneration (WldS) mouse. Proceedings of the National Academy of Sciences of the United States of America 97, 11377-11382.

De Jesus-Cortes, H., Xu, P., Drawbridge, J., Estill, S. J., Huntington, P., Tran, S., Britt, J., Tesla, R., Morlock, L., Naidoo, J., et al. (2012). Neuroprotective efficacy of aminopropyl carbazoles in a mouse model of Parkinson disease. Proceedings of the National Academy of Sciences of the United States of America 109, 17010-17015.

Gomes, A. P., Price, N. L., Ling, A. J., Moslehi, J. J., Montgomery, M. K., Rajman, L., White, J. P., Teodoro, J. S., Wrann, C. D., Hubbard, B. P., et al. (2013). Declining NAD(+) induces a pseudohypoxic state disrupting nuclear-mitochondrial communication during aging. Cell 155, 1624-1638.

Kempermann, G., Kuhn, H. G., and Gage, F. H. (1997). More hippocampal neurons in adult mice living in an enriched environment. Nature 386, 493-495.

Khan, J. A., Tao, X., and Tong, L. (2006). Molecular basis for the inhibition of human NMPRTase, a novel target for anticancer agents. Nat Struct Mol Biol 13, 582-588.

Kim, S. E., Ko, I. G., Kim, B. K., Shin, M. S., Cho, S., Kim, C. J., Kim, S. H., Baek, S. S., Lee, E. K., and Jee, Y. S. (2010). Treadmill exercise prevents aging-induced failure of memory through an increase in neurogenesis and suppression of apoptosis in rat hippocampus. Exp Gerontol 45, 357-365.

Kim, W. R., Park, O. H., Choi, S., Choi, S. Y., Park, S. K., Lee, K. J., Rhyu, I. J., Kim, H., Lee, Y. K., Kim, H. T., et al. (2009). The maintenance of specific aspects of neuronal function and behavior is dependent on programmed cell death of adult-generated neurons in the dentate gyrus. Eur J Neurosci 29, 1408-1421.

Kolb, H. C., Finn, M. G., and Sharpless, K. B. (2001). Click chemistry: Diverse chemical function from a few good reactions. Angewandte Chemie International Edition 40, 2004-2021.

Kuhn, H. G., Biebl, M., Wilhelm, D., Li, M., Friedlander, R. M., and Winkler, J. (2005). Increased generation of granule cells in adult Bcl-2-overexpressing mice: a role for cell death during continued hippocampal neurogenesis. Eur J Neurosci 22, 1907-1915.

Lunn, E. R., Perry, V. H., Brown, M. C., Rosen, H., and Gordon, S. (1989). Absence of Wallerian Degeneration does not Hinder Regeneration in Peripheral Nerve. Eur J Neurosci 1, 27-33.

Mack, T. G., Reiner, M., Beirowski, B., Mi, W., Emanuelli, M., Wagner, D., Thomson, D., Gillingwater, T., Court, F., Conforti, L., et al. (2001). Wallerian degeneration of injured axons and synapses is delayed by a Ube4b/Nmnat chimeric gene. Nat Neurosci 4, 1199-1206.

MacMillan, K. S., Naidoo, J., Liang, J., Melito, L., Morlock, L., Huntington, P. J., Estill, S. J., Longgood, J., Becker, G. L, et al. (2011). Development of proneurogenic, neuroprotective small molecules. J Am Chem Soc 133, 1428-1437.

Malberg, J. E., Eisch, A. J., Nestler, E. J., and Duman, R. S. (2000). Chronic antidepressant treatment increases neurogenesis in adult rat hippocampus. J Neurosci 20, 9104-9110.

Munoz-Gamez, J. A., Rodriguez-Vargas, J. M., Quiles-Perez, R., Aguilar-Quesada, R., Martin-Oliva, D., de Murcia, G., Menissier de Murcia, J., Almendros, A., Ruiz de Almodovar, M., and Oliver, F. J. (2009). PARP-1 is involved in autophagy induced by DNA damage. Autophagy 5, 61-74.

Naidoo, J., De Jesus-Cortes, H., Huntington, P., Estill, S., Morlock, L. K., Starwalt, R., Mangano, T. J., Williams, N. S., Pieper, A. A., and Ready, J. M. (2014). Discovery of a Neuroprotective Chemical, (S)—N-(3-(3,6-Dibromo-9H-carbazol-9-yl)-2-fluoropropyl)-6-methoxypyridin-2-amine [(−)-P7C3-S243], with Improved Druglike Properties. J Med Chem. 57, 3746-3754.

Pacher, P., Liaudet, L., Bai, P., Virag, L., Mabley, J. G., Hasko, G., and Szabo, C. (2002). Activation of poly(ADP-ribose) polymerase contributes to development of doxorubicin-induced heart failure. J Pharmacol Exp Ther 300, 862-867.

Pieper, A. A., McKnight, S. L., and Ready, J. M. (2014). P7C3 and an unbiased approach to drug discovery for neurodegenerative diseases. Chem Soc Rev. (in press).

Pieper, A. A., Xie, S., Capota, E., Estill, S. J., Zhong, J., Long, J. M., Becker, G. L., Huntington, P., Goldman, S. E., Shen, C. H., et al. (2010). Discovery of a proneurogenic, neuroprotective chemical. Cell 142, 39-51.

Preiss, J., and Handler, P. (1958). Biosynthesis of diphosphopyridine nucleotide. I. Identification of intermediates. Journal of Biological Chemistry 233, 488-492.

Stein, L. R. and Imai, S.-I. (2014). Specific ablation of NAMPT in adult neural stem cells recapitulates their functional defects during aging. EMBO Journal 33, 937-1085.

Sun, W., Winseck, A., Vinsant, S., Park, O. H., Kim, H., and Oppenheim, R. W. (2004). Programmed cell death of adult-generated hippocampal neurons is mediated by the proapoptotic gene Bax. J Neurosci 24, 11205-11213.

Tesla, R., Wolf, H. P., Xu, P., Drawbridge, J., Estill, S. J., Huntington, P., McDaniel, L., Knobbe, W., Burket, A., Tran, S., et al. (2012). Neuroprotective efficacy of aminopropyl carbazoles in a mouse model of amyotrophic lateral sclerosis. Proceedings of the National Academy of Sciences of the United States of America 109, 17016-17021.

Tu, B. P., Mohler, R. E., Liu, J. C., Dombek, K. M., Young, E. T., Synovec, R. E., and McKnight, S. L. (2007). Cyclic changes in metabolic state during the life of a yeast cell. Proceedings of the National Academy of Sciences of the United States of America 104, 16886-16891.

van Praag, H., Kempermann, G., and Gage, F. H. (1999). Running increases cell proliferation and neurogenesis in the adult mouse dentate gyrus. Nat Neurosci 2, 266-270.

Wang, J., Alexander, P., Wu, L., Hammer, R., Cleaver, O., and McKnight, S. L. (2009). Dependence of mouse embryonic stem cells on threonine catabolism. Science 325, 435-439.

Wang, T., Zhang, X., Bheda, P., Revollo, J. R., Imai, S., and Wolberger, C. (2006). Structure of Nampt/PBEF/visfatin, a mammalian NAD+ biosynthetic enzyme. Nat Struct Mol Biol 13, 661-662.

Zhou, T., Kurnasov, O., Tomchick, D. R., Binns, D. D., Grishin, N. V., Marquez, V. E., Osterman, A. L., and Zhang, H. (2002). Structure of human nicotinamide/nicotinic acid mononucleotide adenylyltransferase. Basis for the dual substrate specificity and activation of the oncolytic agent tiazofurin. Journal of Biological Chemistry 277, 13148-13154.

TABLE 1
| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| vehicle | DMSO | 7.3 | 0.0 | 1.0 | 0.0 | 0.98 | |
| P7C3 | | 15.0 | 52.3 | 2.6 | 30.6 | | |
| S1 | | 10.8 | 52.2 | | | | |
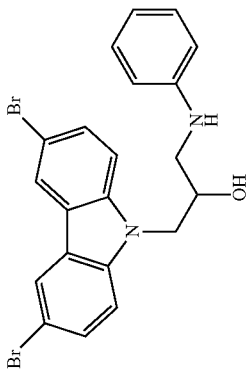

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S2 | (3,6-dimethylcarbazole-N-CH2-CH(OH)-CH2-NH-(3-methoxyphenyl)) | 8.1 | 232.0 | 3.7 | 109.3 | | |
| S3 | (3,6-dibromocarbazole-N-CH2-C(=O)-NH-(3-methoxyphenyl)) | 9.2 | 20.1 | 2.3 | 0.0 | 1.06 | |
| S4 | (3,6-dibromocarbazole-N-CH2-C(=O)-CH(SMe)-NH-(3-methoxyphenyl)) | 11.7 | 0.0 | 1.4 | 0.0 | 1.01 | |

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S5 | 12.2 | −27.8 | 1.4 | | | |
| S6 | 8.4 | 0.0 | 1.4 | 0.0 | | |
| S7 | 15.5 | 47.7 | 2.0 | 29.3 | | |
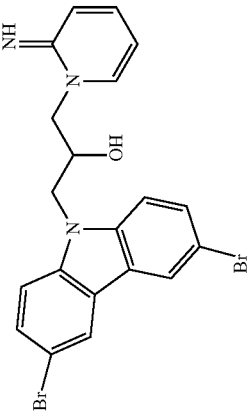
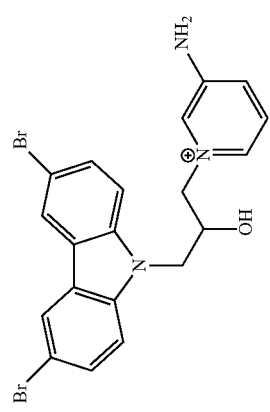
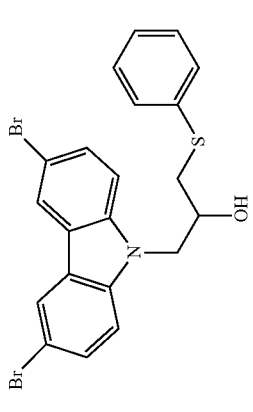

TABLE 1-continued

| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S8 | 7.8 | 141.0 | 4.7 | 37.4 | | |
| S9 | 11.9 | −20.1 | 2.0 | | | |
| S10 | 19.0 | 195.8 | 3.8 | 265.3 | 1.37 | A20 |

TABLE 1-continued

| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S11 | 12.8 | 68.8 | 2.0 | 39.4 | 1.21 | |
| S12 | 10.8 | 55.3 | 2.4 | 23.0 | 1.24 | |
| S13 | 11.6 | 151.5 | 1.7 | 54.8 | 1.21 | |

TABLE 1-continued
| compound # | | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|---|
| S14 | 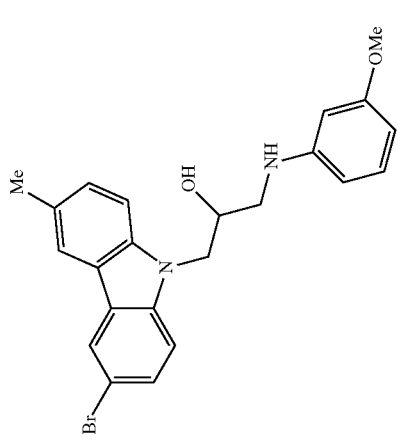 | 13.5 | 202.3 | 4.5 | 34.3 | | |
| S15 | 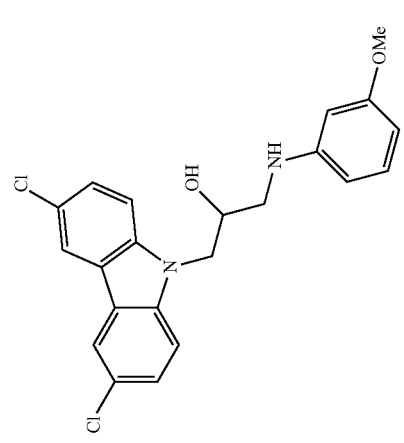 | 7.6 | 156.7 | 5.3 | 35.6 | | |

TABLE 1-continued

| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S16 | (structure: 3,6-dibromocarbazole-N-CH2-CH(OH)-CH2-NH-(3-methoxyphenyl)) | 9.2 | 191.9 | 3.1 | | | |
| S17 | (structure: 3,6-dibromocarbazole-N-CH2-CH(OH)-CH2-NH-(3-methoxyphenyl)) | 14.9 | 0.0 | 1.9 | 0.0 | | |

TABLE 1-continued
| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S18 | 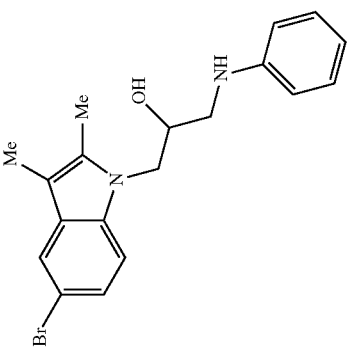 | 10.9 | 19.9 | 1.7 | 0.0 | | |
| S19 | 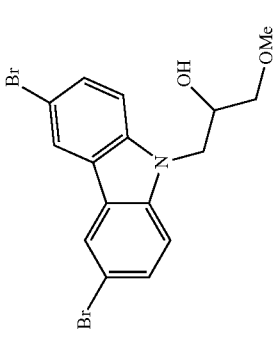 | 10.5 | 53.8 | 2.9 | 32.9 | | |
| S20 | 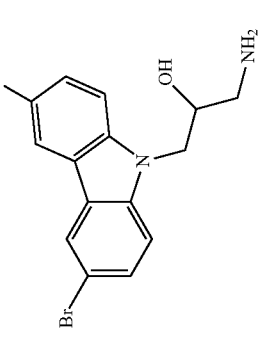 | 12.7 | −19.9 | 1.3 | | | |

TABLE 1-continued
| compound # | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|
| S21 | 8.8 | 20.4 | 2.3 | 31.6 | | |
| | 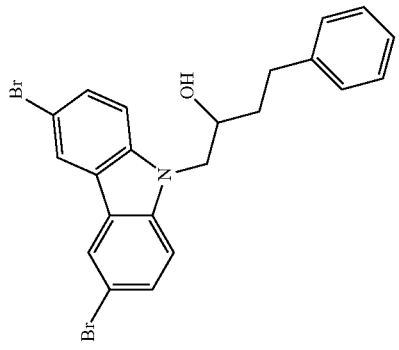 | | | | | |
| S22 | 6.7 | 0.0 | 2.7 | 31.0 | | |
| | 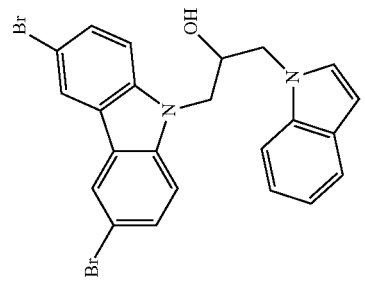 | | | | | |

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S23 | 7.4 | 138.5 | 2.1 | 30.9 | | |
| | 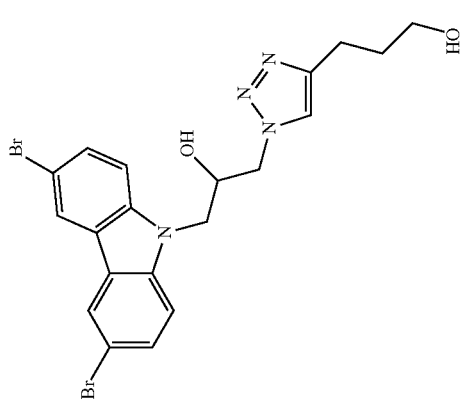 | | | | | |
| S24 | 8.0 | 44.8 | 3.1 | 51.5 | | |
| | 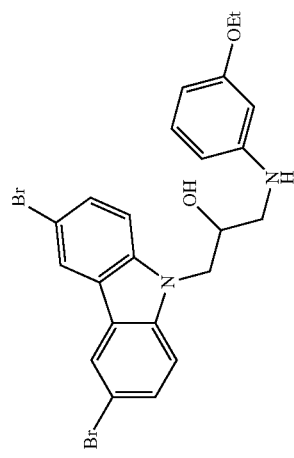 | | | | | |

TABLE 1-continued

| compound # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S25 | | 7.0 | 30.5 | 1.4 | 30.3 | | |
| S26 | | 7.5 | 0.0 | | | | A35 |
| S27 | | 8.1 | 109.9 | 2.8 | 38.4 | | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S28 | 3,6-dibromocarbazole-N-CH2-CH(OH)-CH2-SO2-phenyl | 13.6 | 31.3 | 2.8 | | | |
| S29 | 3-bromocarbazole-N-CH2-CH(OH)-CH2-NH-(3-methoxyphenyl) | 9.5 | 53.8 | 4.2 | 60.6 | | |
| S30 | 3,6-dibromo-α-carboline-N-CH2-CH(OH)-CH2-NH-phenyl | 14.3 | 22.2 | 3.3 | 26.6 | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S31 | 3,6-dibromocarbazole-CH2-CH(OH)-C(O)NH-(3-methoxyphenyl) | 10.4 | 464.0 | 6.2 | 145.1 | | |
| S32 | 3,6-dibromocarbazole-CH2-CH(OH)-CH2-CH2-NH-phenyl | 13.8 | 21.4 | 2.7 | 0.0 | | |
| S33 | 3,6-dibromocarbazole-(CH2)3-NH-phenyl | 11.6 | 80.2 | 2.8 | 28.7 | 1.12 | |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S34 | 7.6 | 0.0 | 1.0 | 0.0 | | |
| S35 | 8.6 | 0.0 | | | | |
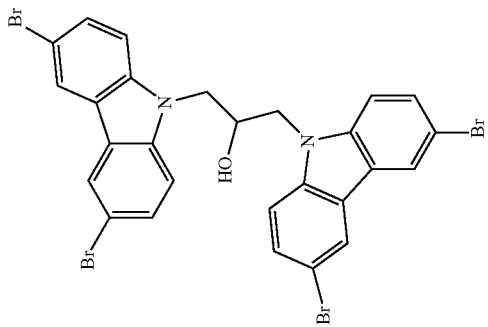
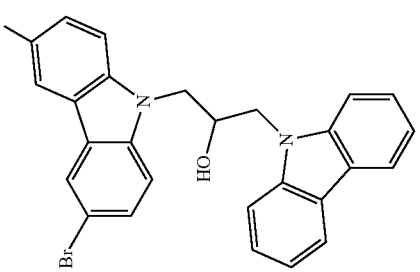

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S36 | 8.9 | 71.4 | 3.1 | 30.8 | | |
| S38 | 13.7 | 240.7 | 4.2 | 31.6 | | |
| S39 | 14.8 | 129.8 | 2.6 | 31.9 | | |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes | structure |
|---|---|---|---|---|---|---|---|
| S40 | 8.1 | 32.4 | 2.8 | 0.0 | | | 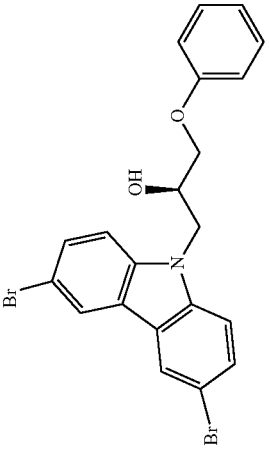 |
| S41 | 15.3 | 35.5 | 3.4 | | | | 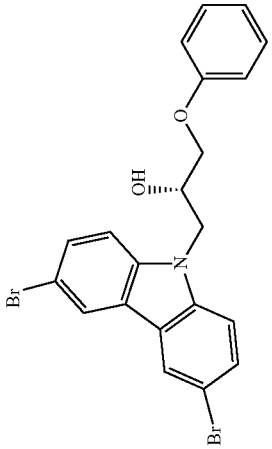 |
| S42 | 11.7 | 50.0 | 1.7 | 30.3 | | | 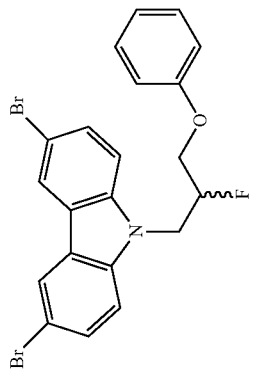 |

TABLE 1-continued
| compound # | Neurogenesis # BrdU+ Cells (X10E06)/mm3 Dentate Gyrus | Dox:tox protection Δ(Sinf-S0/AC50) | Binding competition | NAD recovery Δ(Sinf-S0/AC50) | NAMPT activation | notes |
|---|---|---|---|---|---|---|
| S43 | 11.7 | 98.3 | 1.7 | 31.5 | | |
| S45 | 8.0 | −24.3 | 1.2 | | | |
| S46 | 9.2 | −31.8 | 1.9 | | | |
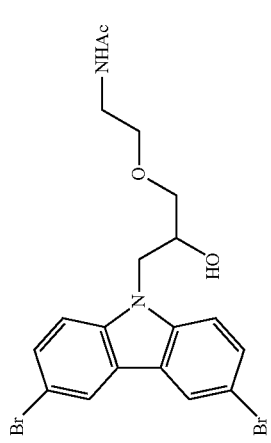
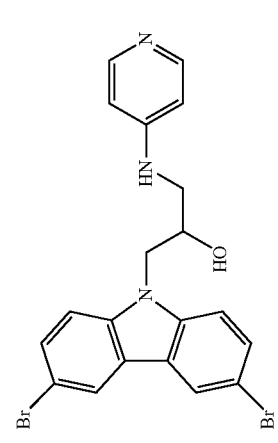
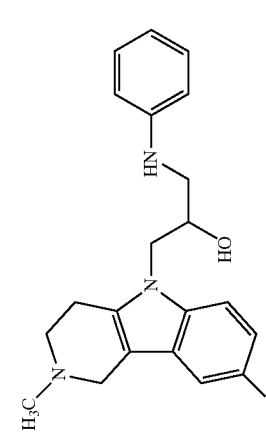

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S47 | | 10.1 | 56.2 | 5.5 | 109.2 | | |
| S48 | | 14.5 | 40.2 | 3.4 | 28.3 | | |
| S49 | | 12.0 | 171.0 | | | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S50 | 3,6-dibromocarbazole-N-CH2-CH(OH)(S)-CH2-SO2-Ph | 16.2 | 74.9 | 3.8 | 26.4 | | |
| S51 | 3,6-dibromocarbazole-N-CH2-CH(OH)(R)-CH2-SO2-Ph | 13.2 | 38.5 | 2.4 | 0.0 | | |
| S52 | 3,6-dichlorocarbazole-N-CH2-CH(OH)-CH2-SO2-Ph | 10.8 | 69.9 | 4.3 | 28.0 | | |
| S53 | 3,6-dibromocarbazole-N-CH2-CH(F)-CH2-SO2-Ph | 17.1 | 105.1 | 1.4 | 25.8 | 1.05 | |

TABLE 1-continued

| compound # | structure | Neurogenesis # BrdU+ Cells (X10E06)/mm3 Dentate Gyrus | Dox:tox protection Δ(Sinf-S0)/AC50 | Binding competition | NAD recovery Δ(Sinf-S0)/AC50 | NAMPT activation | notes |
|---|---|---|---|---|---|---|---|
| S54 | (3,6-dibromocarbazole with CH2-C(OH)(CH3)-CH2-NH-(3-methoxyphenyl)) | 16.7 | 1612.9 | 3.8 | 0.0 | | |
| S55 | (3,6-dibromocarbazole with CH2-CHF-CH2-NH-phenyl) | 13.8 | 92.4 | | | | |
| S56 | (3,6-dibromocarbazole with CH2-CF2-CH2-O-phenyl) | 8.4 | 21.4 | 1.0 | 0.0 | 1.06 | |

TABLE 1-continued

| compound # | structure | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|---|
| S57 | (3,6-dibromocarbazole-N-CH2-C(=N2)-CH2-O-C6H4-OMe) | 11.9 | 161.2 | | | | |
| S58 | (3-bromocarbazole-N-CH2-CH(OH)-CH2-NH-CH2-pyridyl) | 7.2 | 454.6 | 2.5 | 99.7 | | |
| S59 | (3,6-dibromocarbazole-N-CH2-C(F)(CF3?)-CH2-NH-C6H4-OMe) | 10.7 | 57.8 | 1.2 | 0.0 | 1.02 | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S60 | 3,6-dibromo-carbazole with N-CH2-CHF-CH2-NH-(4-methoxyphenyl) | 12.6 | | 1.4 | | | |
| S62 | 3,6-dicyclopropyl-carbazole with N-CH2-CH(OH)-CH2-NH-phenyl | 11.8 | 22.5 | 1.2 | 0.0 | | |
| S63 | 3,6-diiodo-carbazole with N-CH2-CH(OH)-CH2-NH-phenyl | 8.3 | 20.0 | 1.5 | 0.0 | | |

TABLE 1-continued

| compund # | | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|---|
| S64 | (carbazole with two terminal alkynes, N-substituted with CH2-CH(OH)-CH2-NH-(3-methoxyphenyl)) | 8.6 | 94.2 | | | | |
| S65 | (3,6-dicyano carbazole, N-substituted with CH2-CH(OH)-CH2-NH-(3-methoxyphenyl)) | 12.9 | 42.1 | 3.3 | 80.8 | | |
| S66 | (3,6-dibromo carbazole, N-substituted with CH2-CHF-CH2-NH-(4-(2-(2-methoxyethoxy)ethoxy)phenyl)) | 9.7 | 140.9 | 3.5 | 48.9 | 1.21 | |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S70 | 7.4 | 298.9 | 2.5 | | | |
| S71 | 7.2 | 122.8 | 3.1 | 80.0 | | |
| S72 | 11.7 | 0.0 | 1.4 | 0.0 | | |
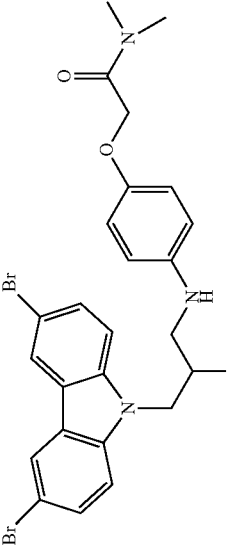
Molecular Weight: 577.28
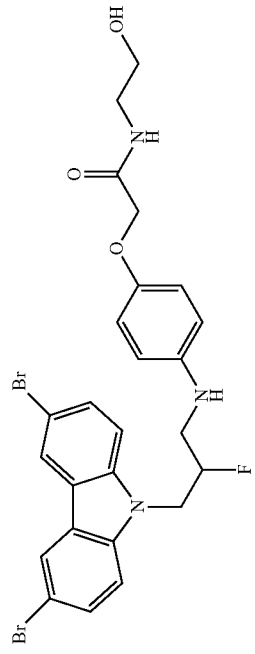
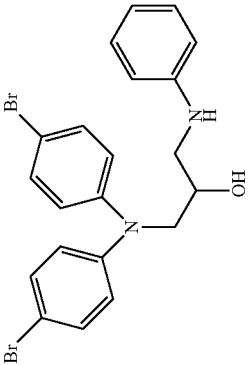

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S73 | 10.4 | 22.1 | 1.2 | 0.0 | | |
| S75 | 10.3/6.9 | 0.0 | 2.5 | 0.0 | | |
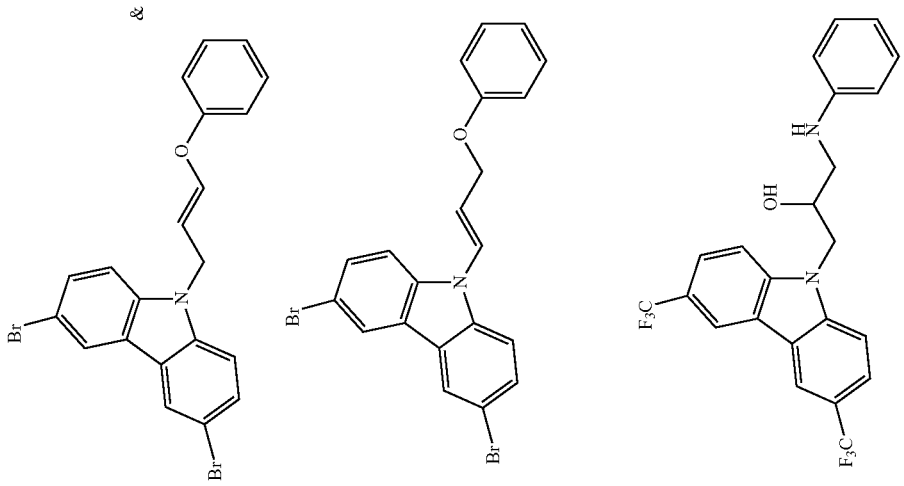

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S76 | 14.2 | 0.0 | 1.1 | 0.0 | | |
| S77 | 12.0 | 173.0 | 3.3 | 40.3 | | |
| S78 | 14.1 | 151.5 | 2.7 | 25.9 | | |
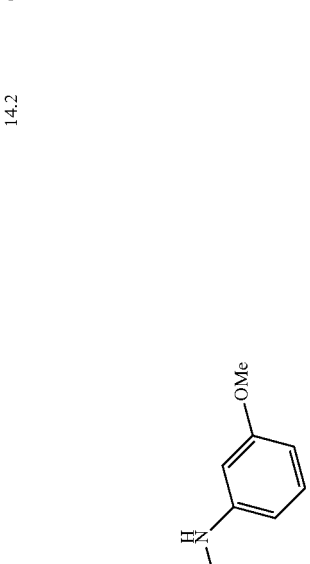

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S79 | 13.7 | 106.7 | 1.0 | 42.9 | | |
| | 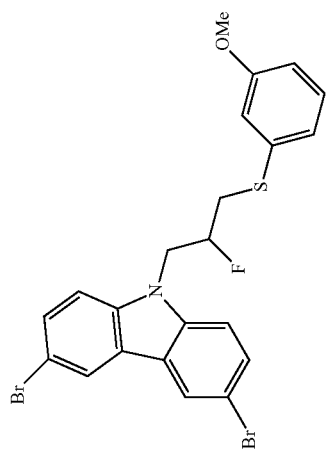 | | | | | |
| S80 | 13.0 | 97.4 | 0.9 | 35.9 | | |
| | 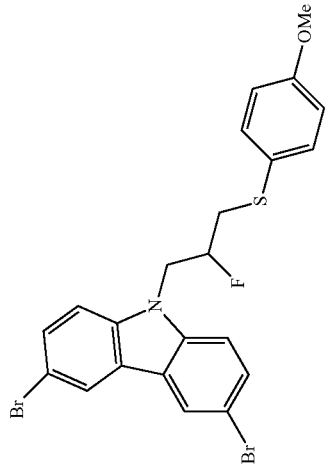 | | | | | |

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S81 | 12.6 | 66.8 | 1.2 | 28.9 | 0.96 | |
| S82 | 11.8 | 71.2 | 2.3 | 28.6 | | |

S81: 3,6-dibromo-carbazole N-substituted with CH2-CHF-CH2-SO2-(3-methoxyphenyl)

S82: 3,6-dibromo-carbazole N-substituted with CH2-CH(OH)-CH2-SO2-(3-methoxyphenyl)

TABLE 1-continued
| compound # | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|
| S83 | 12.5 | 0.0 | 1.0 | 0.0 | 1.01 | |
| S84 | 12.8 | 0.0 | 1.2 | 0.0 | | |
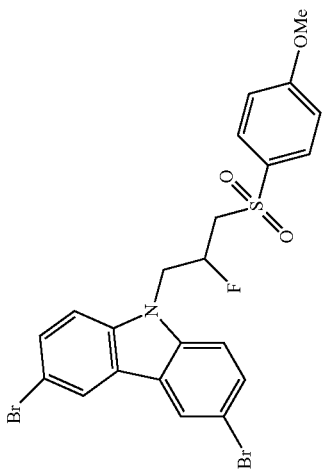
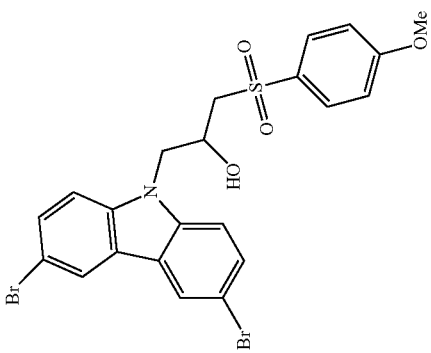

TABLE 1-continued
| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S85 | 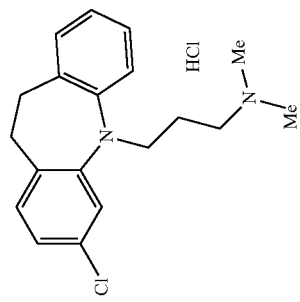 | 8.4/13.0 | −39.7 | 0.9 | | | Clomipramine (tricyclic antidepressant, SNRI and SSRI) |
| S86 | 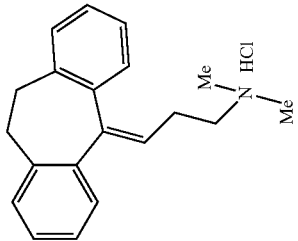 | 9.7 | −27.1 | 1.3 | | | Amitriptyline (serotonin, norepinephrine reuptake inhibitor) |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S87 | | 14.7 | −21.7 | 1.2 | | | Desipramine |
| S88 | | 7.8 | −24.3 | 1.1 | | | Imipramine |
| S89 | | 8.7 | −38.5 | 1.3 | | | Nortriptyline |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S90 | 11.1 | −39.2 | 1.4 | | | Protriptyline |
| S91 | 8.2 | 20.0 | 3.4 | 31.2 | | |
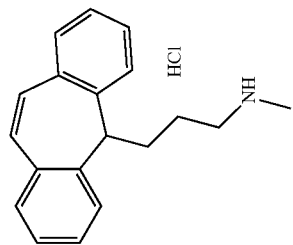
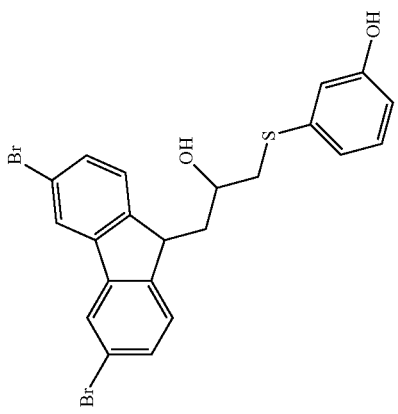

TABLE 1-continued

| compound # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S92 | | 8.4 | 20.0 | 2.5 | | | |
| S93 | | 11.9 | 0.0 | 1.4 | 0.0 | | |
| S94 | | 8.5 | 0.0 | 3.8 | | | |

TABLE 1-continued

| compound # | structure | Neurogenesis # BrdU+ Cells (X10E06)/mm3 Dentate Gyrus | Dox:tox protection A(Sinf-S0/AC50 | Binding competition | NAD recovery A(Sinf-S0/AC50 | NAMPT activation | notes |
|---|---|---|---|---|---|---|---|
| S95 | 3,6-dibromocarbazole-N-CH2-CH(OH)-CH2-S-(3-aminophenyl) | 8.6 | 71.2 | 4.6 | 30.2 | | |
| S96 | 3,6-dibromocarbazole-N-CH2-CH(OH)-CH2-S-(4-aminophenyl) | 8.7 | 55.6 | 3.9 | 22.7 | | |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S97 | 7.6 | −31.6 | 2.0 | | | |
| S98 | 6.9 | 0.0 | 1.1 | 0.0 | | |
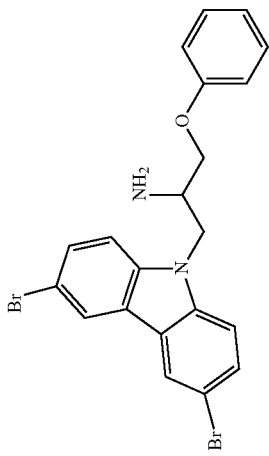
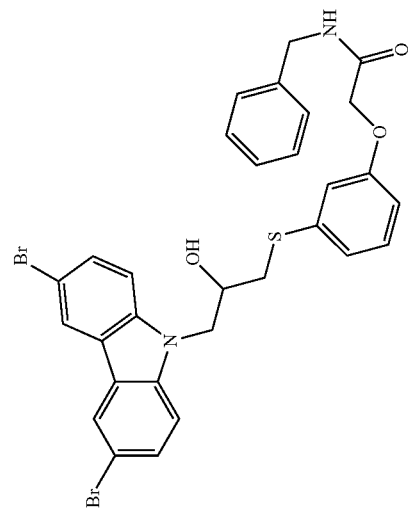

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S99 | 7.6 | 0.0 | 2.5 | 30.3 | | |
| S101 | 9.9 | 20.0 | 2.4 | 0.0 | 1.12 | |
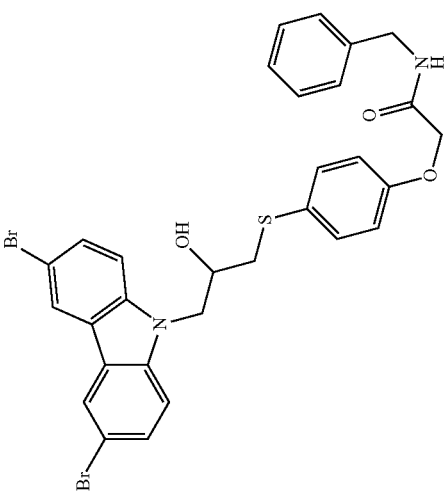
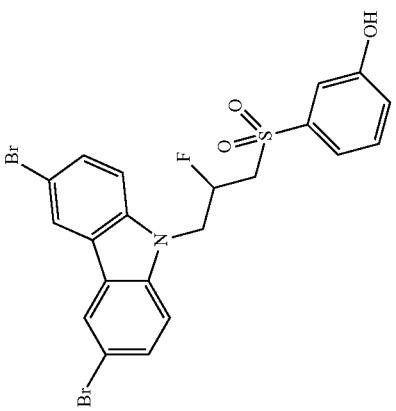

TABLE 1-continued
| compound # | Neurogenesis # BrdU+ Cells (X10E06)/mm3 Dentate Gyrus | Dox:tox protection Δ(Sinf-S0/AC50) | Binding competition | NAD recovery Δ(Sinf-S0/AC50) | NAMPT activation | notes |
|---|---|---|---|---|---|---|
| S102 | 8.9 | −35.3 | | | | |
| S103 | 7.0 | 24.1 | 1.9 | 0.0 | 0.97 | |
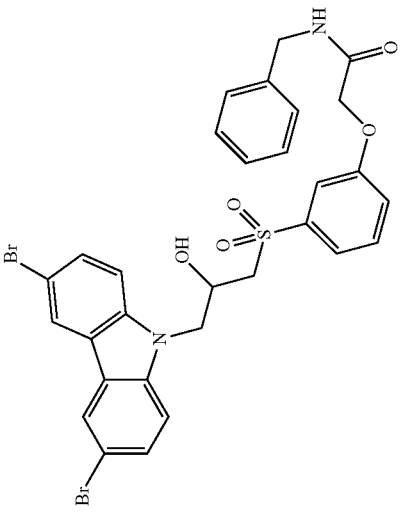
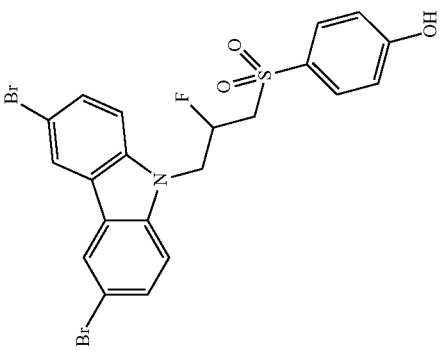

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S104 | 0.0 | | | | | |
| S105 | 10.8 | −32.9 | 1.2 | | | |
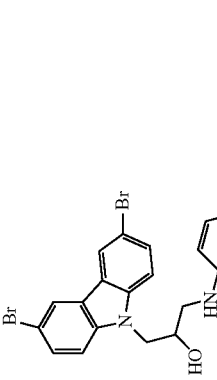
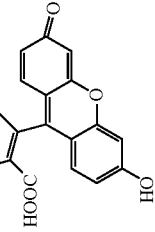

TABLE 1-continued
| compound # | Neurogenesis # BrdU+ Cells (X10E06)/mm3 Dentate Gyrus | Dox:tox protection Δ(Sinf-S0)/AC50 | Binding competition | NAD recovery Δ(Sinf-S0)/AC50 | NAMPT activation | notes |
|---|---|---|---|---|---|---|
| S106 | 10.9 | 0.0 | 1.4 | 0.0 | | |
| S107 | 7.3 | 160.8 | 3.5 | 30.3 | | |
| S108 | 7.6 | −77.6 | 1.0 | | | |
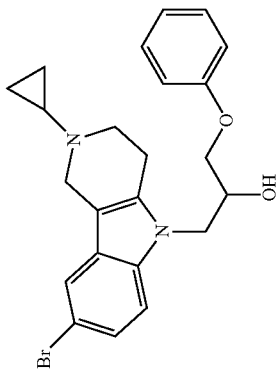
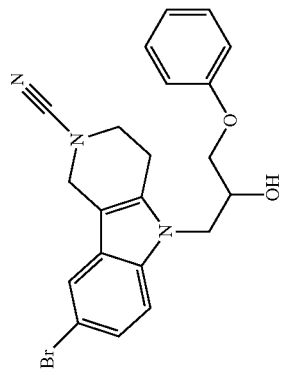
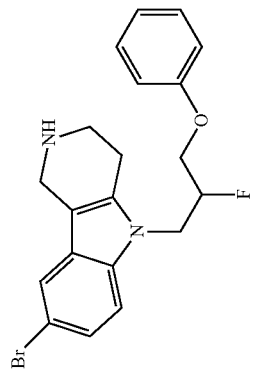

TABLE 1-continued
| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S109 | 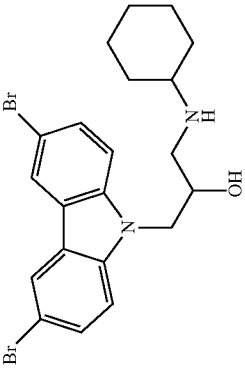 | 9.4 | −64.5 | 1.2 | | | |
| S110 | 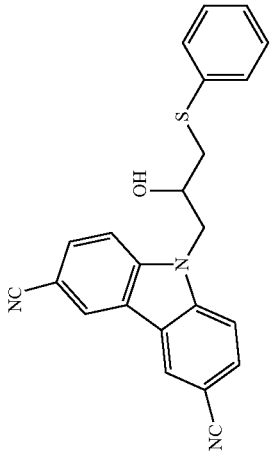 | 10.5 | 325.4 | 6.2 | 35.5 | | |
| S111 | 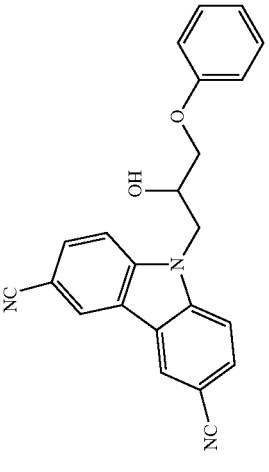 | 12.3 | | 4.1 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S112 | 3,6-dibromo-9H-carbazol-9-yl acetanilide | | | 1.2 | | | |
| S115 | 3,6-dibromo-9-(2-anilinoethyl)carbazole | 6.6/9.6 | 17.4 | 3.7 | 0.0 | | |
| S116 | phenethylhydrazine | 11.0 | 0.0 | 1.2 | 0.0 | | Nardi (MAOI) |
| S117 | N-methyl-N-propargyl-phenylisopropylamine | 8.1 | 0.0 | 1.0 | 0.0 | | Selegiline (MAOI) |
| S118 | trans-2-phenylcyclopropylamine | 8.3 | 0.0 | 1.3 | 0.0 | | Parnate (MAOI) |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S119 | | 8.6 | -18.6 | 1.2 | | | Celexa (SSRI) |
| S120 | | 10.4/8.8 | -38.1 | 1.3 | | | Paxil (SSRI) |
| S121 | | 11.1 | -32.9 | 2.3 | | | CPZ (dopamine antagonist) |
| S122 | | 10.0 | -28.0 | 1.4 | | | Prozac (SSRI) |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S123 | | 9.4 | −63.3 | 1.5 | | | Zoloft (SSRI) |
| S124 | | 8.9 | 0.0 | 1.1 | 0.0 | | Effexor (SNRI) |
| S125 | | | 0.0 | 1.1 | 0.0 | | Wellbutrin (NDRI) |
| S126 | | 8.8 | 0.0 | 1.3 | 0.0 | | Remeron (tetracyclic, SNRI and SSRI) |

TABLE 1-continued
| compound # | Neurogenesis # BrdU+ Cells (X10E06)/mm3 Dentate Gyrus | Dox:tox protection Δ(Sinf-S0/AC50) | Binding competition | NAD recovery Δ(Sinf-S0/AC50) | NAMPT activation | notes |
|---|---|---|---|---|---|---|
| S127 | 6.9 | −17.2 | 1.2 | | | Buspar (dopamine antagonist) |
| S128 | | −37.4 | | | | |
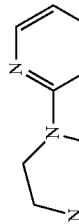
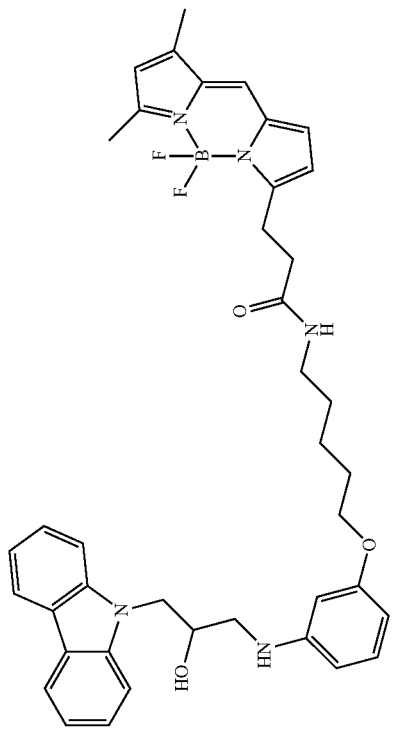

TABLE 1-continued

| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S129 | | 0.0 | | | | |
| S130 | | −34.0 | 2.9 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S131 | (tetrahydro-β-carboline with N-Me, Br, and OH/OPh side chain) | 7.3 | −34.4 | 3.5 | | | |
| S132 | (indole with dibenzazepine and OH linker) | 11.4 | 20.0 | 1.3 | 29.0 | | |
| S133 | (carbazole with dibenzazepine and OH linker) | 10.1 | 0.0 | 1.2 | 0.0 | | |

TABLE 1-continued
| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S134 | 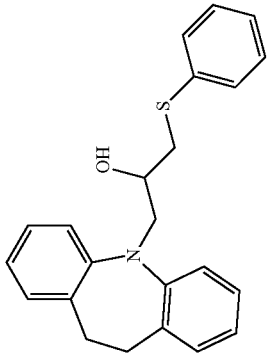 | 9.7 | 20.0 | 1.9 | 30.3 | | |
| S135 | 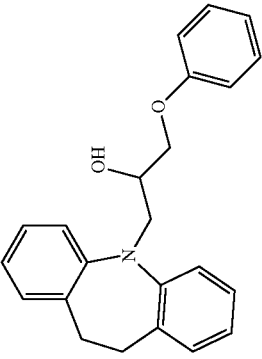 | 7.1 | 20.0 | 3.4 | 0.0 | | |
| S136 | 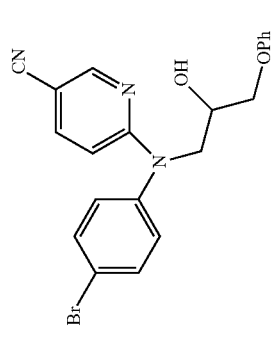 | 6.5 | 513.7 | 5.7 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S137 | (3,6-dibromocarbazole with N-CH2-CH(OH)-CH2-N(pyridin-2-one)) | 12.2 | 358.9 | 4.5 | 130.5 | | |
| S138 | (3-cyanocarbazole with N-CH2-CH(OH)-CH2-OPh) | 10.4 | 209.3 | 6.5 | 30.3 | | |
| S140 | (10,11-dihydrodibenzazepine with N-CH2-CH(OH)-CH2-NH2) | 11.7 | −18.6 | 1.2 | | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S141 | 3,6-dibromocarbazole-N-CH2-CH(OH)-CH2-SO2-C6H4-O-(CH2)5-NH-Boc | 11.3 | −17.8 | 2.7 | | | |
| S143 | dibenzazepine-N-CH2-CH(OH)-CH2-NH-CH3 | 7.3 | 0.0 | 1.3 | 0.0 | | |
| S144 | dibenzazepine-N-CH2-CH(OH)-CH2-NH-iPr | 9.1 | −41.0 | 1.4 | | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S145 | | 12.5 | −73.4 | 2.6 | | | |
| S146 | | 14.5 | 78.7 | 2.8 | | | |
| S147 | | 13.3 | 225.1 | 3.4 | 37.4 | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S148 | | 11.3 | −17.4 | 1.3 | | | tricyclic antidepressant (SNRI and SSRI) |
| S149 | | 11.6 | −17.9 | 1.2 | | | |
| S150 | | 8.4 | 45.8 | 4.1 | 30.3 | | |
| S152 | | 13.4 | −29.7 | 1.6 | | | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S153 | | 10.7 | 0.0 | 1.4 | 0.0 | | |
| S156 | | 15.0 | 0.0 | 1.2 | 0.0 | | |
| S157 | | 10.2 | −35.9 | 1.5 | | | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S158 | | 12.5 | 0.0 | 1.3 | 0.0 | | |
| S160 | | 13.1 | 20.0 | 4.3 | 0.0 | | |
| S161 | | 11.4 | 24.2 | 3.1 | 26.0 | | |

TABLE 1-continued
| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S162 | 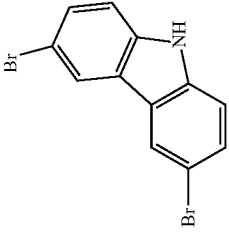 | 12.6/10.8 | 0.0 | 2.3 | 0.0 | | |
| S163 | 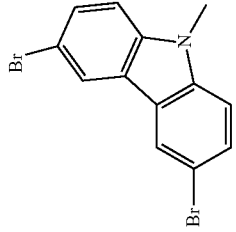 | 12.1/13.4 | 164.4 | 2.5 | 84.7 | | |
| S164 | 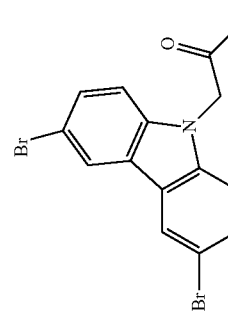 | 7.6 | 92.6 | 1.3 | 29.2 | | |
| S165 | 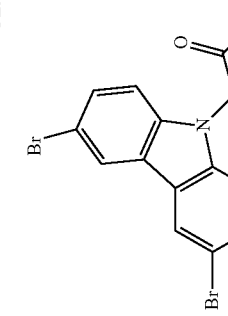 | 17.9/12.4 | 0.0 | 1.3 | 0.0 | | |

TABLE 1-continued
| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S168 | 14.6 | 79.7 | 3.5 | 30.3 | | |
| S169 | 9.2 | 39.2 | 3.0 | 29.2 | | |
| S170 | 11.2 | 0.0 | 1.5 | 0.0 | | |
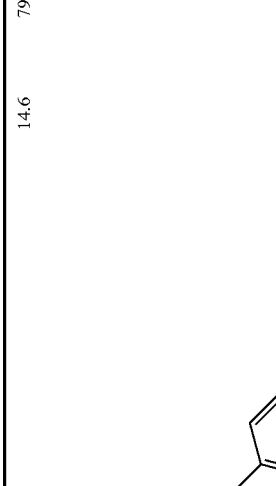

TABLE 1-continued

| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S171 | 3,6-dibromo-9-(2-hydroxyethyl)carbazole | 13.1 | 22.1 | 3.2 | 0.0 | | |
| S172 | 9-(2-hydroxy-3-phenoxypropyl)-β-carboline-3-carboxylic acid | 14.2 | −19.4 | 1.1 | | | |
| S173 | 6-bromo-9-(2-hydroxy-3-phenoxypropyl)-β-carboline-3-carboxylic acid | 12.8 | −18.7 | 1.0 | | | |

TABLE 1-continued

| compund # | | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S174 | (structure) | 9.3 | 224.2 | 1.8 | 0.0 | | |
| S176 | (structure) | 14.1/6.9 | −84.4 | 4.1 | | | |
| S177 | (structure) | 13.9 | −51.0 | 4.3 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S178 | | 13.8 | 167.1 | 1.7 | 36.2 | | |
| S179 | | 17.3 | −21.9 | 0.9 | | | |
| S180 | | 13.0/9.4 | 35.7 | 3.2 | 31.0 | | |
| S181 | | 11.3/8.3 | −17.5 | 0.9 | | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S182 | | 6.8 | −20.1 | 1.1 | | | |
| S183 | | 7.7 | 64.1 | 4.0 | 0.0 | | |
| S184 | | 6.7 | 0.0 | 2.5 | 0.0 | | |

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes | structure |
|---|---|---|---|---|---|---|---|
| S185 | 12.6 | 0.0 | 1.5 | 0.0 | | | |
| S186 | 8.1 | 232.6 | 3.4 | 69.1 | | | |
| S187 | 12.6 | 258.9 | 2.9 | 101.7 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S188 | | 13.1 | 173.1 | 3.1 | 39.6 | | |
| S189 | | 6.9 | 60.9 | 3.6 | 25.5 | 1.06 | |
| S190 | | 8.4 | 787.6 | 4.1 | 1310.0 | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S192 | | 10.5 | 396.2 | 4.2 | 422.6 | | |
| S193 | | 7.8 | 0.0 | 1.1 | 0.0 | | |
| S194 | | 8.1 | 1948.4 | 5.1 | 0.0 | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S195 | | 9.0 | 20.0 | 1.1 | 0.0 | | |
| S198 | | 11.0 | 474.2 | 5.1 | 1054.7 | | |
| S199 | | 13.3 | −49.5 | 1.1 | | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S200 | | 11.1 | 0.0 | 1.3 | 0.0 | | PK11195 (TSPO) |
| S203 | | 10.8 | 35.1 | 3.9 | 30.3 | 1.00 | |
| S204 | | 14.2 | 22.2 | 2.3 | 0.0 | | |
| S205 | | 14.6 | 27.9 | 2.5 | 46.7 | | |

TABLE 1-continued
| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S206 | 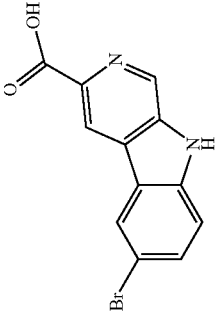 | 14.8 | | 1.4 | 0.0 | | |
| S207 | 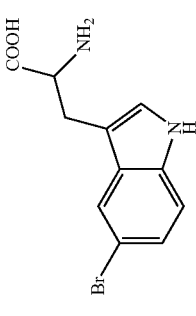 | 16.2 | 0.0 | 1.1 | 0.0 | | |
| S208 | 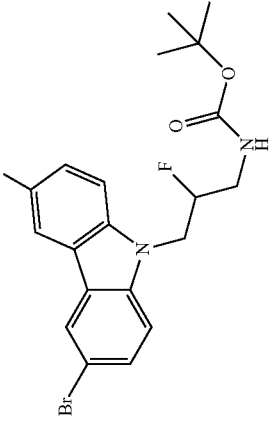 | 13.5 | 128.3 | 1.2 | 111.0 | 1.16 | |
| S209 | 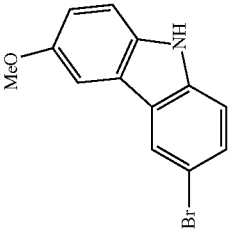 | 15.0 | 20.0 | 3.7 | 0.0 | | |

TABLE 1-continued
| compound # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S210 | 10.7 | 0.0 | 1.1 | 0.0 | | |
| S211 | 11.5 | 0.0 | 1.2 | 0.0 | | |
| S212 | 10.3 | 20.0 | 1.0 | 0.0 | 1.04 | |
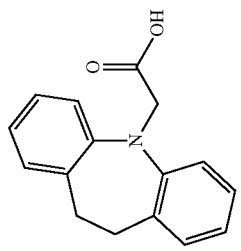
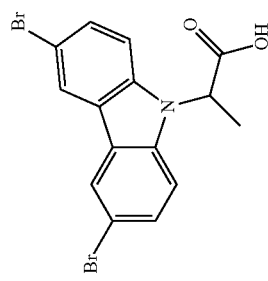
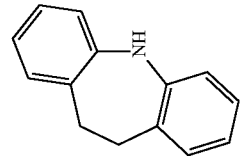

TABLE 1-continued

| compund # | structure | Neurogenesis # BrdU+ Cells (X10E06)/mm3 Dentate Gyrus | Dox:tox protection Δ(Sinf-S0/AC50) | Binding competition | NAD recovery Δ(Sinf-S0/AC50) | NAMPT activation | notes |
|---|---|---|---|---|---|---|---|
| S213 | 3,6-dibromo-carbazole-N-CH2-C(O)NH2 | 6.5 | 39.7 | 1.1 | 27.4 | 1.00 | |
| S214 | 3,6-dibromo-carbazole-N-CH2-C(O)NHCH3 | 9.9 | 206.5 | 1.7 | 41.1 | | |
| S215 | 3,6-dibromo-carbazole-N-CH2-C(O)N(CH3)2 | 8.3 | 220.4 | 3.6 | 68.7 | | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S216 | | 13.0 | 25.6 | 4.4 | 29.9 | | |
| S217 | | 12.3 | −22.5 | 2.6 | | 0.89 | |
| S218 | | 9.5 | 469.6 | 3.2 | 126.7 | | |
| S219 | | 8.4 | −26.9 | 3.1 | | | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S220 | | 10.5 | 22.2 | 2.9 | 26.3 | | |
| S221 | | 14.8 | 82.8 | 2.9 | 56.2 | | |
| S222 | | 15.1 | 0.0 | 1.3 | 0.0 | 1.02 | |
| S223 | | 7.9 | 23.8 | 3.0 | 28.2 | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S224 | | 10.1 | 0.0 | 1.3 | 0.0 | | |
| S225 | | 15.2 | 30.9 | 2.2 | 30.4 | | |
| S226 | | 12.8 | 49.2 | 1.9 | 33.5 | 0.96 | |
| S227 | | 12.9 | 0.0 | 0.9 | 0.0 | | |

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S228 | 20.2 | 90.1 | 2.0 | 30.3 | | |
| S230 | 15.3 | 0.0 | 1.0 | 0.0 | 1.02 | |
| S231 | 13.1 | −35.0 | 1.7 | | | |

TABLE 1-continued
| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S232 | 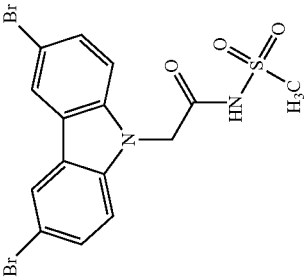 | 8.4 | 0.0 | 0.9 | 0.0 | 1.00 | |
| S233 | 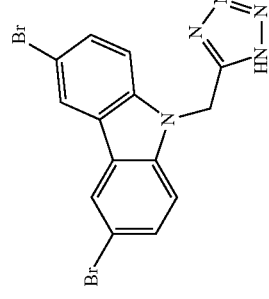 | 7.3 | 0.0 | 0.9 | 0.0 | 0.88 | |
| S234 | 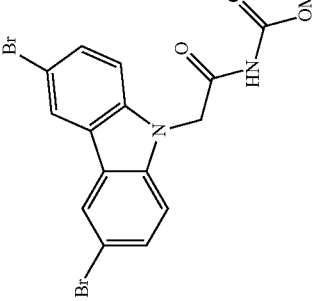 | 17.8 | 20.0 | 1.0 | 0.0 | 0.93 | |

TABLE 1-continued

| compound # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S235 | 3,6-dibromo-9-(cyanomethyl)carbazole | 11.7 | 24.6 | 1.8 | 0.0 | 0.97 | |
| S236 | 3-bromocarbazole | 12.3 | 0.0 | 1.7 | 0.0 | | |
| S237 | 3,6-dimethylcarbazole | 11.8 | 22.6 | 1.5 | 0.0 | | |
| S238 | 6-bromo-3-carbamoyl-9-(carboxymethyl)carbazole | 9.4 | 0.0 | 0.9 | 0.0 | | |

TABLE 1-continued

| compund # | structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S239 | | 11.4 | 0.0 | 0.9 | 0.0 | | |
| S240 | | 14.3 | 0.0 | 1.7 | 0.0 | | |
| S241 | | 15.5 | −14.7 | 1.3 | | | |
| S242 | | 10.8 | 0.0 | 1.2 | 0.0 | | |

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| S243 | 17.9/ 19.7 | 184.7 | 2.2 | 184.7 | 1.26 | |
| S244 | 11.6 | −17.2 | 1.1 | | | |
| S245 | 16.2 | 20.0 | 1.0 | 0.0 | | |

TABLE 1-continued

| compund # | Structure | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|---|
| S246 | | 14.5 | | 1.3 | | | |
| S247 | | 15.6 | 92.6 | 1.6 | 0.0 | | |
| S248 | | 10.1 | 0.0 | 1.3 | 0.0 | | |

TABLE 1-continued

| compund # | Neurogenesis # BrdU+ Cells (X10E06)/mm3 Dentate Gyrus | Dox:tox protection Δ(Sinf-S0/AC50 | Binding competition | NAD recovery Δ(Sinf-S0/AC50 | NAMPT activation | notes |
|---|---|---|---|---|---|---|
| (−)-S243 | 18.1 | 402.1 | 4.8 | 369.4 | 1.33 | |
| (+)-S243 | 10.0 | 80.4 | 4.2 | 92.3 | 1.13 | |
| S326 | | | | | 1.10 | |

TABLE 2

| Protein | Description | Length (AA) | mw (Da) | Indistinguishable Proteins | Spot number 1 | 2 | 3 | 4 |
|---|---|---|---|---|---|---|---|---|
| | | | | | % coverage | | | |
| P43490 | NAMPT_HUMAN Nicotinamide phosphoribosyltransferase | 491 | 55630.70 | | 11.95 | 81.73 | 37.85 | 61.77 |
| P11413 | G6PD_HUMAN Glucose-6-phosphate 1-dehydrogenase | 515 | 62590.70 | P11413-2; P11413-3; | 4.98 | 1.00 | 2.99 | 1.00 |
| Q86YZ3 | HORN_HUMAN Hornerin | 2850 | 283074.00 | | 4.00 | | | |
| F5GWF6 | F5GWF6_HUMAN T-complex protein 1 subunit beta | 530 | 52828.60 | F8VQ14; P78371; P78371-2; | 4.00 | 1.00 | 3.00 | |
| P00390 | GSHR_HUMAN Glutathione reductase, mitochondrial | 522 | 47363.30 | P00390-2; P00390-3; P00390-4; 00390-5; | 1.00 | 2.00 | 4.00 | 3.99 |
| C9J8Q5 | C9J8Q5_HUMAN Succinate-semialdehyde dehydrogenase, mitochondrial | 507 | 58778.20 | P51649; F51649-2; | | 1.00 | 4.00 | 3.00 |
| Q9Y265 | RUVB1_HUMAN RuvB-like 1 | 456 | 42208.00 | Q9Y265-2; | 3.98 | | | |
| K7ENP3 | K7ENP3_HUMAN ATP synthase subunit alpha | 531 | 54603.60 | P25705; P25705-2; | 0.98 | 0.98 | 1.97 | 3.96 |
| P04083 | ANXA1_HUMAN Annexin A1 | 346 | 38780.00 | | | | | 3.00 |
| B3KV55 | B3KV55_HUMAN Glutamate dehydrogenase | 391 | 61521.30 | B4DGN5; CONT_DHE3_BOVIN; P00367; | | 2.98 | | |
| P30837 | AL1B1_HUMAN Aldehyde dehydrogenase X, mitochondrial | 517 | 57314.30 | | 2.55 | | | 0.55 |
| P04279 | SEMG1_HUMAN Semenogelin-1 | 462 | 52225.90 | | 2.52 | 1.00 | 1.52 | 1.52 |
| B4E3LO | B4E3L0_HUMAN WD40 repeat-containing protein SMU1 | 352 | 57651.30 | Q2TAY7; | | 2.00 | 1.00 | 2.00 |
| P23246 | SFPQ_HUMAN Splicing factor, proline- and glutamine-rich | 707 | 76299.70 | | | | 0.99 | 1.99 |
| P14868 | SYDC_HUMAN Aspartate-tRNA ligase, cytoplasmic | 501 | 45850.20 | Q68CR9; | 1.98 | 0.99 | | |
| E7EUE5 | E7EUE5_HUMAN Aldehyde dehydrogenase, mitochondrial | 470 | 56489.70 | F8VX15; F8W0A9; P05091; | 1.00 | | | |
| P60709 | ACTB_HUMAN Actin, cytoplasmic 1 | 375 | 41873.90 | P63261; | | | | 0.94 |
| A8MVQ3 | A8MVQ3_HUMAN Cysteine--tRNA ligase, cytoplasmic | 738 | 94812.00 | B4DKY1; P49589; P49589-2; P49589-3; | | | | |

The invention claimed is:

1. A method for identifying a compound having cell-protective activity, comprising:
   exposing a population of cells to a test compound and a DNA-damaging agent;
   determining survival rate of the population of cells;
   wherein an increase in the survival rate compared to a control that is not treated with the test compound is indicative of cell-protective activity of the test compound; and
   incubating the test compound with nicotinamide phosphoribosyltransferase (NAMPT) and measuring an activity of the NAMPT, wherein an increase in the activity of the NAMPT additionally confirms the cell-protective activity of the test compound.

2. The method of claim 1, wherein the exposing step comprises incubating the population of cells with the test compound and the DNA-damaging agent.

3. The method of claim 1, wherein the exposing step comprises incubating the population of cells with the test compound first, followed by the DNA-damaging agent.

4. The method of claim 1, wherein the exposing step comprises incubating the population of cells with the DNA-damaging agent first, followed by the test compound.

5. The method of claim 1, wherein the DNA-damaging agent activates poly-ADP-ribose polymerase (PARP).

6. The method of claim 5, wherein the DNA-damaging agent leads to decline in nicotinamide adenine dinucleotide (NAD) level.

7. The method of claim 1, wherein the DNA-damaging agent is an anthracycline.

8. The method of claim 7, wherein the anthracycline is one or more of daunorubicin, doxorubicin, epirubicin, idarubicin, valrubicin and mitoxantrone.

9. The method of claim 8, wherein the anthracycline is doxorubicin.

10. The method of claim 1, wherein the cells are mammalian cells.

11. The method of claim 1, wherein the test compound is provided at about 1-20 uM, or about 2-10 uM or about 5 uM.

12. The method of claim 1, wherein the test compound is a small molecule.

13. The method of claim 1, wherein the DNA-damaging agent is provided at about 0.01-20 uM, or about 0.05-10 uM, or about 0.1-1.5 uM, or about 0.5 uM.

14. The method of claim 1, further comprising determining the test compound having said cell-protective activity protects the cells from toxicity mediated by the DNA-damaging agent.

15. The method of claim 1, further comprising determining the test compound having said cell-protective activity does not protect the cells from toxicity induced by a toxin selected from the group consisting of bortezomib, staurosporine, taxol, brefeldin, cytochalasin D, TNFa and TRAIL.

16. The method of claim 12, further comprising determining the test compound having said cell-protective activity increases nicotinamide adenine dinucleotide (NAD) level.

17. The method of claim 1, further comprising determining the test compound having said cell-protective activity binds and/or activates the NAMPT.

18. The method of claim 1, wherein the cell-protective activity is neuroprotective activity which includes one or more of: promoting survival, health, integrity, growth, development and/or function of neurons, protecting neurons from cell death, apoptosis and/or degeneration, and stimulating neurogenesis.

* * * * *